(12) United States Patent
Grandi et al.

(10) Patent No.: US 11,027,004 B2
(45) Date of Patent: Jun. 8, 2021

(54) IMMUNOGENIC COMPOSITIONS CONTAINING BACTERIAL OUTER MEMBRANE VESICLES

(71) Applicant: UNIVERSITA' DEGLI STUDI DI TRENTO, Trento (IT)

(72) Inventors: Guido Grandi, Segrate (IT); Laura Fantappie', Florence (IT); Carmela Irene, Trento (IT)

(73) Assignee: BIOMVIS SRL, Siena (IT)

( * ) Notice: Subject to any disclaimer, the term of this patent is extended or adjusted under 35 U.S.C. 154(b) by 448 days.

(21) Appl. No.: 15/790,472

(22) Filed: Oct. 23, 2017

(65) Prior Publication Data
US 2018/0207255 A1    Jul. 26, 2018

(30) Foreign Application Priority Data
Oct. 24, 2016  (EP) .................................... 16195315

(51) Int. Cl.
| | | |
|---|---|---|
| *A61K 39/02* | (2006.01) | |
| *C12N 1/00* | (2006.01) | |
| *C12N 1/20* | (2006.01) | |
| *A61K 39/09* | (2006.01) | |
| *A61K 39/085* | (2006.01) | |
| *C07K 14/31* | (2006.01) | |
| *C07K 14/315* | (2006.01) | |
| *C07K 14/195* | (2006.01) | |
| *A61K 39/00* | (2006.01) | |
| *C12R 1/19* | (2006.01) | |
| *C12N 15/70* | (2006.01) | |

(52) U.S. Cl.
CPC ............ *A61K 39/092* (2013.01); *A61K 39/02* (2013.01); *A61K 39/085* (2013.01); *C07K 14/195* (2013.01); *C07K 14/31* (2013.01); *C07K 14/315* (2013.01); *A61K 2039/60* (2013.01); *A61K 2039/6018* (2013.01); *C12N 1/20* (2013.01); *C12N 15/70* (2013.01); *C12R 1/19* (2013.01)

(58) Field of Classification Search
CPC ................ A61K 39/092; A61K 39/085; A61K 2039/60; C07K 14/195; C07K 14/31; C07K 14/315
See application file for complete search history.

(56) References Cited

U.S. PATENT DOCUMENTS

| | | | | |
|---|---|---|---|---|
| 2004/0110670 | A1* | 6/2004 | Arico ..................... | C12Q 1/689 435/252.3 |
| 2006/0251670 | A1* | 11/2006 | Comanducci ........ | A61K 39/095 424/190.1 |
| 2009/0035328 | A1* | 2/2009 | Granoff ................ | A61K 39/095 424/200.1 |
| 2011/0020390 | A1* | 1/2011 | Pizza .................... | A61K 39/095 424/197.11 |
| 2013/0022633 | A1* | 1/2013 | Banci .................... | C07K 14/22 424/190.1 |

FOREIGN PATENT DOCUMENTS

| | | |
|---|---|---|
| WO | 2010130899 A1 | 11/2010 |
| WO | 2015144691 A1 | 10/2015 |

OTHER PUBLICATIONS

Bridges K.M., et al., Probing the lipoprotein secretion pathway in Borrelia Burgdorferi, Jul. 22, 2012, retrieved from the Internet https://kuscholarworks.ku.edu/bitstream/handle/1808/9989/Bridges_ku_0099D_12171_DATA_1.pdf? sequence=1&isAllowed=y.
European Search Report of EP 16195315 dated Feb. 7, 2017.
Fukuda A., et al., "Aminoacylation of the N-terminal cysteine is essential for Lol-dependent release of lipoproteins from membranes but does not depend on lipoprotein sorting signals", Journal of Biological Chemistry, American Society for Biochemistry and Molecular Biology, US, vol. 277, No. 45, Nov. 8, 2002, pp. 43512-43518.
Kovacs-Simon et al., "Lipoproteins of Bacterial Pathogens", Infection and Immunity, vol. 79, No. 2, Feb. 1, 2011, pp. 548-561.
Tokuda et al., "Biogenesis of outer membranes in gram-negative bacteria", Bioscience Biotechnology Biochemistry, Japan Society for Bioscience, Biotechnology and Agrochemistry, Tokyo, Japan, vol. 73, No. 1, Jan. 1, 2009, pp. 465-473.

* cited by examiner

*Primary Examiner* — Gary B Nickol
*Assistant Examiner* — Lakia J Jackson-Tongue
(74) *Attorney, Agent, or Firm* — Silvia Salvadori, P.C.; Silvia Salvadori

(57) ABSTRACT

This invention relates to outer membrane vesicles (OMVs) from Gram-negative bacteria. The vesicles comprise heterologous proteins or immunogenic fragments thereof expressed as lipoproteins in their membrane. The OMVs of the invention are capable of eliciting an immune response to the heterologous protein or to a fragment thereof when administered to a mammal. Other aspects of the invention relate to methods of preparing the OMVs and immunogenic compositions containing the same.

8 Claims, 28 Drawing Sheets
Specification includes a Sequence Listing.

IMMUNOGENIC COMPOSITIONS CONTAINING BACTERIAL OUTER MEMBRANE VESICLES

TECHNICAL FIELD

This invention relates to vesicles from Gram-negative bacteria. The vesicles comprise heterologous proteins in their membrane expressed as lipoproteins. The vesicles are particularly useful in immunogenic compositions, e.g. vaccines.

BACKGROUND ART

Bacterial Lipoproteins and Lipidation

Bacterial lipoproteins are a class of peripherally anchored membrane proteins, which play key roles in basic bacterial physiology as well as in pathogenic mechanisms such as adhesion, colonization, invasion and immune evasion.

While in Gram-positive bacteria lipoproteins cross the membrane and remain attached on its external side through their lipid chains, in Gram-negative bacteria they can be found in three different cellular compartments: 1) attached to the periplasmic side of the inner membrane, 2) attached to the periplasmic side of the outer membrane, and 3) exposed on the surface of the outer membrane (OM). Lipoproteins are synthesized in the bacterial cytosol as precursors (pre-prolipoproteins) carrying a signal (or leader) peptide (LP) characterized by the specific conserved sequence Leu-(Ala/Ser)-(Gly/Ala)-Cys at its C-terminal region, known as "lipobox" (Kovacs-Simon, A., et al. 2011; Hutchings, M. I., et al., 2009). Once crossed the inner membrane, preprolipoproteins are first modified by a diacylglyceryl transferase (Lgt), which transfers a diacylglyceride to the cysteine sulfhydryl of the lipobox, forming a prolipoprotein. Subsequently, a specific signal peptidase (Lsp) cleaves the amide bond preceding the cysteine residue and the resulting diacylated apolipoprotein remains anchored to the membrane via the acyl moieties. Finally, an N-acyltransferase (Lnt) attaches a third acyl group to the free amino group of the N-terminal cysteine, creating a mature tri-acylated lipoprotein. Once tri-acylated, lipoproteins are ready to be translocated to the inner leaflet of the outer membrane. The transport is mediated by the Lol system, consisting of a transmembrane protein complex (LolCDE), an ATP-binding cassette (ABC) transporter, a periplasmic chaperone (LolA) and an outer-membrane receptor (LolB) (Tokuda, H., et al. 2009). All lipoproteins undergo the Lol-dependent translocation unless the lipidated cysteine is followed by specific amino acids (Tokuda, H. and S. Matsuyama, 2004; Bos, M. P., et al. 2007). In particular, the presence at position +2 of an aspartic acid has been shown to be sufficient to prevent most of lipoproteins from being transported to the outer membrane. While the final destination of many lipoproteins is the inner leaflet of the outer membrane, a group of lipoproteins reaches the bacterial surface. For instance, some lipoproteins are transported through the OM using the Type II Secretion System (T2SS) (for instance, the *K. oxytoca* PulA [d'Enfert, C., A. Ryter, and A. P. Pugsley (1987) EMBO J, 1987, 6, 3531]) and the Type V Secretion System (T5SS) (for instance, the *N. meningitidis* NalP [van Ulsen, P., et al., (2003) Mol Microbiol, 50, 1017; Oomen, C. J., et al., (2004) EMBO J, 23, 1257]). Other lipoproteins can reach the surface using the Bam complex (Konovalova, A., et al., (2014) Proc Natl Acad Sci USA, 111, 4350). A third group of lipoproteins cross the outer membrane using lipoprotein-specific flippases (Schulze, R. J., et al. (2010), Mol Microbiol, 76, 1266; Hooda, Y., et al. (2016) Nature Microbiology, 1, 16009). Finally, a last group of lipoproteins, here referred to as "promiscuous lipoproteins", are transported all the way to the bacterial surface using a transport process still not elucidated but conserved among many Gram-negative species.

Lipoproteins play an important role in pathogen recognition by the host and in the elicitation of innate and adaptive immunity. It is now well documented that TLR2, one of the ten human TLRs, recognizes lipoproteins that are anchored to the bacterial membrane by the lipid chains covalently attached to the N-terminal cysteine. Lipoprotein-TLR2 binding triggers a signal cascade that ultimately leads to the activation of innate immune responses and promotes the elicitation of adaptive immunity. The ligand-binding specificity of TLR2 is modulated by its propensity to form heterodimers either with TLR1 (TLR1/TLR2 heterodimer) or with TLR6 (TLR2/TLR6 heterodimers). TLR1/TLR2 heterodimers signal the presence of the triacylated lipoproteins of Gram-negative bacteria while the signaling through TLR2/TLR6 heterodimers is activated by the Gram-positive diacylated lipoproteins.

Outer membrane-associated lipoproteins become part of Outer membrane Vesicles (OMVs) proteome. Therefore, because of their TLR2 agonistic activity they are expected to contribute to the overall adjuvanticity of bacterial vesicles. Indeed, their role in OMV immunogenicity has been documented (Ellis et al., (2010) *Infect. Immun.* 78, 3822; Rosenthal et al., (2014) *PLoS ONE*, 9, e112802) and their adjuvanticity property has been proposed to synergize with other immunostimulatory components of OMVs.

However, the contribution of the different OMV-associated lipoproteins to the immunostimulatory properties of OMVs has not been dissected and fully elucidated so far.

Bacterial Outer Membrane Vesicles (OMVs)

Gram-negative bacteria can spontaneously release outer membrane vesicles (OMVs) during growth due to the turgor pressure of the cell envelope. OMVs are closed spheroid particles of a heterogeneous size, 20-300 nm in diameter, generated through a "budding out" of the bacterial outer membrane. Consistent with that, the majority of OMV components are represented by LPS, glycerophospholipids, outer membrane proteins, lipoproteins and periplasmic proteins (A. Kulp and Kuehn M. J. (2010) *Annu. Rev. Microbiol.* 64, 163-184; T. N. Ellis and Kuehn M. J. (2010) *Microbiol. Mol. Biol. Rev.* 74, 81-94).

OMVs represent a distinct secretory pathway with a multitude of functions, including inter and intra species cell-to-cell cross-talk, biofilm formation, genetic transformation, defense against host immune responses and toxin and virulence factor delivery to host cells (A. Kulp and Kuehn M. J. (2010) *Annu. Rev. Microbiol.* 64, 163-184). OMVs interaction to host cells can occur by endocytosis after binding to host cell receptors or lipid rafts. Alternatively, OMVs have been reported to fuse to host cell membrane, leading to the direct release of their content into the cytoplasm of the host cells (A. Kulp and Kuehn M. J. (2010) *Annu. Rev. Microbiol.* 64, 163-184; T. N. Ellis and Kuehen M. J. (2010) *Micrbiol. Mol. Biol. Rev.* 74, 81-94).

OMVs purified from several pathogens, including *Neisseria, Salmonella, Pseudomonas, Vibrio cholerae Burkholderia*, and *E. coli*, induce potent protective immune responses against the pathogens they derive from (B. S. Collins (2011) *Discovery Medicine*, 12, 7-15), and highly efficacious anti-*Neisseria* OMV-based vaccines are already available for human use (J. Hoist et al. (2009) *Vaccine*, 27S, B3-B12). Such remarkable protection is attributed to two main properties of OMVs. First, they carry the proper immunogenic and protective antigens which, in extracellular pathogens, usually reside on the surface and therefore are naturally incorporated in OMVs. Indeed, OMV immunization induces potent antibody responses against the major membrane-associated antigens. However, OMV immunogenicity is not restricted to antibody responses. For instance, mice immunized with *Salmonella* OMVs develop robust *Salmonella*-specific B and T cell responses, and OMVs stimulate IFN-γ production by a large proportion of CD4+ T cells from mice previously infected with *Salmonella*, indicating that OMVs are an abundant source of antigens recognized by *Salmonella*-specific CD4+ T cells (R. C. Alaniz et al., (2007) *J. Immunol.* 179, 7692-7701). Second, OMVs possess a strong "built-in" adjuvanticity since they carry many of the bacterial Pathogen-Associated-Molecular Patterns (PAMPs) which, by binding to pathogen recognition receptors (PRRs), play a key role in stimulating innate immunity and in promoting adaptive immune responses. OMV-associated PAMPs include LPS which, in concert with MD-2 and CD14, binds TLR-4, lipoproteins whose acylpeptide derivatives interact with TLR-1/2 and 2/6 heterodimers, and peptidoglycan whose degradation products bind to intracellular NOD1/2 (A. Moshiri etal., *Hum. Vaccines. Immunother.* (2012) 8, 953-955; T. N. Ellis et al., (2010) *Inn. Immun.* 78, 3822-3831; M. Kaparakis et al., (2010) *Cell. Miocrobiol.* 12, 372-385). The engagement of this group of PPRs results in the activation of transcription factors (NF-kB) and the consequent expression of specific cytokines. Interestingly, LPS, lipoproteins and peptidoglycan can work synergistically, thus potentiating the built-in adjuvanticity of OMVs (D. J. Chen et al., (2010) *PNAS,* 107, 3099-3104).

OMVs also have the capacity to induce protection at the mucosal level. Protection at the mucosal sites is known to be at least partially mediated by the presence of pathogen-specific IgAs and Th17 cells. In particular, a growing body of evidence suggests that Th17 cells have evolved to mediate protective immunity against a variety of pathogens at different mucosal sites. Interestingly, Th17 cells have recently also been shown to play a crucial role in the generation of vaccine-induced protective responses. For instance, it has been reported that in mice whole cell pertussis vaccines (Pw) induce Th17 cells and neutralization of IL-17 after vaccination reduces protection against a pulmonary challenge with *B. pertussis*. Similarly, in a CD4+ T cell dependent, antibody-independent model of vaccine-induced protection following *S. pneumoniae* challenge, treatment with IL-17-antibodies resulted in reduced immunity to pneumococcal colonization compared to the control serum treated mice (Malley R, et al. (2006) *Infect Immun.,* 74:2187-95). Elicitation of IgAs and Th17 cells by OMVs has been well documented and this can explain mechanistically the good protective activities of OMVs against several mucosal pathogens. For instance, immunization with *Vibrio cholerae*-derived OMVs protects rabbits against *Vibrio cholerae* oral challenge (Roy N. et al. (2010) *Immunol. Clinical Microbiol.* 60, 18-27) and *Pasteurella multocida*-derived and *Mannheimia haemolytica*-derived OMVs protect mice from oral challenge with *P. multocida* (Roier S. et al., (2013) *Int. J. Med. Microbiol.* 303, 247-256). In addition, intranasal immunization with *Porphyromonas gingivalis* OMVs elicits potent IgA production at both serum and mucosal level and immunization with *Escherichia coli*-derived OMVs prevent bacteria-induced lethality. Protective effect of *Escherichia coli*-derived OMVs is primarily mediated by OMV-specific, IFN-γ and IL-17 producing, T cells (Kim O Y et al., (2013) *J. Immunol.* 190, 4092-4102).

In addition to their "built-in" adjuvanticity, OMVs are becoming a promising vaccine platform for two main reasons.

1. OMVs are Amenable for Large Scale Production

In general, the amount of OMVs released by Gram-negative bacteria when grown under laboratory conditions is too low to allow their exploitation in biotechnological applications. However, two approaches can be used to enhance the yields of OMVs and make them compatible with industrial applications. The first one exploits the addition of mild detergents to the bacterial biomass to promote the vesiculation process and, at the same time, to decrease the level of OMV reactogenicity by removing a substantial amount of LPS (Fredriksen J. H. et al, (1991) NIPH Ann. 14, 67-79). Although this process has been proved to produce safe and effective vaccines against Meningococcal B (Granoff D. (2010), *Clin. Infect. Dis.* 50, S54-S65; Crum-Cianflone N, Sullivan E. (2016) Meningococcal vaccinations. *Infect Dis Ther.,* 5, 89-112) its main drawback is that the detergent treatment favors bacterial cell lysis with the consequence that the OMV preparations are heavily contaminated with cytoplasmic proteins (Ferrari et al., (2006) *Proteomics,* 6, 1856-1866). The second approach to enhance OMV production is to insert into the genome of the OMV-producing strain mutations that enhance vesiculation. For instance, in *Neisseria meningitidis*, a mutation in the gna33 gene, encoding a glucosyltransferase, has been shown to drive the release of several milligrams of vesicles per liter in the culture supernatant (Ferrari et al., (2006) *Proteomics,* 6, 1856-1866). Similar quantities of vesicles are obtained from *Escherichia coli* strains carrying deletions in the genes encoding the Tol/Pal system (a protein complex involved in the connection of the inner membrane with the outer membrane) (Bernadac A. et al., (1998) *J. Bacteriol.* 180, 4872-4878) and in the ompA gene, encoding one of the major outer membrane proteins of *E. coli* (Fantappiè et al., (2014) *Journal of Extracellular Vesicles,* 3, 24015). Such quantities make the production process of OMVs highly efficient and inexpensive. A number of other mutations have been described that enhance the production of OMVs in several Gram negative bacteria, including *Salmonella* and *E. coli* (Deatherage B. L. et al. (2009) *Mol. Microbiol.* 72, 1395-1407; McBroom A. J. and Kuehen M. J. (2007) *Mol. Microbiol.* 63, 545-558; Kulp et al., (2015) *PLos ONE* 10, e0139200).

As far as the purification of OMVs from the culture supernatant is concerned, centrifugation and tangential flow filtration (TFF) are commonly used. The yield of OMV production using centrifugation couple to TFF can easily exceed 100 mg/liter of culture (Berlanda Scorza F. et al., (2012) *PlosOne* 7, e35616) and therefore the process is perfectly compatible with large scale production.

2. OMVs can be Manipulated in their Protein Content by Genetic Engineering

This feature was demonstrated for the first time by Kesty and Kuehn who showed that *Yersinia enterocolitica* outer membrane protein Ail assembled on OMVs surface when expressed in *E. coli*, and that the GFP fluorescence protein fused to the "twin arginine transport (Tat)" signal sequence was incorporated in the OMV lumen (N. C. Kesty and Kuhen M. J. (2004) *J. Biol. Chem.* 279, 2069-2076). Following the observation by Kesty and Kuehn, an increasing number of heterologous proteins have been successfully delivered to OMVs using a variety of strategies. For instance, heterologous antigens have been delivered to the surface of OMVs by fusing them to the □-barrel forming autotransporter AIDA and to hemolysin ClyA, two proteins that naturally compartmentalized into *E. coli* OMVs (J. Schroeder and Aebischer T. (2009) *Vaccine*, 27, 6748-6754; D. J. Chen et al., (2010) *PNAS*, 107, 3099-3104). Recently, heterologous antigens from Group A *Streptococcus* and Group B *Streptococcus* were delivered to the lumen of *E. coli* vesicles by fusing their coding sequences to the leader peptide of *E. coli* OmpA. Interestingly, when the recombinant vesicles were used to immunize mice, they elicited high titers of functional antibodies against the heterologous antigens, despite their luminal location (Fantappiè et al., (2014) *Journal of Extracellular Vesicles*, 3, 24015).

The fascinating properties that make OMVs an attractive vaccine platform are somehow counterbalanced by a few limitations that need to be properly addressed for OMV full-blown exploitation.

1. First, as pointed out above, many strategies have been successfully used to deliver heterologous antigens to the vesicle compartment. However, a universal system working for any protein antigen has not been described yet. A strategy that is effective for one specific antigen in terms of level of expression and elicitation of immune responses can be inefficient with other antigens.

Therefore, the identification of novel strategies to deliver antigens to the OMV compartment is highly needed.

2. Second, one potential issue encountered in using OMVs in vaccine applications is the presence of lipopolysaccharide (LPS), an endotoxin known to be reactogenic both in animals and humans. To reduce OMV reactogenicity LPS can be at least partially removed using mild detergents (Fredriksen J. H. et al, (1991) *NIPH Ann.* 14, 67-79) or OMV can be formulated with alum hydroxide which absorbs LPS and keeps it confined at the site of injection (Ferrari et al., (2006) *Proteomics*, 6, 1856-1866; Snape M. D. et al., (2010) *Pediatr. Infect. Dis. J.* 29, e71-e79). Another strategy is to genetically alter the LPS synthetic pathway of the OMV producing strain so that the purified vesicles carry modified versions of LPS with reduced reactogenicity.

For instance, in *Neisseria meningitidis* one promising mutant with attenuated endotoxin activity contains a deletion in the lpxL1 gene (also referred to as the msbB gene) (Fisseha M. et al., (2005) *Infect. Immun.*, 73:4070-4080). This mutation results in a LPS carrying a penta-acylated lipid A, which has a lower agonistic activity on human Toll-like receptor 4 than the esa-acylated Lipid A (Steeghs L. et al. (2008) *Infect. Immun.*, 76:3801-3807). The inactivation of msbB gene to produce less toxigenic OMVs has also been reported for *Shigella*, *Salmonella* and *E. coli* (Berlanda Scorza F. et al., (2012) *PlosOne* 7, e35616; Lee S-R et al., (2009) *J. Microb. Biotechnol.* 19, 1271-1279; Dong H. L. et al., (2011) *Vaccine*, 29, 8293-8301). In *E. coli* an additional mutation in the pagP gene has been described that, when combined with msbB mutation, results in the production of LPS with a fully penta-acylated lipid A which has a low reactogenicity property (Dong H. L. et al., (2011) *Vaccine*, 29, 8293-8301). Finally, by using Synthetic Biology, Needham and co-workers (Needham B. D. et al., (2013) *PNAS*, 110, 1464-1469) have created a collection of novel LPS synthetic pathways which lead to the synthesis of LPS carrying different modifications, each displaying distinct TLR4 agonist activities, cytokine induction and reactogenicity properties.

In conclusion, LPS plays a key role in stimulating innate immunity and promoting adaptive immunity but, at the same time, it is reactogenic and potentially toxic. Therefore, strategies aimed at modifying the LPS structure and/or at modulating its expression and compartmentalization have high potential for the design of novel vaccines featuring optimal immunogenicity and adjuvanticity properties.

DISCLOSURE OF THE INVENTION

The inventors have found that if heterologous proteins are fused to lipoprotein leader sequences, the heterologous proteins are lipidated, reach the outer membrane and are incorporated into OMVs, and in particular in their membrane compartment. Importantly and particularly surprisingly, in this configuration lipidated heterologous proteins are expressed at high levels and compartmentalize in OMVs more efficiently than when expressed as periplasmic proteins. The inventors have also surprisingly found that when lipidated heterologous antigens are expressed in specific OMV-producing strains, they interfere with LPS production and/or transport such that OMVs are much less reactogenic. Finally, the inventors have found that OMVs decorated with lipidated heterologous antigens are able to elicit Th1-skewed antigen-specific immune responses when administered to a mammal.

Thus, in a first aspect, the invention provides an outer membrane vesicle (OMV) from a Gram-negative bacterium, wherein the OMV comprises at least one lipidated heterologous protein in the membrane (lipoprotein), and the OMV is capable of eliciting an immune response to the heterologous protein when administered to a mammal. The heterologous protein is lipidated at its N-terminal cysteine, the latter deriving from the cleavage of a leader sequence or signal peptide possessing a consensus sequence of the lipobox, which is attached to a precursor of the heterologous (lipo) protein. The (lipo)protein precursor is processed by the bacterial enzyme machinery (e.g. by the lipoprotein diacylglyceryl transferase, Lgt) to produce the lipidated heterologous protein carrying acyl residues at the N-terminal cysteine (as a general review on bacterial lipoproteins, see Kovacs-Simon A. et al, Infection and Immunity, February 2011, Vol. 79 no. 2 p. 548-561).

The heterologous protein is by definition a protein which is not produced by the Gram-negative bacterium from which the OMVs according to the invention are isolated. Typically the protein is an antigen from a pathogen genus different from the genus of bacterium from which the OMV is obtained. The protein may also be a human protein such as a tumor antigen. The OMVs may contain more than one heterologous protein.

The heterologous protein can be an amino acid polymer of any length. The amino acid polymer may be linear or branched, it may comprise modified amino acids and it may be interrupted by non-amino acids. The polymer may be modified naturally or by intervention, for example by disulfide bond formation, glycosylation, acetylation, phosphorylation.

According to the invention, the term 'heterologous protein' refers to bacterial, viral, parasitic and cancer proteins and/or antigens, including cytoplasmic or periplasmic proteins in the heterologous organism, membrane-associated proteins wherein the membrane-anchor may have been deleted or an antigen, including immunogenic fragments of proteins or polypeptides.

In a preferred embodiment of the invention, the heterologous protein is an immunogenic protein which can elicit an immune response in a mammal. The protein can elicit an immune response against a protist, a bacterium, a virus, a fungus or any other pathogen and any cancer cell type. The immune response may comprise an antibody response (usually including IgG) and/or a cell-mediated immune response. The antigens will typically elicit an immune response against the corresponding bacterial, viral, fungal or parasite polypeptide and cancer.

In preferred embodiments of the invention, the heterologous protein is selected from the group consisting of double mutant of extracellular cholesterol depending streptolysin O (Slo-dm) from *Streptococcus pyogenes*, the HlaH35L from *Staphylococcus aureus*, the Spa$_{KKAA}$ antigen from *Staphylococcus aureus*, the LukE antigen from *Staphylococcus aureus*, the FhuD2 antigen from *Staphylococcus aureus*, and the CsA1 antigen from *Staphylococcus aureus*.

In one embodiment the heterologous protein is Streptolysin O from *Streptococcus pyogenes* (GAS). The pore-forming toxin Streptolysin O (Slo) is one of the most up-regulated virulence factors in invasive GAS isolates (Feil et al. 2014. J Mol Biol 426: 785-792) and causes apoptotic cell death. In vitro and in vivo data support the hypothesis that Slo-induced toxicity contributes to GAS immune evasion and increased virulence. Immunization with Slo remarkably protects mice from the challenge with lethal doses of Slo-expressing GAS strains, thus making Slo a promising vaccine candidate (Bensi et. A, (2012) Mol. Cell. Proteomics 11: M111.015693). Similar protective activities are elicited by a Slo double mutant (Slo$_{dm}$), in which two amino acid substitutions were introduced: the Proline 427 was substituted by an Alanine residue and the Tryptophan 535 was substituted by a Phenylalanine residue (Chiarot et al, (2013) *M Bio* 4, e00387-12). This mutant has no toxic activity in that the protein is highly impaired in binding to eukaryotic cells, and is unable to form organized oligomeric structures on the cell surface (Chiarot et al, (2013) *M Bio* 4, e00387-12).

In another embodiment of invention the heterologous protein is the *Staphylococcus aureus* Hemolysin A (HLA). HLA is a β-barrel pore-forming cytotoxin. Passive immunization of mice with anti-Hla antisera provides protection from challenge both with purified toxin as well as live staphylococci (Menzies, B. E., and D. S. Kernodle. (1996) *Infect. Immun.* 64:1839-1841). Hla$_{H35L}$ is a variant toxin with a single amino acid substitution that cannot form cytolytic pores. Immune-sera against this variant protects mice *S. aureus* pneumonia (Wardenburg and Schneewind (2008) J. Exp. Med. 205:287-294).

In another embodiment of invention the heterologous protein is SpA$_{KKAA}$ (Kim et al., (2010) *J. Exp. Med.* 207, 1863), the Ig binding region of Staphylococcal protein A (SpA). SpA is a key virulence factor that enables *S. aureus* to evade innate and adaptive immune responses. SpA$_{KKAA}$ has been shown to induce protective immune responses against *S. aureus* and therefore is considered a promising component for anti-*S. aureus* vaccines (Kim et al., (2010) *J. Exp. Med.* 207, 1863).

In another embodiment of invention the heterologous protein is FhuD2 (ferric-hydroxamate uptakeD2). It has been shown that FhuD2 immunization confers protection in mouse staphylococcal infection models. The antigen was identified in a reverse vaccinology screening for *Staph aureus* vaccine candidates (Mishra et al. J. Infect. Dis. 206, 1041-1049).

In another embodiment of invention the heterologous protein is LukE. LukE, together with LukD, is part of a bi-component leukocidin (Alonzo & Torres, 2014). The bi-component pore-forming toxins have two separate protomers, the stem domain participates in the transmembrane β-barrel formation that ultimately perforates the membrane. LukED is one of the major virulence factors that *S. aureus* uses in bloodstream infections and it plays a critical role in pathogenesis, as shown by the fact that an isogenic highly virulent staphylococcal strain with lukED deleted has a dramatic attenuation in animal models (Alonzo et al., 2012; Reyes-Robles et al., 2013). LukE targets monocytes, neutrophils, macrophages, T-cells, dendritic cells and NK cells from various species, including mice. The broad host range of cell targeted by LukED has been partially clarified by the recent identification of CCR5, CXCR1 and CXCR2 as its binding partners (Alonzo et al., 2013; Reyes-Robles et al., 2013). Binding these three cellular receptors allows LukED to target both innate and adaptive immunity.

In another embodiment of invention the heterologous protein is CsA1, a protein recently discovered and belonging to a highly conserved Staphylococcal protein family. The protein was shown to be protective in *S. aureus* mouse models (Schluepen et al., (2013) Biochem J. 455, 273-84).

The N-terminal cysteine carrying the lipid moieties in the heterologous protein derives from the cleavage of a leader sequence which is attached to a precursor form of the heterologous protein. The precursor contains a leader sequence carrying a lipobox enabling protein lipidation. The lipobox is characterized by the presence of a carboxy-terminal cysteine whereby the cysteine becomes the first amino acid of the mature heterologous lipoprotein and serves as acceptor of acyl molecules. Preferably the lipobox has a sequence Leu-(Ala/Ser)-(Gly-Ala)-Cys (SEQ ID NO:111).

The OMVs of the invention can be obtained from any suitable Gram-negative bacterium. Preferably the Gram-negative bacterium is selected from the group consisting of *E. coli, N. menigitidis, Salmonella* sp., and *Shigella* sp., more preferably the Gram-negative bacterium is *E. coli*.

It has been observed that the amount of heterologous protein present in the OMVs of the invention is substantially increased with respect to the OMVs carrying the same heterologous antigen in a non-lipidated form.

In one embodiment the Gram-negative bacterium is a "hyperblebbing" strain in which the gene encoding OmpA, one of the major *E. coli* outer membrane proteins, has been inactivated or deleted. However, several other mutations leading to "hyper vesiculation" can be used. In particular, the following genes can be mutated to increase the production of vesicles: gna33 gene, encoding a glucosyltransferase, in *Neisseria meningitidis*; genes encoding the Tol/Pal system (a protein complex involved in the connection of the inner membrane with the outer membrane) in *Escherichia coli*; the ompA gene, encoding one of the major outer membrane proteins of *E. coli*. A number of other mutations have been described that enhance the production of OMVs in several Gram negative bacteria, including *Salmonella* and *E. coli* (Deatherage B. L. et al. (2009) *Mol. Microbiol.* 72, 1395-1407; McBroom A. J. and Kuehen M. J. (2007) *Mol. Microbiol.* 63, 545-558; Kulp et al., (2015) *PLos ONE* 10, e0139200).

In another embodiment of the invention, the OMV-producing strain carries mutations causing an alteration of LPS biosynthesis and/or compartimentalization, whereby OMVs show a substantially reduced TLR4 activation. For example, when the Gram-negative bacterium is *Neisseria meningitidis*, the lpxL1 gene is mutated (deleted) to attenuate endotoxin activity. This mutation results in a LPS carrying a penta-acylated lipid A, which has a lower agonistic activity on human Toll-like receptor 4 than the hexa-acylated Lipid A. In *Shigella, Salmonella* and *E. coli* the msbB gene can be inactivated to produce less toxigenic OMVs. In *E. coli* an additional mutation in the pagP gene, when combined with msbB mutation, results in the production of LPS with a fully penta-acylated lipid A which has a low reactogenicity property.

In a further embodiment, the invention provides a method of preparing an OMV as herein disclosed, wherein said method comprises the following steps:

(i) expressing, in a Gram-negative bacterium, the heterologous protein fused to a leader sequence carrying a C-terminal Cysteine, (ii) isolating the OMV containing the heterologous protein.

In one embodiment, the heterologous protein is expressed using a DNA sequence encoding the heterologous protein linked to a DNA sequence encoding a signal sequence of a lipoprotein, and the fused DNA sequences are integrated into the genome of the host strain producing the OMV.

In another embodiment, the heterologous protein is expressed using an RNA sequence encoding the heterologous protein operatively linked to an RNA sequence encoding a signal sequence of a lipoprotein and the fused RNA is expressed in the host strain producing the OMV.

In a preferred embodiment the heterologous protein is expressed in the membrane of OMVs as a lipoprotein using an expression vector comprising a nucleic acid sequence encoding the heterologous protein linked to a nucleic acid sequence encoding a signal sequence of a lipoprotein.

Any plasmid backbone suitable for bacterial gene expression known in the art can be used as an expression vector. Suitable plasmids include pGEX, pUC19, pALTR, pET, pQE, pLEX, pHAT or any other plasmid vector that is capable of replication in Gram-negative bacteria.

In a particular embodiment the expression vector is the pET21b-derived plasmid. In an alternative embodiment, the heterologous protein fused to a lipoprotein leader sequence can be integrated into the E. coli genome to create a stable strain expressing the protein of interest.

The signal sequence and the Gram-negative bacterium that can be used in the method of invention are described above.

The invention further provides an OMV obtainable by this method.

The invention also provides a pharmaceutical composition comprising (a) one or more OMVs of the invention and (b) a pharmaceutically acceptable carrier.

In a preferred embodiment, the pharmaceutical composition is an immunogenic composition. The immunogenic composition may contain a mixture of outer membrane vesicles carrying different heterologous proteins.

The compositions of the invention for administration to subjects are preferably vaccine compositions. Vaccines according to the invention may either be prophylactic or therapeutic. Pharmaceutical compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to stimulate antibody production, the degree of protection desired, the formulation of the vaccine, the doctor's assessment of the medical situation, and other relevant factors. The antigen content of compositions of the invention will generally be expressed in terms of the amount of protein per dose. The amount of OMVs in compositions of the invention may generally be between 10 and 500 µg, preferably between 25 and 200 µg, and more preferably about 50 µg or about 100 µg.

Compositions of the invention may be prepared in various liquid forms. For example, the compositions may be prepared as injectables, either as solutions or suspensions. The composition may be prepared for pulmonary administration e.g. by an inhaler, using a fine spray. The composition may be prepared for nasal, aural or ocular administration e.g. as spray or drops, and intranasal vesicle vaccines are known in the art. Injectables for intramuscular administration are typical. Injection may be via a needle (e.g. a hypodermic needle), but needle-free injection may alternatively be used.

The OMVs and the immunogenic compositions according to the invention are conveniently used for the stimulation of an immune response against bacterial or parasitic infections or other diseases including cancer, in a subject in need thereof.

The invention also provides a method of generating an immune response in a mammal, the method comprising administering an effective amount of an OMV comprising at least one lipidated heterologous protein according to the invention, or administering a pharmaceutical composition of the invention to the mammal, wherein the immune response is to the heterologous protein in the OMV.

The primers carry partially complementary 5' tails allowing the linear PCR product to recombine when transformed in *E. coli* cells and reconstitute the circularized plasmid with the C>A substitution (Lpp leader sequence—coding sequence SEQ ID NO:101, amino acid sequence SEQ ID NO:102).

Figure 9:
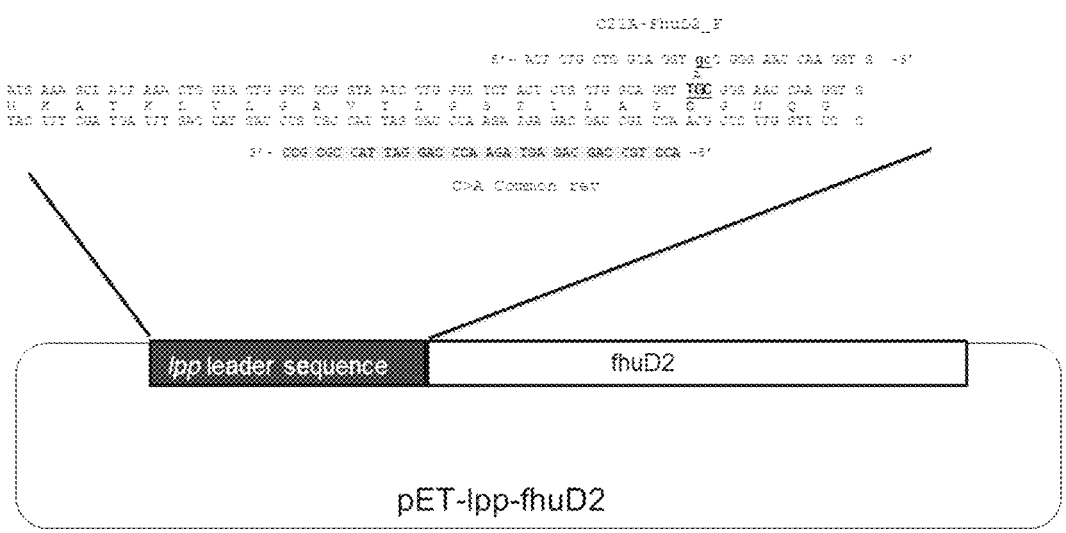

FIG. 9. Strategy used to mutagenize the cysteine residue in the lipobox of the Lpp leader sequence of pET-lpp-FhuD2 plasmid To generate pET-lpp-FhuD2-C>A plasmid we designed two primers, a reverse primer annealing upstream of the Cysteine codon to be changed (C>A common rev, SEQ ID NO:89) and a "mutagenic" forward primers (C21A-FhuD2_F, SEQ ID NO:90) carrying a two nucleotide "GC" mismatch which converts the TGC Cysteine codon into GCC Alanine codon.

The couple of primers carries also partially complementary 5' tails allowing the linear PCR product to recombine when transformed in *E. coli* cells and reconstitute the circularized plasmid with the C>A substitution (Lpp leader sequence—coding sequence SEQ ID NO:103, amino acid sequence SEQ ID NO:104).

Figure 10:
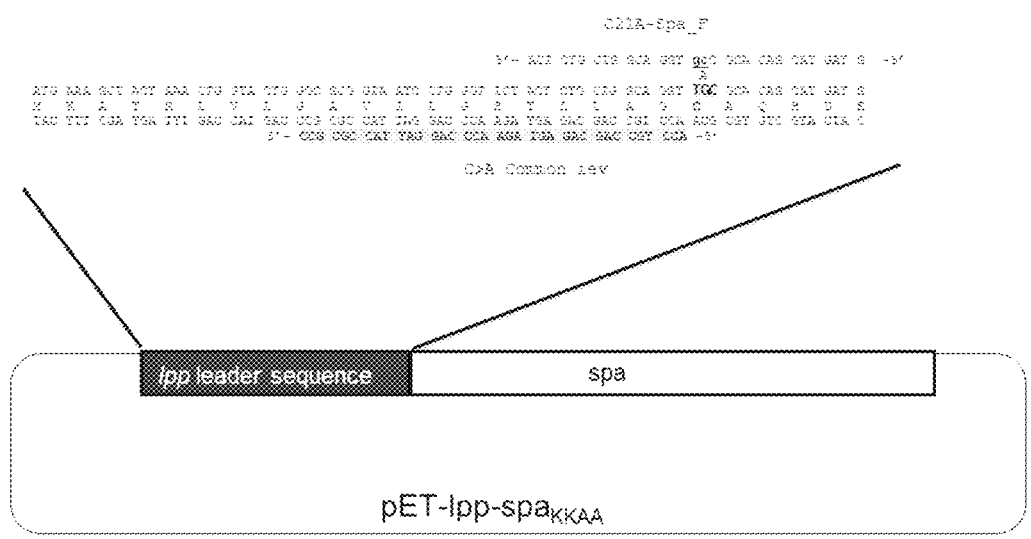

FIG. 10. Strategy used to mutagenize the cysteine residue in the lipobox of the Lpp leader sequence of pET-lpp-Spa$_{KKAA}$ plasmid To generate pET-lpp-Spa$_{KKAA}$-C>A plasmid we designed two primers, a reverse primer annealing upstream of the Cysteine codon to be changed (C>A common rev, SEQ ID NO:91) and a "mutagenic" forward primers (C21A-Spa_F, SEQ ID NO:92) carrying a two nucleotide "GC" mismatch which converts the TGC Cysteine codon into GCC Alanine codon.

The couple of primers carries also partially complementary 5' tails allowing the linear PCR product to recombine when transformed in *E. coli* cells and reconstitute the circularized plasmid with the C>A substitution (Lpp leader sequence—coding sequence SEQ ID NO:105, amino acid sequence SEQ ID NO:106).

Figure 11:
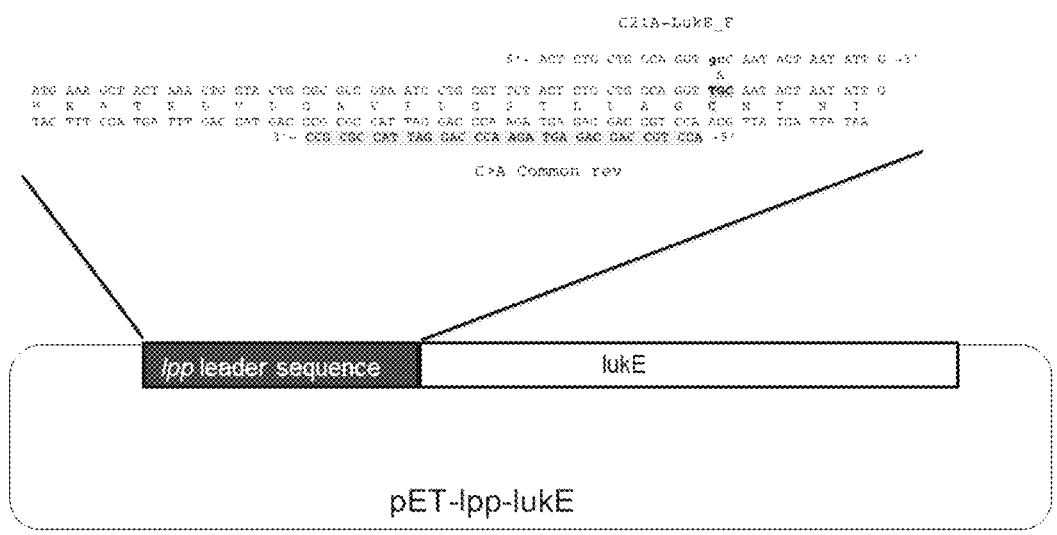

FIG. 11. Strategy used to mutagenize the cysteine residue in the lipobox of the Lpp leader sequence of pET-lpp-LukE plasmid To generate pET-lpp-LukE-C>A plasmid we designed two primers, a reverse primer annealing upstream of the Cysteine codon to be changed (C>A common rev, SEQ ID NO:93) and a "mutagenic" forward primers (C21A-LukE_F, SEQ ID NO:94) carrying a two nucleotide "GC" mismatch which converts the TGC Cysteine codon into GCC Alanine codon.

The couple of primers carries also partially complementary 5' tails allowing the linear PCR product to recombine when transformed in *E. coli* cells and reconstitute the circularized plasmid with the C>A substitution (Lpp leader sequence—coding sequence SEQ ID NO:107, amino acid sequence SEQ ID NO:108).

Figure 12:
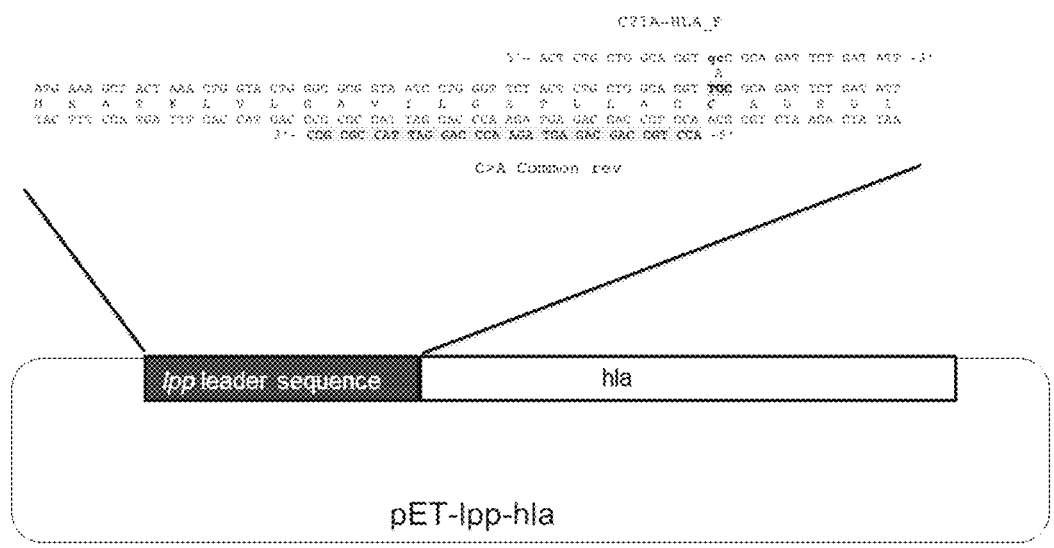

FIG. 12. Strategy used to mutagenize the cysteine residue in the lipobox of the Lpp leader sequence of pET-lpp-HLA$_{H35L}$ plasmid To generate pET-lpp-HLA$_{H35L}$-C>A plasmid we designed two primers, a reverse primer annealing upstream of the Cysteine codon to be changed (C>A common rev, SEQ ID NO:95) and a "mutagenic" forward primers (C21A-HLA$_{H35L}$_F, SEQ ID NO:96) carrying a two nucleotide "GC" mismatch which converts the TGC Cysteine codon into GCC Alanine codon.

The couple of primers carries also partially complementary 5' tails allowing the linear PCR product to recombine when transformed in *E. coli* cells and reconstitute the circularized plasmid with the C>A substitution (Lpp leader sequence—coding sequence SEQ ID NO:109, amino acid sequence SEQ ID NO:110).

Figure 13:
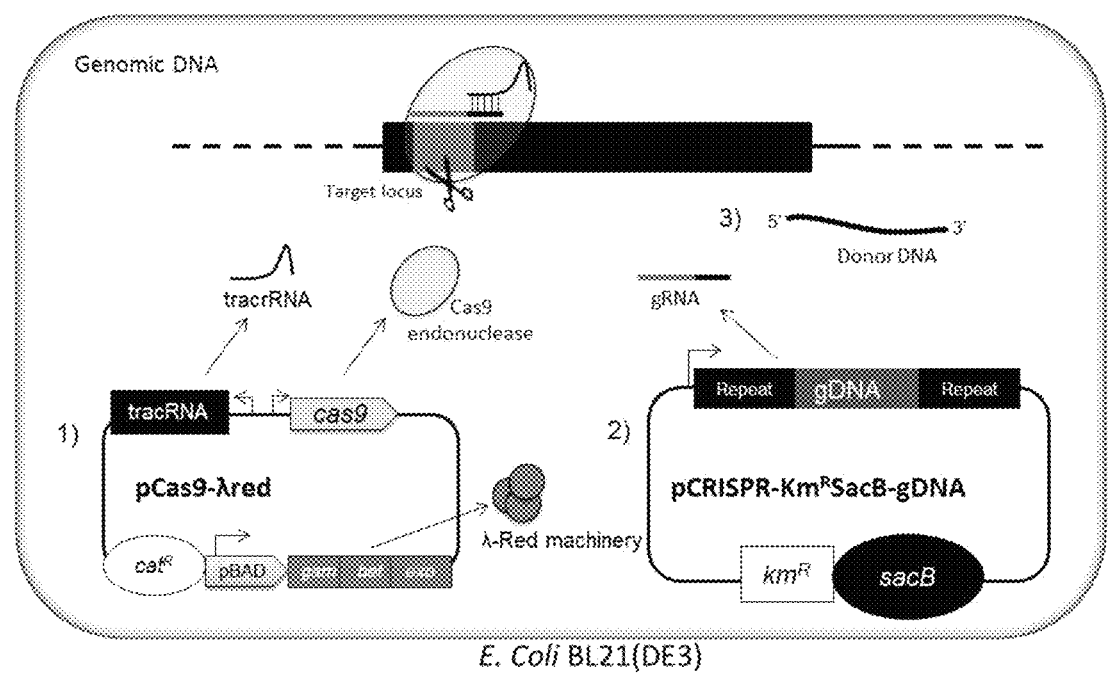

FIG. 13. Overview of the CRISPR/Cas9 genome editing strategy in *Escherichia coli* used in this study.

*E. coli* BL21(DE3) harbors three elements: 1) pCas9-λred plasmid, 2) pCRISPR-Km$^R$SacB-gDNA, and 3) a synthetic, mutation-inducing oligonucleotide (donor DNA). The pCas9-λred plasmid carries the chloramphenicol resistance gene (cat$^R$), the λ red (exo, beta, gam) machinery, the cas9 endonuclease gene, and the tracrRNA. The λ red cassette is under the control of the arabinose-inducible promoter (pBAD), while the cas9 endonuclease and the tracrRNA are under the control of constitutive promoters.

The pCRISPR-Km$^R$SacB-gDNA plasmid carries the kanamycin resistance gene (km$^R$) fused to sacB gene encoding the *Bacillus subtilis* levansucrase and the array "repeat-gDNA-repeat". This array is under the control of a constitutive promoter and expresses the gRNA necessary to guide the Cas9 to the specific genome locus to be cleaved. The third element is a double stranded synthetic oligonucleotide, 120 nucleotides in length complementary to the upstream and downstream regions of the target gene (Donor DNA).

Figure 14:
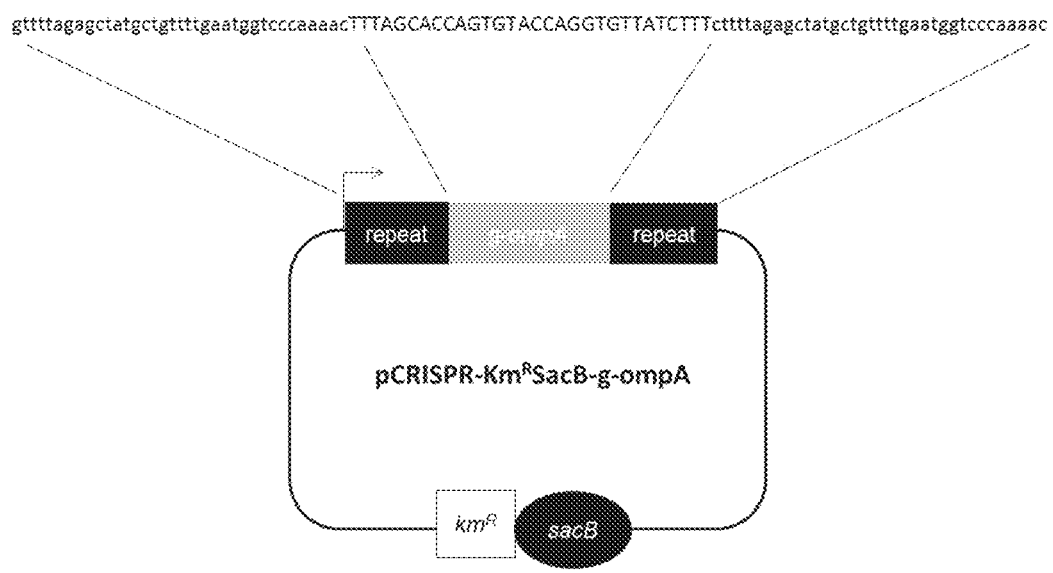

FIG. 14. The pCRISPR-Km$^R$SacB-ompA plasmid used to delete the ompA gene.

The plasmid carries the kanamycin resistance gene (km$^R$) fused to sacB gene and the array repeat-gompA-repeat, whose sequence is reported in the figure (SEQ ID NO:97), which expresses the gRNA to target the ompA gene.

Figure 15:
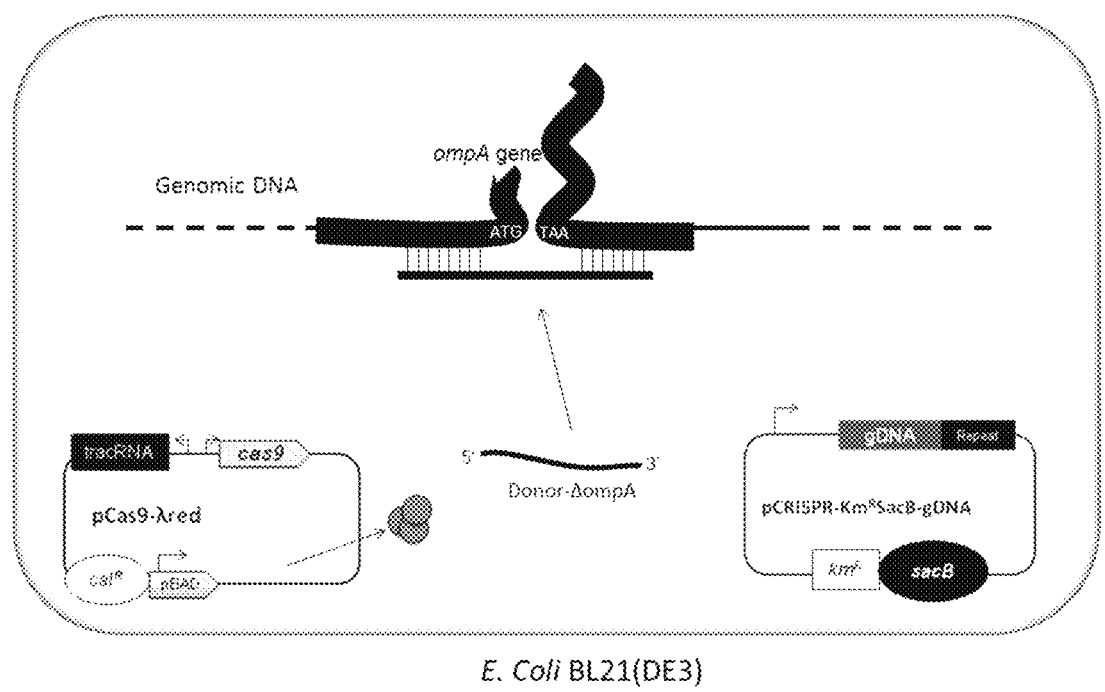

FIG. 15. Schematic representation of ompA gene deletion using pCRISPR-Km$^R$SacB-ompA plasmid.

BL21(DE3)(pCas9-λRed) was co-transformed with pCRISPR-Km$^R$SacB-ompA, targeting the ompA gene, and donor double stranded DNA (Donor-ΔompA). Following the Cas9 cleavage the double strand break is repaired by a double crossing-over of the donor DNA complementary to the upstream and the downstream regions of the ompA gene FIG. 16. PCR analysis on BL21(DE3) ΔompA strain.

PCR primers (OmpA F/OmpA R) were designed to anneal 151 bp upstream and 121 bp downstream of the ompA gene. PCR amplification of BL21(DE3) genome generated a fragment of 1313 bp, while amplification of BL21(DE3) ΔompA with the same primers generated a fragment of 341 bp.

Figure 17:
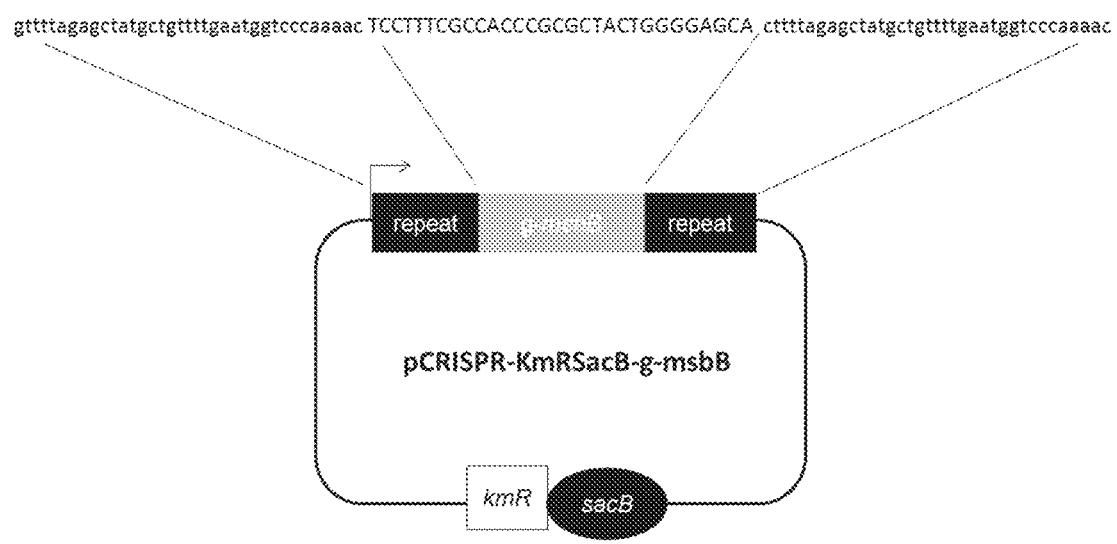

FIG. 17. pCRISPR-Km$^R$SacB-gmsbB plasmid used to delete the msbB gene.

The plasmid carries the kanamycin resistance gene (km$^R$) fused to sacB gene and the array repeat-gmsbB-repeat, whose sequence is reported in the figure (SEQ ID NO:98), which expresses the gRNA to target the msbB gene.

Figure 18:
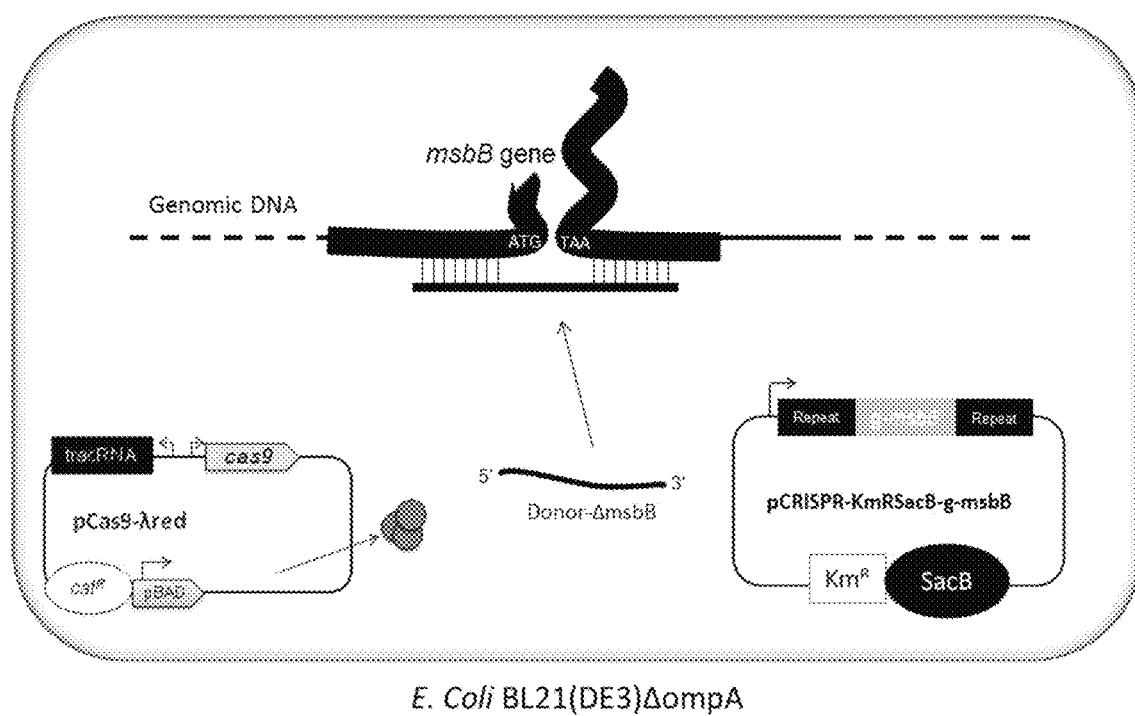

FIG. 18. Schematic representation of msbB gene deletion using pCRISPR-Km$^R$SacB-msbB plasmid.

BL21(DE3)ΔompA(pCas9-λRed) was co-transformed with pCRISPR-Km$^R$SacB-gmsbB, targeting the msbB gene, and donor double stranded DNA (Donor-ΔmsbB). Following the Cas9 cleavage the double strand break is repaired by a double crossing-over of the donor DNA complementary to the upstream and the downstream regions of the msbB gene FIG. 19. PCR analysis on BL21(DE3) ΔompA ΔmsbB strain.

PCR primers (msbB F/msbB R) were designed to anneal 155 bp upstream and 141 bp downstream of the msbB gene. PCR amplification of BL21(DE3) genome generated a fragment of 1267 bp, while amplification of BL21(DE3) ΔompA, ΔmsbB with the same primers generated a fragment of 226 bp.

Figure 20:
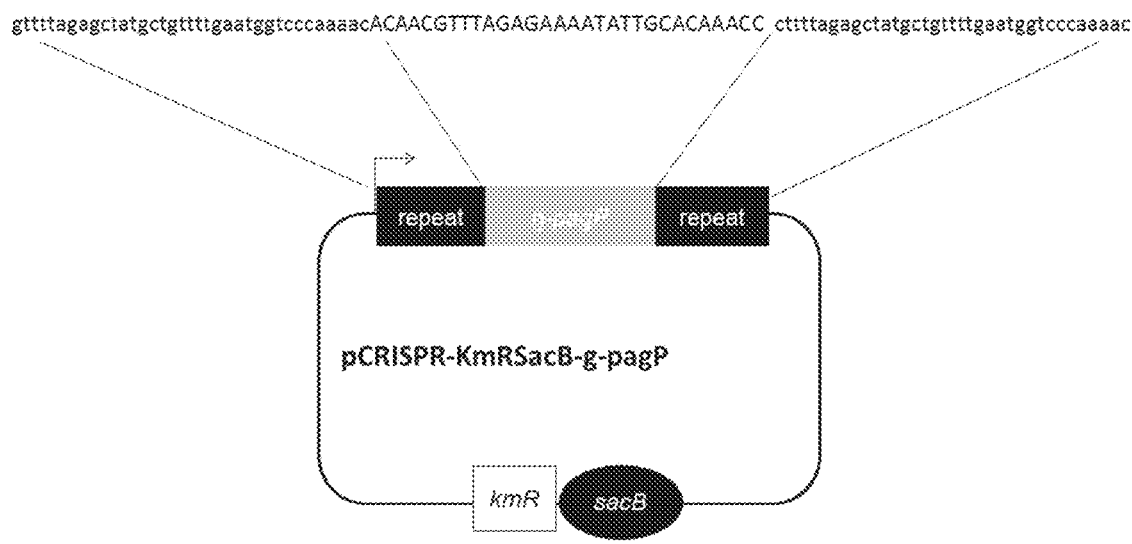

FIG. 20. pCRISPR-Km$^R$SacB-gpagP plasmid used to delete the pagP gene.

The plasmid carries the kanamycin resistance gene (km$^R$) fused to sacB gene and the array repeat-gpagP-repeat, whose sequence is reported in the figure (SEQ ID NO:99), which expresses the gRNA to target the pagP gene.

Figure 21:
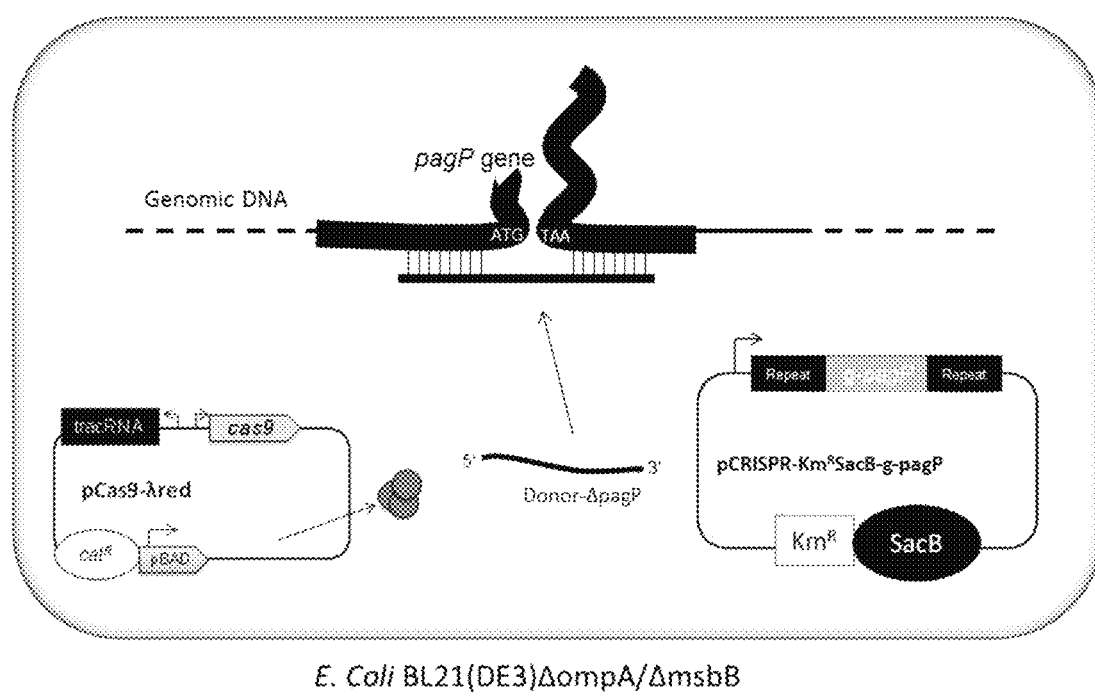

FIG. 21. Schematic representation of pagP gene deletion using pCRISPR-Km$^R$SacB-pagP plasmid.

BL21(DE3)ΔompA/ΔmsbB (pCas9-λRed) was co-transformed with pCRISPR-Km$^R$SacB-gpagP, targeting the pagP gene, and a donor double stranded DNA (Donor-ΔpagP) for the deletion of the whole gene. Following the Cas9 cleavage the double strand break is repaired by a double crossing-over of the donor DNA complementary to the upstream and the downstream regions of the pagP gene FIG. 22. PCR analysis on BL21(DE3) ΔompA ΔmsbB ΔpagP strain.

PCR primers (pagP F/pagP R) were designed to anneal 161 bp upstream and 131 bp downstream of the pagP gene. PCR amplification of BL21(DE3) genome generated a fragment of 862 bp, while amplification of BL21(DE3) ΔompA, ΔmsbB, ΔpagP with the same primers generated a fragment of 292 bp.

Figure 23:
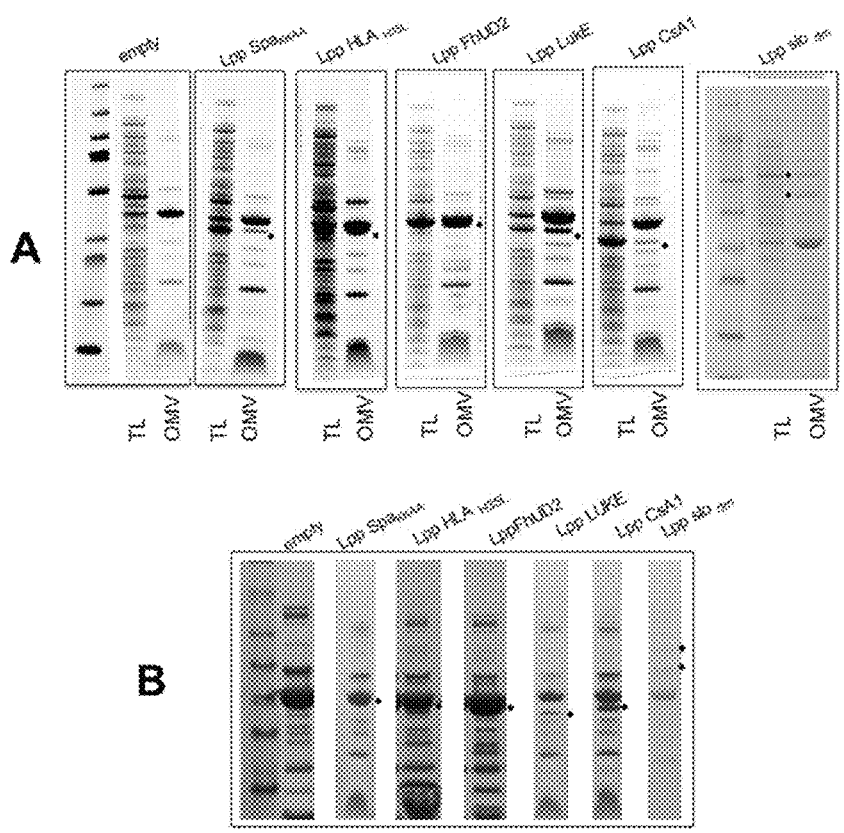

FIG. 23. SDS-PAGE analysis of total lysates and OMVs from BL21(DE3)/ΔompA and BL21(DE3)/ΔompA/ΔmsbB/ΔpagP strains expressing heterologous antigens (A) OMVs purified from BL21(DE3)/ΔompA recombinant strains expressing the lipidated forms of: Spa$_{KKAA}$ (Lpp-Spa$_{KKAA}$), HLA$_{H35L}$ (Lpp-HLA$_{H35L}$), FhuD2 (Lpp-FhuD2), LukE (Lpp-LukE) CsA1 (Lpp-CsA1), and Sloan, (Lpp-slo$_{dm}$), were separated by SDS-PAGE and stained with Coomassie brilliant blue. Dots highlight the bands corresponding to recombinant antigens.

(B) Total cell extracts (TL) and OMVs purified from BL21(DE3)/ΔompA/ΔmsbB/ΔpagP recombinant strains expressing the lipidated antigens: Spa$_{KKAA}$ (Lpp-Spa$_{KKAA}$), HLA$_{H35L}$ (Lpp-HLA$_{H35L}$), FhuD2 (Lpp-FhuD2), LukE (Lpp-LukE) CsA1 (Lpp-CsA1), and Sloan, (Lpp-slo$_{dm}$), were separated by SDS-PAGE and stained with Coomassie brilliant blue. Dots highlight the bands corresponding to recombinant antigens.

Lpp-Spa$_{KKAA}$, Lpp-FhuD2 and Lpp-HLA$_{H35L}$ have a similar molecular mass of the outer membrane proteins OmpF/C and could not be clearly discriminated in the gels.

Figure 24:
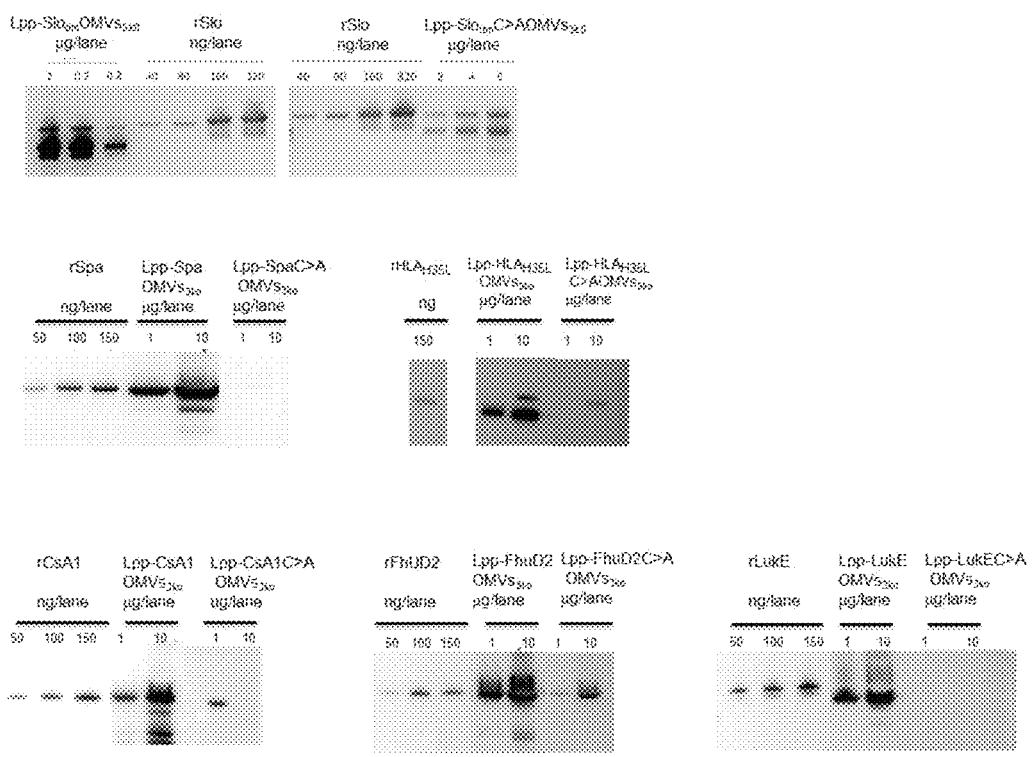

FIG. 24 Semi-quantitative Western Blot analysis of antigen expression in OMVs from strains engineered with the lipidated and non-lipidated versions of the recombinant antigens Different quantities of purified recombinant proteins and OMVs expressing the lipidated (Lpp) and non-lipidated (Lpp C>A) versions of each heterologous antigen were separated by SDS-PAGE and then transferred to nitrocellulose filters. Filters were then incubated with antibodies recognizing the corresponding antigen and subsequently with secondary antibodies conjugated to horseradish peroxidase. Antibody binding was detected using the Super Signal West Pico chemo-luminescent substrate. The amount of each recombinant antigen was estimated by comparing the intensities of bands visualized in OMV preparations with the band intensities of the corresponding purified antigen used as reference.

Figure 25:
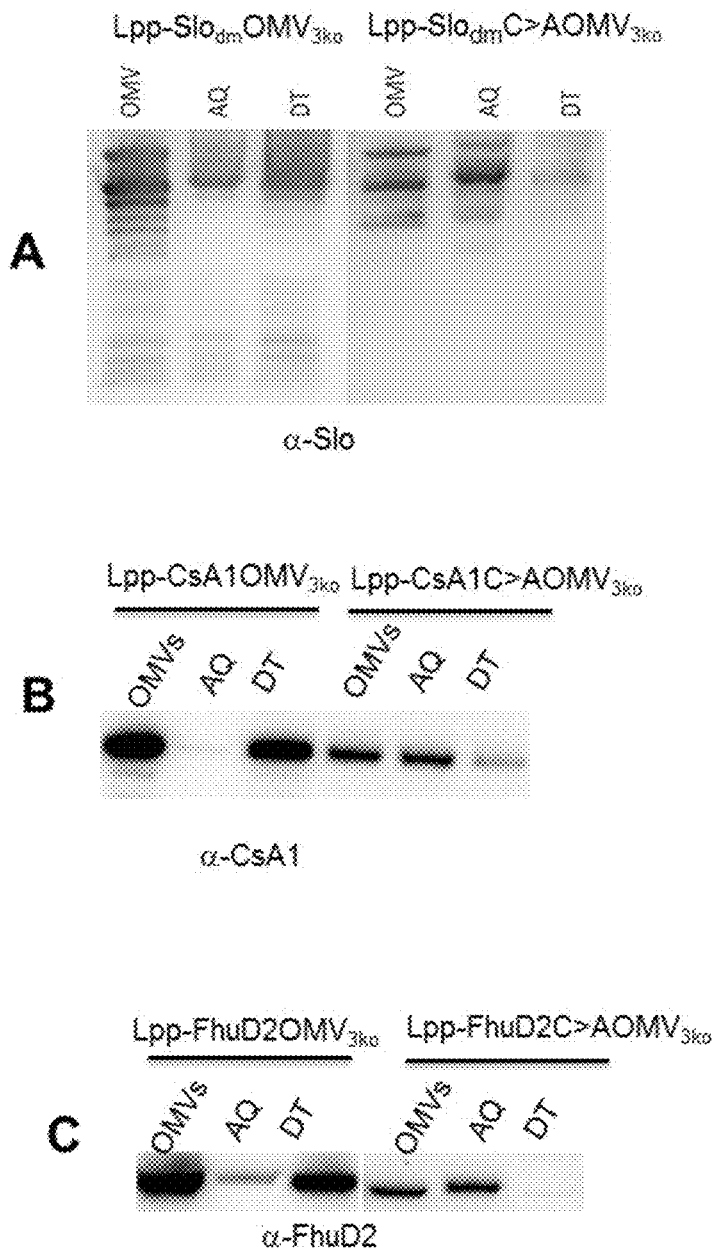

FIG. 25. Analysis of antigen lipidation by Triton X-114 fractionation of OMV proteins.

OMVs (25 μg of proteins) in 50 μl PBS were dissolved by adding 1% Triton X-114 at 4° C. and subsequently aqueous and detergent phases were partitioned by shifting the temperature at 37° C. Unfractionated proteins from intact OMVs, OMV hydrophilic proteins in the aqueous phase (AQ) and OMV hydrophobic proteins in the detergent phase (DT) were precipitated with chloroform/methanol, re-suspended in SDS-PAGE loading buffer and separated by SDS-PAGE. Finally, proteins were transferred onto nitrocellulose filters and the presence of antigens in either the aqueous or detergent phases was detected by Western Blot using antigen specific antibodies. A) OMVs from BL21 (DE3)/ΔompA/ΔmsbB/ΔpagP strains expressing Lpp-Slo$_{dm}$ (Lpp-Slo$_{dm}$OMV$_{3ko}$) and Lpp-SloC>A$_{dm}$ (Lpp-SloC>A$_{dm}$OMV$_{3ko}$); B) OMVs from BL21(DE3)/ΔompA/

ΔmsbB/ΔpagP strains expressing Lpp-CsA1 (Lpp-CsA1OMV$_{3ko}$) and Lpp CsA1C>A (Lpp CsA1C>AOMV$_{3ko}$); C) OMVs from BL21(DE3)/ΔompA/ΔmsbB/ΔpagP strains expressing Lpp-FhuD2 (Lpp-FhuD2OMV$_{3ko}$) and Lpp FhuD2C>A (Lpp FhuD2C>AOMV$_{3ko}$).

Figure 26:
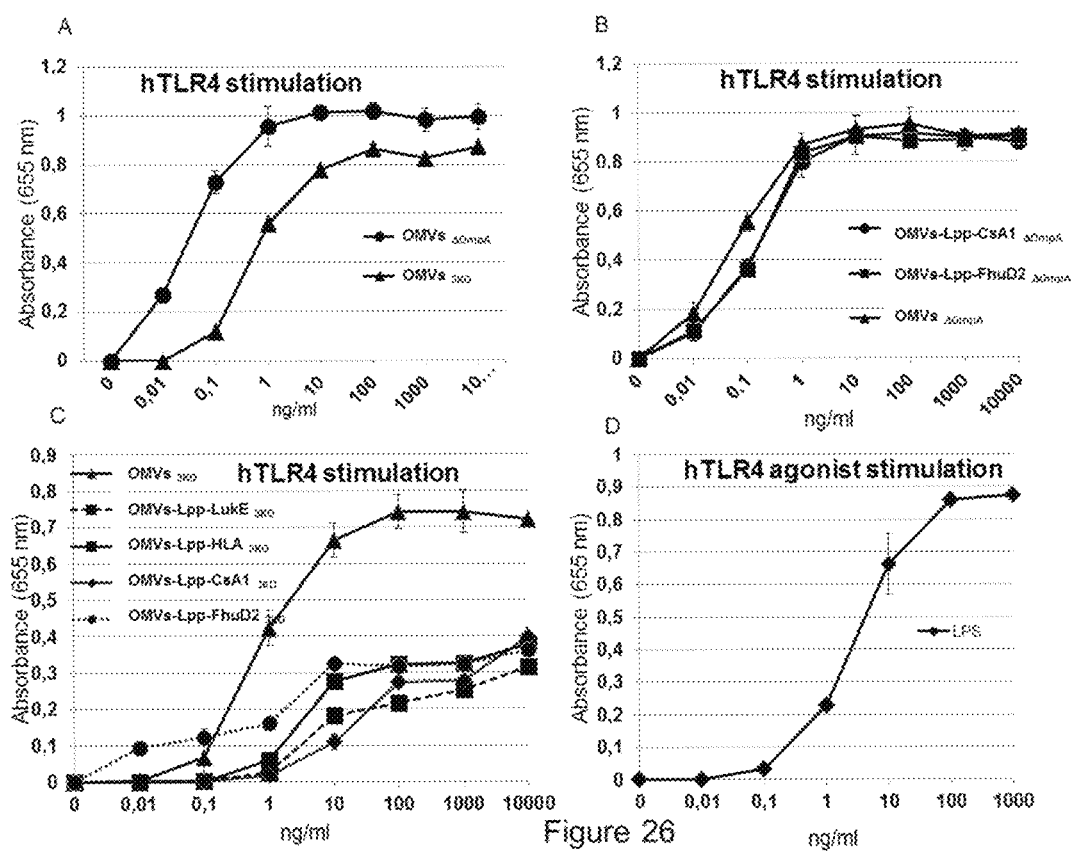

FIG. 26: Stimulation of hTLR4 by OMVs expressing different lipidated antigens purified from BL21(DE3) ΔompA and BL21(DE3) ΔompA/ΔmsbB/ΔpagP strains $5\times10^4$ hTLR4 Hek Blue cells were stimulated with purified LPS or different OMVs preparations at different dilutions and after 16-17 hrs the signaling of hTLR4 was quantified by adding 200 µl of QUANTI Blue and measuring $OD_{655}$ absorbance after 1 hr incubation. For each experiment means of samples run in duplicate and standard deviations are reported.

(A) Stimulation activity of OMVs from *E. coli* BL21 (DE3) ΔompA (OMVs$_{ΔompA}$) and from *E. coli* BL21(DE3) ΔompA/ΔmsbB/ΔpagP (OMVs$_{3ko}$) strains. (B) Stimulation activity of OMVs OMVs-Lpp-FhuD2$_{ΔompA}$ and OMVs-Lpp-CsA1$_{ΔompA}$ from *E. coli* BL21(DE3) ΔompA(pET-Lpp_FhuD2) and *E. coli* BL21(DE3) ΔompA(pET-Lpp_CsA1) strains, respectively. (C) Stimulation activity of OMVs from BL21(DE3) ΔompA/ΔmsbB/ΔpagP(pET-Lpp_FhuD2) (OMVs-Lpp-FhuD2$_{3ko}$), BL21(DE3) ΔompA/ΔmsbB/ΔpagP (pET-Lpp_CsA1) (OMVs-Lpp-CsA1$_{3ko}$), BL21(DE3) ΔompA/ΔmsbB/ΔpagP (pET-Lpp_Hla) (OMVs-Lpp-Hla$_{3ko}$), BL21(DE3) ΔompA/ΔmsbB/ΔpagP (pET-Lpp_LukE) (OMVs-Lpp-LukE$_{3ko}$) and *E. coli* BL21 (DE3) ΔompA/ΔmsbB/ΔpagP (OMVs$_{3ko}$) strains. (D) Stimulation activity of purified LPS used as positive control.

Figure 27:
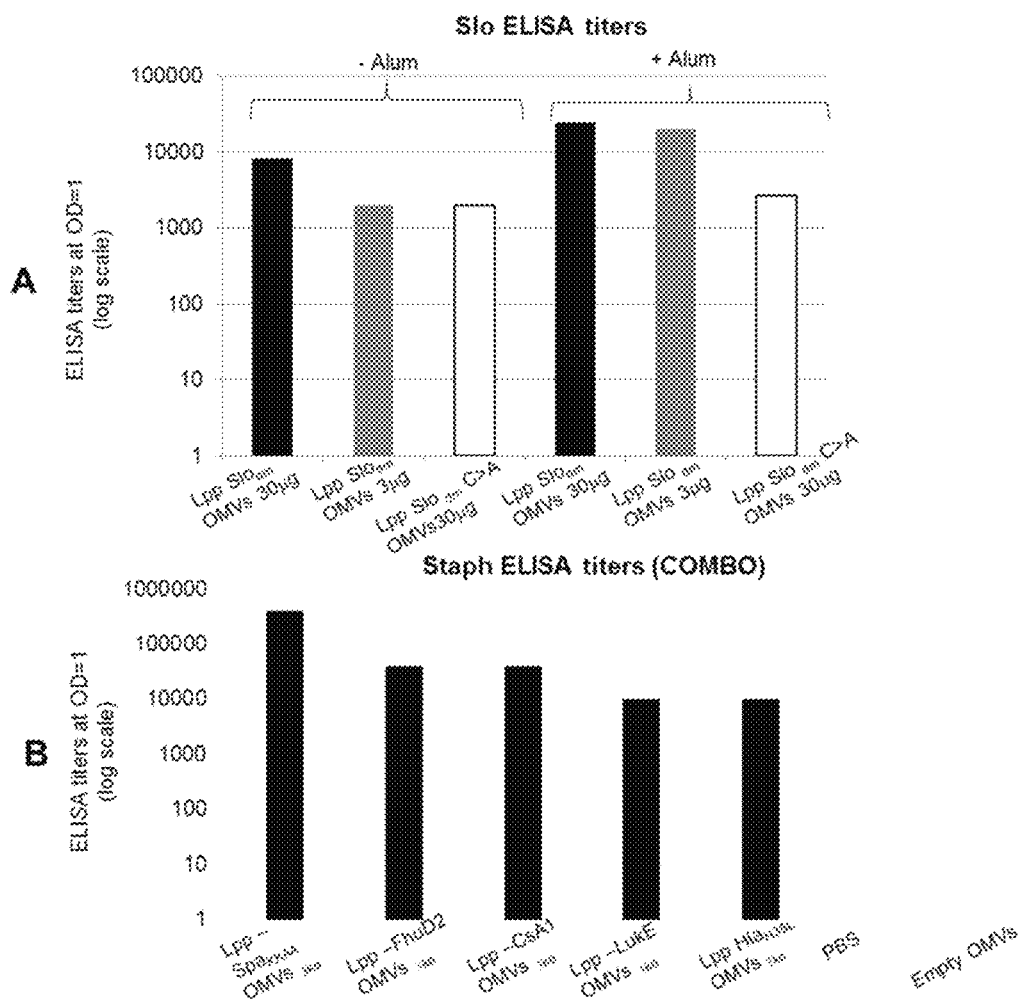

FIG. 27. Analysis of antigen-specific IgG induced in mice immunized with OMVs expressing lipidated antigens.

A) OMVs were purified from BL21(DE3)/ΔompA/ΔmsbB/ΔpagP (pET-Lpp_slo$_{dm}$) and BL21(DE3)/ΔompA/ΔmsbB/ΔpagP (pET-Lpp-slo$_{dm}$C>A) strains and used to immunize mice at two different amounts (30 µg, 3 µg) in the presence or absence of Alum as adjuvant. After 3 doses sera were collected and pooled and Slo-specific IgG titers were measured by ELISA. Anti-mouse IgGs conjugated to alkaline phosphatase were used as secondary antibody. ELISA titers at $OD_{405}=1$ are shown for each group.

B) OMVs were purified from BL21(DE3)/ΔompA/ΔmsbB/ΔpagP (pET-Lpp_spa$_{KKAA}$), BL21(DE3)/ΔompA/ΔmsbB/ΔpagP (pET-Lpp_fhuD2), BL21(DE3)/ΔompA/ΔmsbB/ΔpagP (pET-Lpp_CsA1), BL21 (DE3)/ΔompA/ΔmsbB/ΔpagP pET-Lpp_HLA$_{H35L}$) and BL21(DE3)/ΔompA/ΔmsbB/ΔpagP (pET-Lpp_lukE) strains and 20 µg of each preparation were pooled together and used to immunize mice. After 3 doses sera were collected and pooled and antigen-specific IgG titers were measured by ELISA. Anti-mouse IgGs conjugated to alkaline phosphatase were used as secondary antibody. As a control, antibody titers from mice immunized with "empty" OMVs or PBS were tested. Plates were coated with each corresponding purified antigen. ELISA titers at $OD_{405}=1$ are shown for each antigen. ELISA titers at $OD_{405}=1$ are shown for each group.

Figure 28:
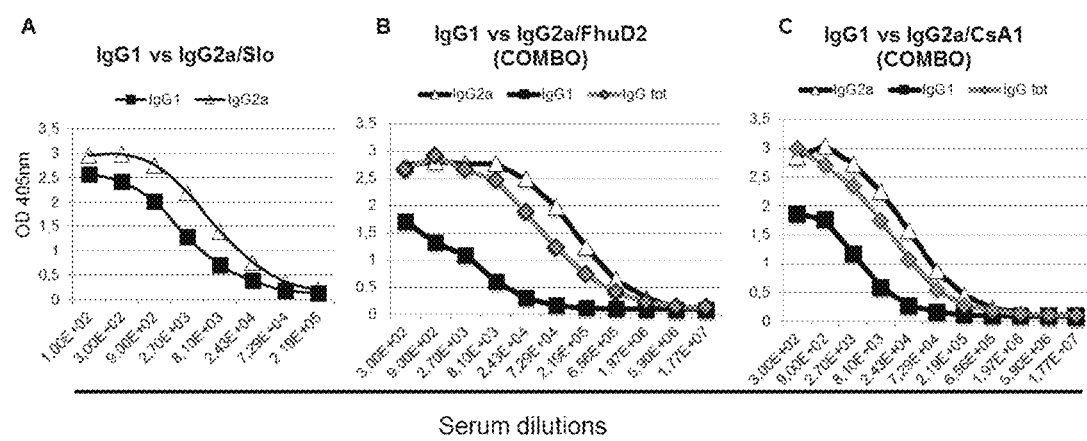

FIG. 28. Isotype analysis of antibodies elicited in mice immunized with OMVs expressing lipidated Slo$_{dm}$ antigen and lipidated *S. aureus* antigens (COMBO).

A) Lpp-Slo$_{dm}$OMVs$_{3ko}$ (30 µg) were used to immunize mice and after 3 doses sera were collected and pooled. IgG1 and IgG2a were measured by ELISA using plates coated with purified Slo$_{dm}$ protein and anti-IgG1 and anti-IgG2a mouse specific antibodies. B-C) OMVs were purified from BL21(DE3)/ΔompA/ΔmsbB/ΔpagP(pET-Lpp_fhuD2), BL21(DE3)/ΔompA/ΔmsbB/ΔpagP(pET-Lpp_CsA1), BL21(DE3)/ΔompA/ΔmsbB/ΔpagP(pET-Lpp_HLA$_{H35L}$), BL21(DE3)/ΔompA/ΔmsbB/ΔpagP(pET-Lpp_lukE) strains and 20 µg of each preparation were pooled together and used to immunize mice. After 3 doses sera were collected and pooled. IgG1 and IgG2a and total IgG specific for FhuD2 (B) and CsA1 (C) were measured by ELISA using plates coated with the corresponding purified protein and anti-IgG1, anti-IgG2a and anti-total IgG mouse specific antibodies.

DETAILED DESCRIPTION OF THE INVENTION

5.1 Example 1—Cloning of Heterologous Antigens as Lipoproteins

In order to express the GAS antigen Slo$_{dm}$ and the five Staph antigens HLA$_{H35L}$, LukE, FhuD2, CsA1 and Spa$_{KKAA}$ in the membrane compartment of *E. coli* OMVs as lipoproteins, the *E. coli* Lpp leader sequence was N-terminal fused to the proteins of interest. Lpp is an endogenous *E. coli* lipoprotein which carries a signal peptide characterized by the specific conserved sequence Leu-(Ala/Ser)-(Gly-Ala)-Cys at its C-terminal region in which the cysteine residue is lipidated. The first construct to be generated was pET-lpp-Slo$_{dm}$, in which the slo$_{dm}$ gene was fused to the lpp leader sequence, and subsequently this plasmid was used as a template to generate all other constructs.

Figure 1:
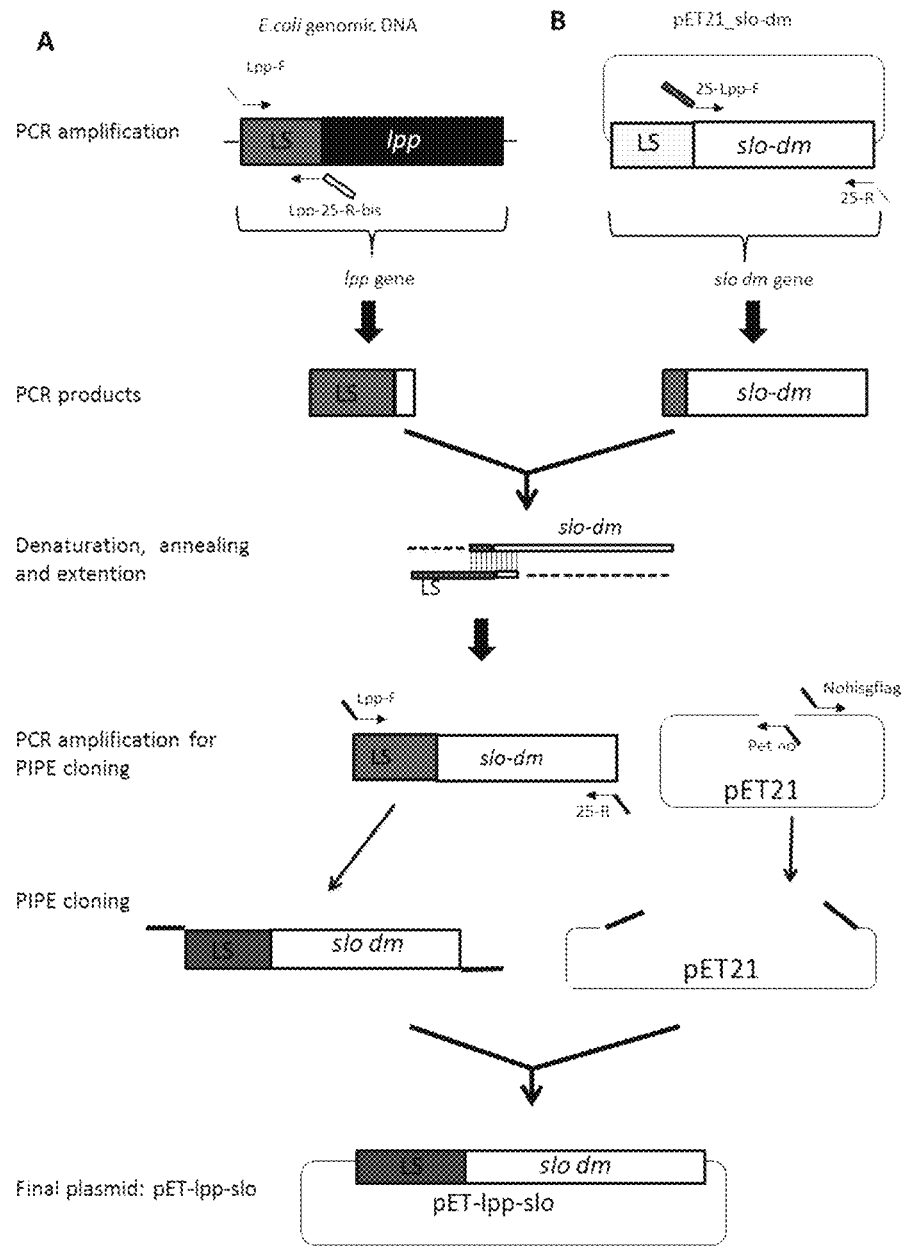
FIG. 1. Cloning strategy used to fuse the GAS antigen Slot$_{dm}$ to the leader sequence of the lipoprotein Lpp To generate pET-lpp-slo$_{dm}$ plasmid the Lpp Leader Sequence was PCR amplified from E. coli BL21DE3 genome using primers Lpp-F and Lpp-R-25bis (A) and slo$_{dm}$ gene was PCR amplified from pET21-slo$_{dm}$ plasmid using primers 25-Lpp-F and 25-R (B). The two PCR fragments generated contain region of overlap due to the design of the primers Lpp-25_R-bis and 25-lpp-F which carry a tail containing the first 14 nucleotides of the slo$_{dm}$ gene (white) and the last 12 nucleotides of the Lpp leader sequence (grey), respectively. In a second round of PCR the two fragments were mixed together and subjected to denaturing and annealing steps, thus allowing the annealing of the two fragments in the overlapping region. In presence of a DNA polymerase each overlapping end serves as primer for the polymerase to synthetize the complementary strand obtaining a complete long fragment. The jointed fragment was subsequently amplified using external primers Lpp-F/25-R. The product was then cloned into pET21 plasmid amplified with petno/nohisflag primers using the polymerase incomplete primer extension (PIPE) cloning method.

The strategy used to insert the slo$_{dm}$ gene fused to lpp leader sequence into pET plasmid is schematized in FIG. 1. The coding sequence of Lpp leader sequence was PCR amplified from *E. coli* BL21(DE3) genome using primers Lpp-F/Lpp-25-R-bis. In parallel, the slo$_{dm}$ gene, deprived of its natural leader peptide, was PCR amplified from pET21-slo$_{dm}$ plasmid (Fantappiè et al., 2014) using primers 25-lpp-F/25-R. The pET21-slo$_{dm}$ plasmid was previously generated by cloning the slo$_{dm}$ gene into pET21 plasmid (Fantappiè et al, 2014). Slo$_{dm}$ is a mutated form of Slo carrying 2 point mutations which inactivate the enzymatic activity of the antigen without affecting its immunogenic properties (Chiarot et al, 2013). The two PCR fragments generated contains region of overlap due to the design of the primers Lpp-25_R-bis and 25-lpp-F which carry a tail containing the first 14 nucleotides of the slo$_{dm}$ gene and the last 12 nucleotides of the lpp leader sequence, respectively. In a second round of PCR the two fragments were mixed together and subjected to denaturing and annealing steps, thus allowing the fusion of the two fragments in the overlapping region. The jointed fragment was subsequently amplified using the external primers Lpp-F/25-R. The product was then cloned into pET21 plasmid amplified with petno/nohisflag primers using the polymerase incomplete primer extension (PIPE) cloning method (Klock H. E. and Lesley S. A (2009) Methods Mol. Biol. 498, 91-103), to obtain pET-lpp-Slo$_{dm}$ plasmid. The correctness of the cloning was verified by sequence analysis (nucleic acid sequence: SEQ ID NO:1; deduced amino acid sequence: SEQ ID NO:20).

Figure 2:
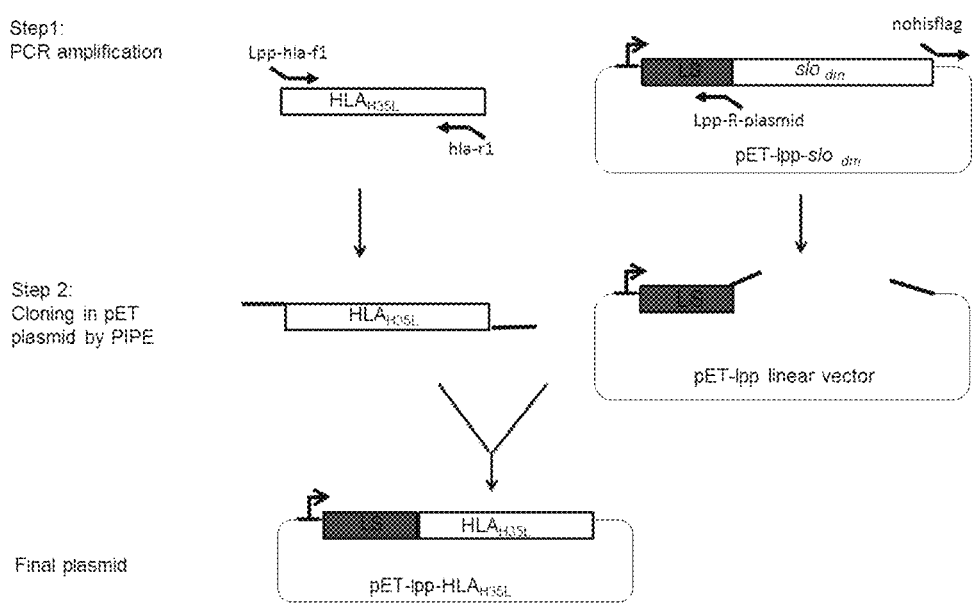
FIG. 2. Cloning strategy used to fuse the S. aureus antigen Hla$_{H35L}$ to the leader sequence of the lipoprotein Lpp The HLA$_{H35L}$ open reading frame was chemically synthesized and then amplified by PCR using primers lpp-hla-f1/hla-r1. These primers generated extremities complementary to the linearized pET-lpp-slo$_{dm}$ deprived of the slo$_{dm}$ sequence but carrying the Lpp leader sequence. Such vector was obtained by PCR amplification with the divergent primers Lpp-R-plasmid/nohisflag. PCR products (vector plus insert) were then mixed together and used to transform E. coli strain generating plasmid pET-lpp-HLA$_{H35L}$.

To express the Hla$_{H35L}$ antigen in the membrane compartment of *E. coli* OMVs as lipoprotein, it was fused to the leader sequence of *E. coli* Lpp (FIG. 2). The gene was chemically synthetized (Genart-Invitrogen) (nucleic acid sequence: SEQ ID NO:3; deduced amino acid sequence: SEQ ID NO:22) and then amplified by PCR using primers lpp-hla-f1/hla-r1. These primers were designed to generate extremities complementary to the vector backbone pET-lpp-slo$_{dm}$ amplified using the divergent primers Lpp-R-plasmid/ nohisflag. The PCR products (vector plus insert) were then mixed together and used to transform *E. coli* generating plasmids pET-lpp-Hla$_{H35L}$. The correctness of the cloning was verified by sequence analysis (nucleic acid sequence: SEQ ID NO:4; deduced amino acid sequence: SEQ ID NO:23).

Figure 3:
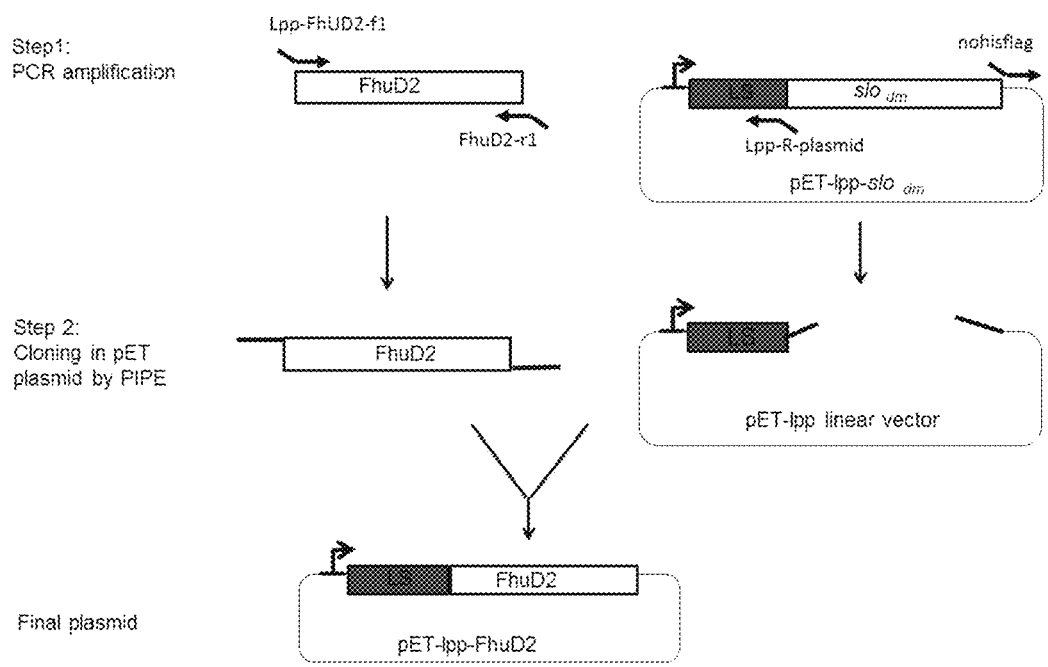
FIG. 3. Cloning strategy used to fuse the S. aureus antigen FhuD2 to the leader sequence of the lipoprotein Lpp The fhuD2 gene was chemically synthesized and then amplified by PCR using primers lpp-FhuD2-f1/FhuD2-r1. These primers generated extremities complementary to the vector backbone pET-lpp-slo$_{dm}$. The vector was linearized by PCR amplification with the divergent primers Lpp-R-plasmid/nohisflag. PCR products (vector plus insert) were then mixed together and used to transform *E. coli* strain generating plasmid pET-lpp-FhuD2.

To express the FhuD2 antigen in the membrane compartment of *E. coli* OMVs as lipoprotein, it was fused to the leader sequence of *E. coli* Lpp (FIG. 3). The gene was chemically synthetized (Genart-Invitrogen) (nucleic acid sequence SEQ ID NO:6; deduced amino acid sequence: SEQ ID NO:25) and then amplified using primers lpp-FhuD2-f1/FhuD2-r1. These primers were designed to generate extremities complementary to the vector backbone pET-lpp-slo$_{dm}$ amplified using the divergent primers Lpp-R-plasmid/nohisflag. The PCR products (vector plus insert) were then mixed together and used to transform *E. coli* generating plasmid pET-lpp-FhuD2. The correctness of the cloning was verified by sequence analysis (SEQ ID NO:7).

Figure 4:
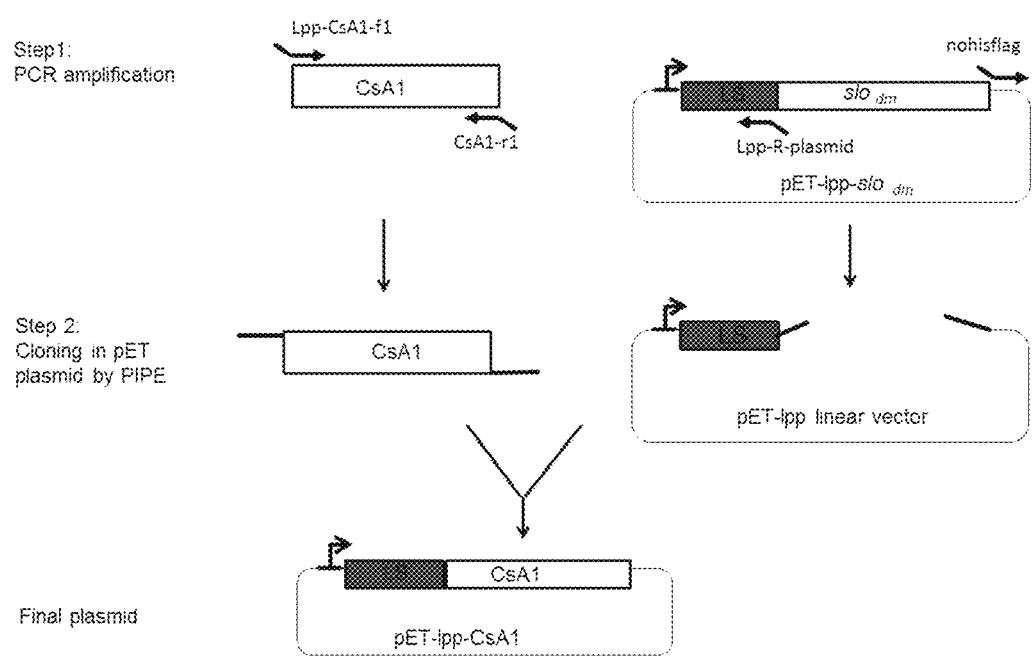
FIG. 4. Cloning strategy used to fuse the *S. aureus* antigen CsA1 to the leader sequence of the lipoprotein Lpp The csA1 gene was chemically synthesized and then amplified by PCR using primers lpp-CsA1-f1/CsA1-r1. These primers generated extremities complementary to the vector backbone pET-lpp-slo$_{dm}$. The vector was linearized by PCR amplification with the divergent primers Lpp-R-plasmid/nohisflag. PCR products (vector plus insert) were then mixed together and used to transform *E. coli* strain generating plasmid pET-lpp-CsA1.

To express the CasA1 antigen in the membrane compartment of *E. coli* OMVs as lipoprotein, it was fused to the leader sequence of *E. coli* Lpp (FIG. 4). The gene was chemically synthetized (Genart-Invitrogen) (nucleic acid sequence: SEQ ID NO:9; deduced amino acid sequence: SEQ ID NO:28) and then amplified by PCR using primers lpp-CsA1-f1/CsA1-r1. These primers were designed to generate extremities complementary to the vector backbone pET-lpp-slo$_{dm}$ amplified using the divergent primers Lpp-R-plasmid/nohisflag. The PCR products (vector plus insert) were then mixed together and used to transform *E. coli* generating plasmid pET-lpp-CsA1. The correctness of the cloning was verified by sequence analysis (nucleic acid sequence: SEQ ID NO:10; deduced amino acid sequence: SEQ ID NO:29).

Figure 5:
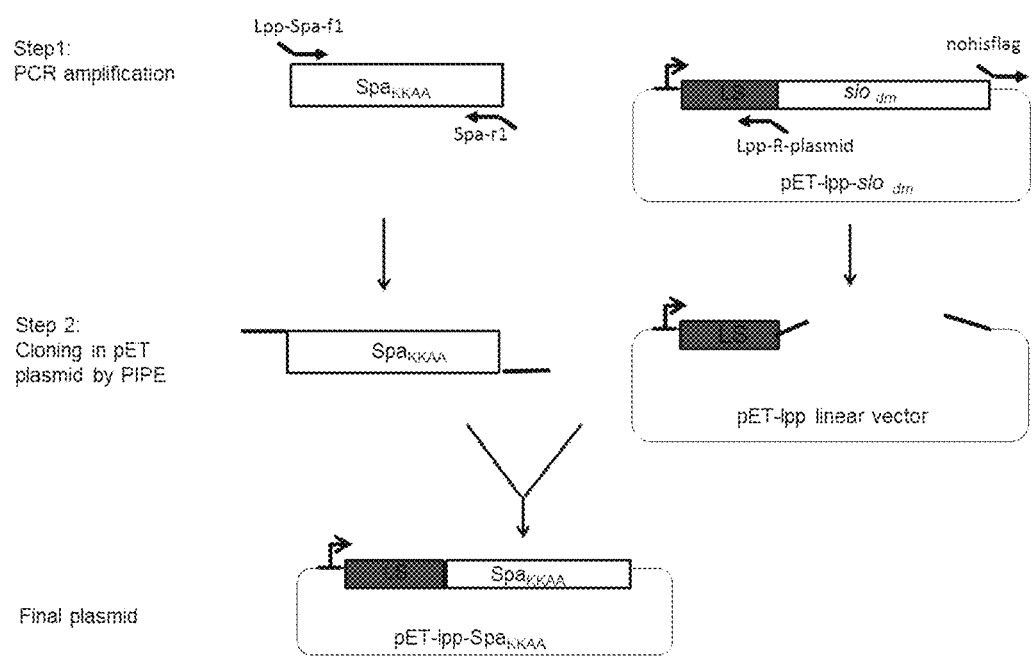
FIG. 5. Cloning strategy used to fuse the *S. aureus* antigen Spa$_{KKAA}$ to the leader sequence of the lipoprotein Lpp The spa$_{KKAA}$ gene was chemically synthesized and then amplified by PCR using primers lpp-Spa-f1/Spa-r1. These primers generated extremities complementary to the vector backbone pET-lpp-slo$_{dm}$. The vector was linearized by PCR amplification with the divergent primers Lpp-R-plasmid/nohisflag. PCR products (vector plus insert) were then mixed together and used to transform *E. coli* strain generating plasmid pET-lpp-Spa$_{KKAA}$.

To express the Spa$_{KKAA}$ antigen in the membrane compartment of *E. coli* OMVs as lipoprotein, it was fused to the leader sequence of *E. coli* Lpp (FIG. 5). The gene was chemically synthetized (Genart-Invitrogen) (nucleic acid sequence: SEQ ID NO:12; amino acid sequence: SEQ ID NO:31) and then amplified by PCR using primers lpp-Spa1-f1/Spa-r1. These primers were designed to generate extremities complementary to the vector backbone pET-lpp-slo$_{dm}$ amplified using the divergent primers Lpp-R-plasmid/nohisflag. The PCR products (vector plus insert) were then mixed together and used to transform *E. coli* generating plasmid pET-lpp-Spa$_{KKAA}$. The correctness of the cloning was verified by sequence analysis (nucleic acid sequence: SEQ ID NO:13; deduced amino acid sequence: SEQ ID NO:32).

Figure 6:
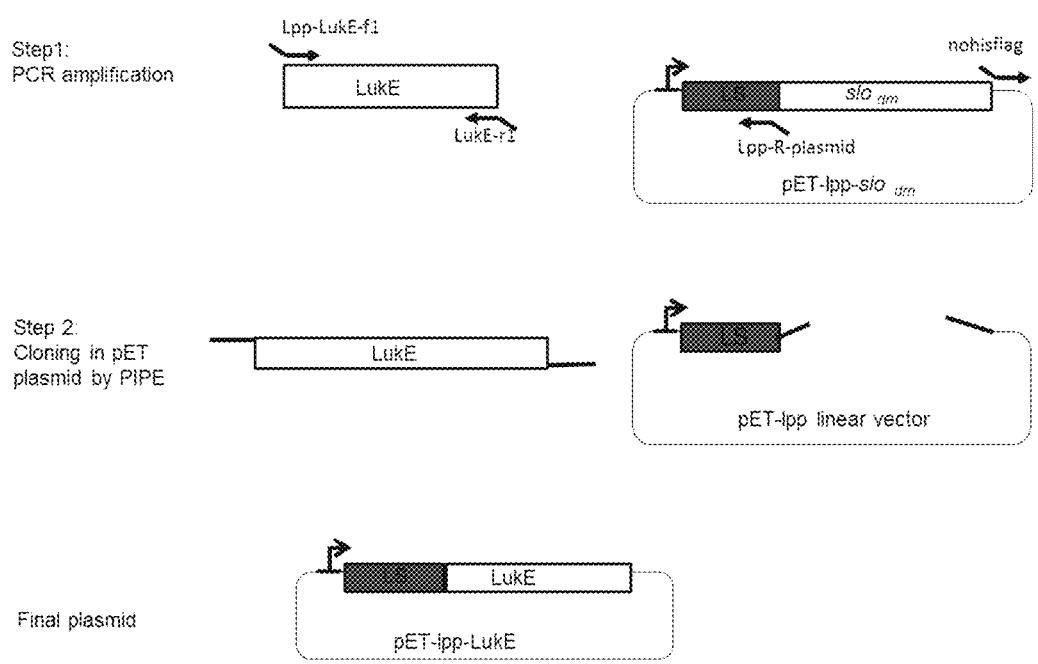
FIG. 6. Cloning strategy used to fuse the *S. aureus* antigen LukE to the leader sequence of the lipoprotein Lpp The lukE gene was chemically synthesized and then amplified by PCR using primers lpp-LukE-f1/LukE-r1. These primers generated extremities complementary to the vector backbone pET-lpp-slo$_{dm}$. The vector was linearized by PCR amplification with the divergent primers Lpp-R-plasmid/nohisflag. PCR products (vector plus insert) were then mixed together and used to transform *E. coli* strain generating plasmid pET-lpp-LukE.

Finally, to express the LukE antigen in the membrane compartment of *E. coli* OMVs as lipoprotein, it was fused to the leader sequence of *E. coli* Lpp (FIG. 6). The gene was chemically synthetized from Genart-Invitrogen as DNA string (nucleic acid sequence: SEQ ID NO:15; deduced amino acid sequence: SEQ ID NO:34). And then amplified using primers lpp-LukE-f1/LukE-r1. These primers were designed to generate extremities complementary to the vector backbone pET-lpp-slo$_{dm}$ amplified using the divergent primers Lpp-R-plasmid/nohisflag. The PCR products (vector plus insert) were then mixed together and used to transform *E. coli* generating plasmid pET-lpp-LukE. The correctness of the cloning was verified by sequence analysis (nucleic acid sequence: SEQ ID NO:16; deduced amino acid sequence: SEQ ID NO:35).

5.2 Example 2—Cloning of Heterologous Antigens as Periplasmic, Non-Lipidated Lipoproteins The sequence "LAGC" at the C-terminal region of the Lpp leader sequence, known as "lipobox", mediates the acylation of lipoprotein, with the Cysteine residue serving as acceptor of the three fatty acid chains. The Cysteine residue, which represents the first amino acid of mature lipoprotein, is essential for the acylation process. Replacement of the Cysteine with other amino acids still allows lipoprotein to cross the inner membrane and reach the periplasm but prevent the attachment of the lipid moieties.

Based on the above, non-lipidated versions of the heterologous antigens were generated by replacing the Cysteine of the lpp lipobox (LAG<u>C</u>) with Alanine using a PCR-based site direct mutagenesis approach.

Figure 7:
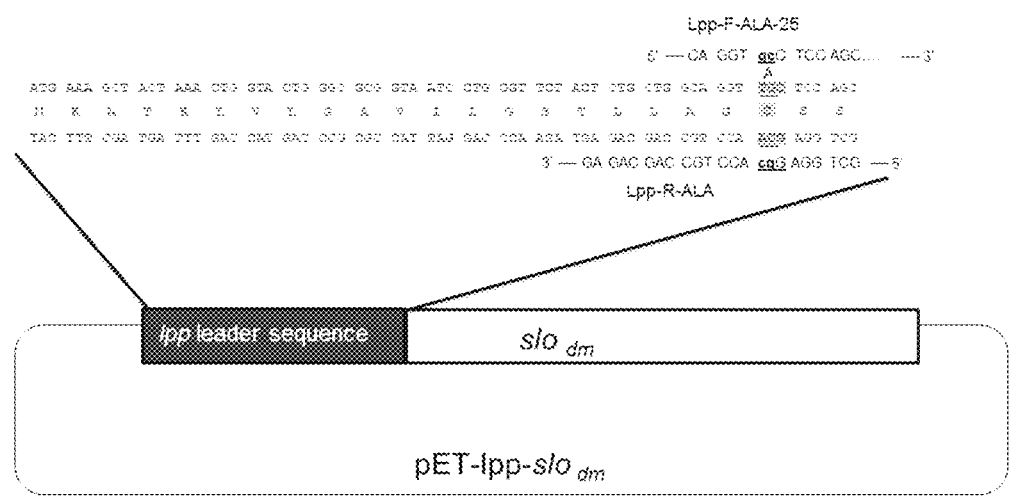
FIG. 7. Strategy used to mutagenize the cysteine residue in the lipobox of the Lpp leader sequence of pET-lpp-slo$_{dm}$ plasmid The pET-lpp-slo$_{dm}$ plasmid was PCR amplified using primers lpp-R-ALA/lpp-F-ALA25 (SEQ ID NOs:84-85). The primers were designed to anneal to the Lpp leader sequence (coding sequence SEQ ID NO:86; amino acid sequence SEQ ID NO:100) and carry a GC mismatch allowing the substitution of the cysteine (TGC codon) with an alanine (GCC codon) residue. The primers carry partially complementary 5' tails which, when annealed, reconstitute the circularized plasmid with the C>A substitution. PCR product was then used to transform *E. coli* cells generating plasmids pET-lpp-Slo-C>A.

To generate pET-lpp-slo$_{dm}$C>A construct the PIPE method was used, as schematized in FIG. 7. Briefly, the plasmid pET-lpp-slo$_{dm}$ was PCR amplified using primers lpp-R-ALA/lpp-F-ALA25. The primers anneal to the Lpp leader sequence and carry a mismatch allowing the substitution of the cysteine with an alanine residue. The primers also carry partially complementary 5' tails which, when annealed, reconstitute the circularized plasmid with the C>A substitution. The PCR product was then used to transform *E. coli* HK-100 cells generating plasmids pET-lpp-slo-C>A. The correctness of the cloning was verified by sequence analysis (nucleic acid sequence: SEQ ID NO:2; deduced amino acid sequence: SEQ ID NO:21).

Figure 8:
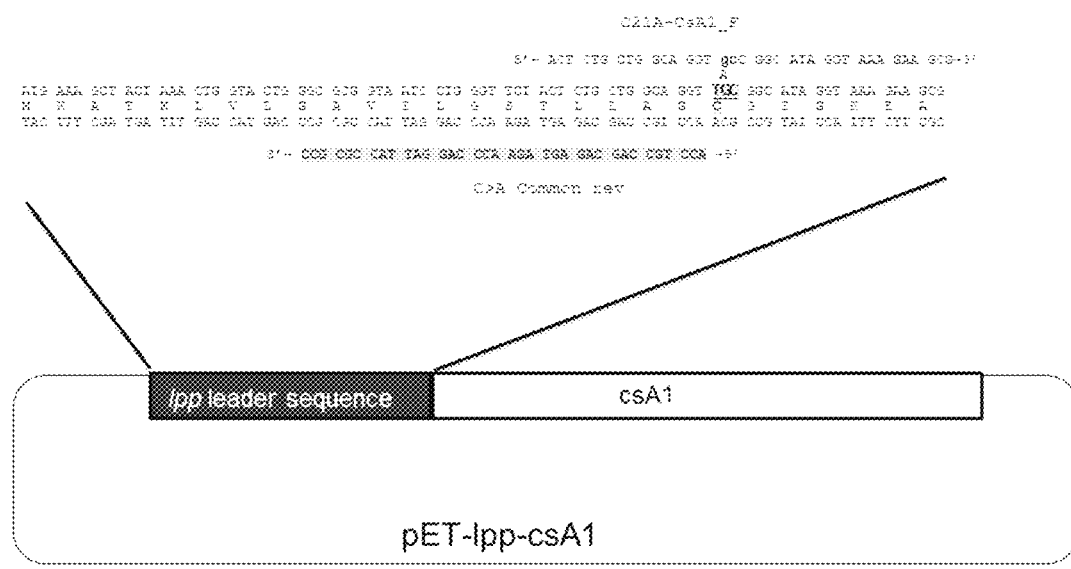
FIG. 8. Strategy used to mutagenize the cysteine residue in the lipobox of the Lpp leader sequence of pET-lpp-CsA1 plasmid To generate pET-lpp-CsA1-C>A plasmid two primers were designed, a reverse primer annealing upstream of the Cysteine codon to be changed (C>A common rev, SEQ ID NO:87) and a "mutagenic" forward primers (C21A-CsA1_F, SEQ ID NO:88) carrying a two nucleotide "GC" mismatch which converts the TGC Cysteine codon into GCC Alanine codon.

To generate the plasmid constructs: pET-lpp-csA1-C>A (FIG. 8), pET-lpp-fhuD2-C>A, (FIG. 9), pET-lpp-spa$_{KKAA}$-C>A (FIG. 10), pET-lpp-lukE-C>A (FIG. 11) and pET-lpp-hla$_{H35L}$-C>A (FIG. 12), five couples of primers were designed constituted by a reverse primer, which was in common to all couples and annealed upstream of the Cysteine codon to be changed (C>A common rev) and a "mutagenic", antigen specific forward primer (C21A-"antigen"_F) carrying a two nucleotide "GC" mismatch and converting the TGC Cysteine codon to a GCC Alanine codon. The couple of primers also carried partially complementary 5' tails, allowing the linear PCR product to recombine when transformed in *E. coli* and to reconstitute the circularized plasmid with the C>A substitution. The correctness of the cloning was verified by sequence analysis (lpp-hla$_{H35L}$-C>A: SEQ ID NO:5 and SEQ ID NO:24 nucleic acid and amino acid sequences, respectively; lpp-fhuD2-C>A: SEQ ID NO:8 and SEQ ID NO:27 nucleic acid and amino acid sequences, respectively; lpp-CsA1-C>A: SEQ ID NO:11 and SEQ ID NO:30 nucleic acid and amino acid sequences, respectively; lpp-spa$_{KKAA}$-C>A: SEQ ID NO:14 and SEQ ID NO:33 nucleic acid and amino acid sequences, respectively; lpp-lukE-C>A: SEQ ID NO:17 and SEQ ID NO:36 nucleic acid and amino acid sequences, respectively)

5.3 Example 3—Generation of *E. coli* BL21(DE3) ΔompA Strain and *E. coli* BL21(DE3 ΔompA/ΔmsbB/ΔpagP Strain Having generated the recombinant plasmids encoding the lipidated and non-lipidated version of the selected heterologous antigens, two *E. coli* BL21(DE3) derivatives were created to subsequently prepare OMVs loaded with each antigen. Different strains can be used to produce OMVs. In this example the use of two hyper-vesiculating strains, one carrying the deletion of the ompA gene and the other carrying the deletion of the ompA, msbB, pagP genes is described.

A number of methods have been reported to create gene knock-outs and gene knock-ins in *E. coli*. The most popular ones make use of the λ phage recombination system ("recombineering") that enormously enhances the double cross-over events between the chromosomal DNA and the transforming "donor DNA" designed to create the mutation (Murphy K C (1998) J. Bacteriol. 180, 2063). The donor DNA can be either synthetic single/double strand DNA or PCR-derived DNA (Ju et al., (2000) Proc. Natl. Acad. Sci. USA, 97, 5978; Ellis et al., (2001) Proc. Natl. Acad. Sci. USA, 98, 6742). More recently, a combination of "recombineering" with CRISPR/Cas genome editing strategy has been shown to generate mutants in E. coli with high efficiency (Jiang et al. (2013) Nat. Biotechnol. 31, 233).

The generation of the two strains E. coli BL21 (DE3) ΔompA and E. coli BL21 (DE3)ΔompA/ΔmsbB/ΔpagP was performed using a CRISPR/Cas genome editing strategy specifically optimized for this work and schematically depicted in FIG. 13. In essence, the strategy makes use of three main elements: pCas9-λ red, pCRISPR-Km$^R$SacB-gDNA, and the synthetic, mutation-inducing (mutagenic) oligonucleotide. The pCas9-λred plasmid carries (i) the λ red (exo, beta, gam) cassette, (Derbise A., et al, 2003, J. A. Mosberg et al. 2010), (ii) the chloramphenicol resistance gene (cat$^R$), (iii) the gene encoding the Cas9 nuclease, and (iiii) the tracrRNA (trans-activating crRNA). The cas9 gene and the tracrRNA coding sequence are under the control of constitutive promoters while the λ red gene cassette is transcribed from the arabinose-inducible promoter (SEQ ID NO:18). The pCRISPR-Km$^R$SacB-gDNA plasmid derives from pCRISPR (Jiang W. et al, (2013) Nat. Biotechnol. 31, 233) in which the kanamycin resistance gene (km') has been fused to sacB gene encoding the Bacillus subtilis levansucrase. The sequence of Kanamycin-sacB cassette is reported in SEQ ID NO:19. SacB is toxic in E. coli if grown in media containing 5% sucrose (Gay P et al., (1985) J. Bacteriol. 164, 918). This property can be conveniently exploited to remove the pCRISPR-Km$^R$SacB-gDNA plasmid after a specific mutation has been introduced. Finally, pCRISPR-Km$^R$-SacB-gDNA carries the synthetic DNA fragment (gDNA) encoding the guide RNA necessary to drive the Cas9-dependent double stranded break at the desired site of the bacterial genome. The third element is a double stranded synthetic oligonucleotide complementary to DNA regions proceeding and following the Cas9 cleavage site and which creates the desired mutation by promoting the λ red-dependent, double cross over event.

Figure 16:
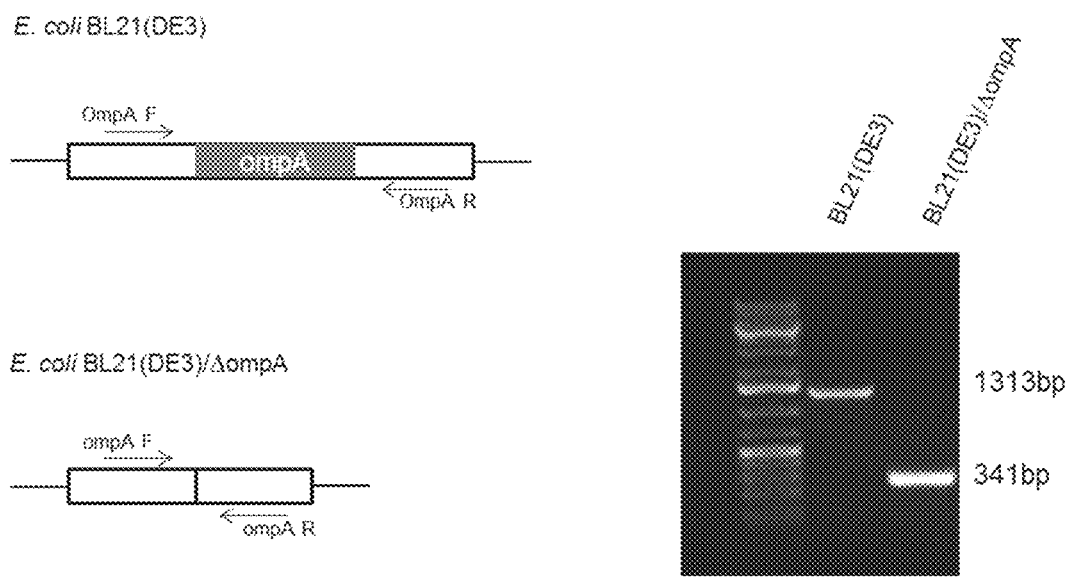

According to this CRISPR/Cas9 mutation-induced protocol, the pCas9-λred plasmid is used to transform the E. coli strain in which mutations have to be introduced. In this work E. coli BL21(DE3) strain was used, generating BL21(DE3) (pCas9-λred) strain. The next step involves the co-transformation of BL21(DE3)(pCas9-λred) with pCRISPR-Km$^R$-SacB-gompA, encoding the gRNA transcript which mediates the Cas9 cleavage within the ompA gene (FIG. 14), and the 120 bp oligonucleotide "ΔompA" which promotes the double cross-over recombination and the complete elimination of the ompA gene (FIG. 15). Transformant clones were selected on LB agar plates supplemented with chloramphenicol (25 µg/ml) and kanamycin (50 µg/ml) and mutant clones were analyzed by PCR (FIG. 16). One clone carrying the mutation was grown overnight in LB supplemented with chloramphenicol and 5% sucrose to eliminate pCRISPR-Km$^R$SacB-gDNA plasmid. The overnight culture was directly used to prepare competent cells for a second round of gene-specific mutation.

Figure 19:
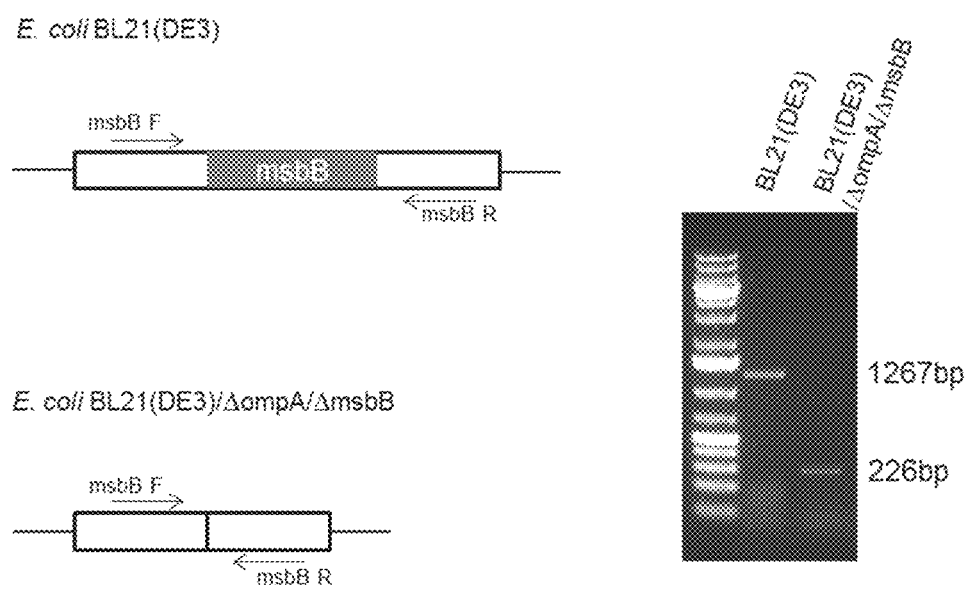

In a second round of gene specific-mutation, BL21(DE3) (pCas9-λred)/ΔompA cells were co-transformed with pCRISPR-Km$^R$SacB-gmsbB (FIG. 17), to mediate the cleavage of msbB gene by Cas9, and the 120 bp oligonucleotide "ΔmsbB" as a donor for the double cross-over recombination for the deletion of the whole msbB gene (FIG. 18). As described above the selection of transformant colonies was performed on LB agar plates supplemented with chloramphenicol (25 µg/ml) and kanamycin (50 µg/ml) and mutant clones were analyzed by PCR (FIG. 19). A positive colony was used to prepare competent cells after depletion of pCRISPR-Km$^R$SacB-gmsbB by overnight growth in LB supplemented with chloramphenicol and 5% sucrose.

Figure 22:
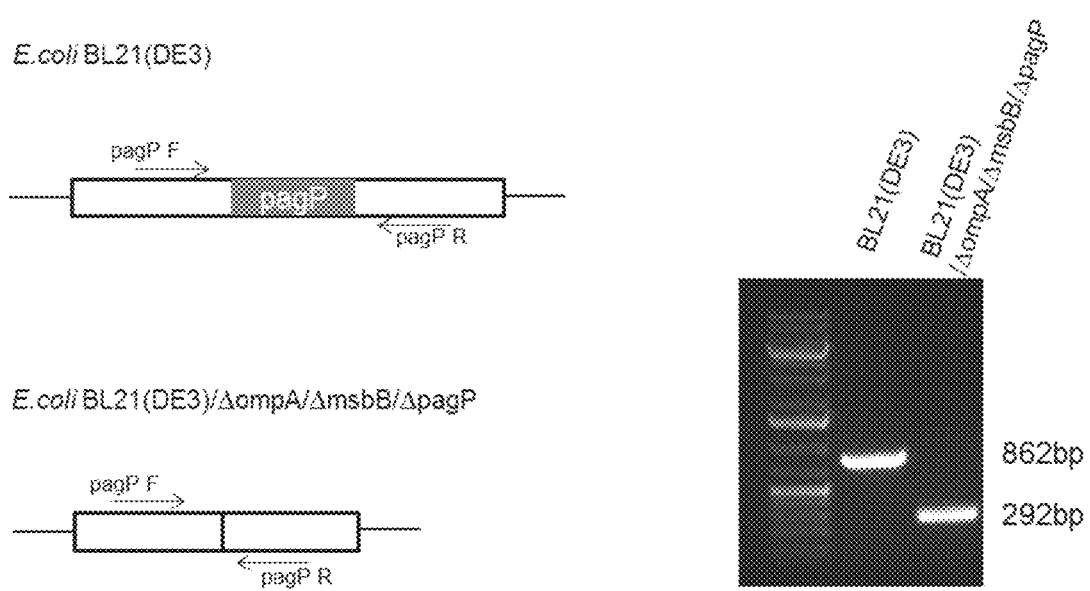

The third round of gene-specific mutation involved the elimination of pagP gene to generate E. coli BL21(DE3) ΔompA/ΔmsbB/ΔpagP strain. Co-transformation of BL21 (DE3)(pCas9-λred)ΔompA/ΔmsbB strain was performed using pCRISPR-Km$^R$SacB-gpagP, transcribing the gRNA complementary to a region within the pagP gene (FIG. 20), and the 120 bp oligonucleotide "ΔpagP" to recover double strand break and simultaneously eliminate pagP gene (FIG. 21). Transformed colony grown on LB agar plate supplemented with chloramphenicol (25 µg/ml) and kanamycin (50 µg/ml) were analyzed by PCR (FIG. 22).

5.4 Example 4—Analysis of Heterologous Antigens Expression

The recombinant plasmids encoding all the heterologous antigens fused to the Lpp leader sequence were used to transform E. coli strain BL21(DE3)/ΔompA and E. coli strain BL21(DE3)/ΔompA/ΔmsbB/ΔpagP. To investigate if the lipidated version of the antigens were expressed in the two strains and could reach the membrane compartment, each strain was grown in LB medium and when cultures reached an $OD_{600}$ value=0.5, IPTG was added at 1 mM final concentration. After two additional hours of growth at 37° C., vesicles were purified from culture supernatants by using ultrafiltration coupled to ultracentrifugation. More specifically, OMVs were collected from culture supernatants by filtration through a 0.22 µm pore size filter (Millipore) and by high-speed centrifugation (200,000×g for 2 hours). Pellets containing OMVs were finally suspended in PBS. The presence of the antigens in total bacterial lysates and OMV preparations from BL21(DE3)/ΔompA/ΔmsbB/ΔpagP strain was analyzed by SDS-PAGE. As shown in FIG. 23A all antigens could be visualized by Coomassie Blue staining and compartmentalized in OMVs. Similarly, the antigens compartmentalized in OMVs from BL21(DE3)/ΔompA recipient strain (FIG. 23B). In order to quantify the amount of heterologous lipidated proteins incorporated into the OMVs from BL21(DE3)/ΔompA/ΔmsbB/ΔpagP strain a semi quantitative Western Blot analysis was performed. In essence, three different amounts of engineered OMVs were loaded onto a 4-12% SDS-polyacrilamide gels along with increasing concentration of the corresponding purified protein, and then the separated proteins were transferred to nitrocellulose filters. The filters were blocked overnight at 4° C. by agitation in blocking solution (10% skimmed milk and 0.05% Tween in PBS), followed by incubation for 90 minutes at 37° C. with a 1:1,000 dilution of antibody raised against Slo or Hla or Spa$_{KKAA}$ or LukE or CsA1 or FhuD2 proteins in 3% skimmed milk and 0.05% Tween in PBS. After 3 washing steps in PBS-Tween, the filters were incubated in a 1:2,000 dilution of peroxidase-conjugated immunoglobulin (Dako) in 3% skimmed milk and 0.05% Tween in PBS for 1 hour, and after 3 washing steps, bound conjugated IgGs were detected using the Super Signal West Pico chemo-luminescent substrate (Pierce). To quantify the amount of recombinant antigen present in each OMV preparation, the intensities of the bands were compared to the band intensities of known amounts of purified proteins.

From FIG. 24 the following conclusions can be drawn. Lipidated $Slo_{dm}$ was highly expressed in OMVs. Considering only the high molecular weight band which corresponds to the full-length protein (the other bands most likely represent partial degradation products) approximately 150 ng of Lpp-$Slo_{dm}$/μg OMVs could be estimated which represents approximately 15% of total OMV proteins. A similar level of expression was observed for the lipidated version of $HLA_{H35L}$. Lipidated LukE, $SpA_{KKAA}$ and CsA1 represented more than 20% of total OMV proteins (25 ng/100 ng of OMVs) (rLukE moved with a slightly higher electrophoretic mobility because it carries a short His-TAG amino acid sequence at the C-terminus used for purification purposed). Finally, lipidated FhuD2 was expressed at extremely high levels, corresponding to approximately 30-40% of total OMVs proteins.

Interestingly and surprising, the non-lipidated version of all recombinant antigens did compartmentalized in OMVs but were expressed at a substantially lower level. In general, at least a tenfold difference in protein compartmentalization was observed, with non-lipidated LukE being found in OMVs at a concentration lower than 1% (barely visible by Western Blot in the lane loaded with 10 μg of OMVs).

5.5 Example 5—Analysis of Lipidation of Heterologous Antigens in OMVs

Since the antigens fused to the Lpp leader sequence carry a canonical lipobox (LAGC), it is likely that they are first acylated and subsequently cleaved by the lipoprotein specific leader peptidase (the product of lsp gene). To confirm that all the antigens are subjected to acylation when expressed in E. coli BL21(DE3) ΔompA/ΔmsbB/ΔpagP strain, vesicles containing the proteins of interest were solubilized at 4° C. with a 1% water solution of Triton X-114 and subsequently the samples were warmed to 37° C. to partition Triton X-114 into two phases: a detergent-rich hydrophobic phase and a detergent-poor hydrophilic phase. Membrane proteins, including lipoproteins, typically partition selectively into the Triton X-114 hydrophobic phase (Bordier, 1981). As shown in FIG. 25 all the antigens containing the wild type Lpp leader sequence ((A) Lpp-$Slo_{dm}OMV_{3ko}$; (B) Lpp-$CsA1OMV_{3ko}$; (C) $FhuD2OMV_{3ko}$) are enriched in the hydrophobic phase (leftmost panels). When the Cysteine residue at position +1 was replaced with an Alanine ((A) Lpp-$Slo_{dm}$-C>AOMV; (B) Lpp-CsA1-C>AOMV; (C) FhuD2-C>AOMV) all the antigens were enriched in the aqueous phase of Triton X-114.

5.6 Example 6—OMVs from Strains Carrying Mutations in Genes Involved in Membrane Structure and Trafficking and Expressing Lipidated Heterologous Antigens Poorly Stimulate TLR4

One abundant component of OMVs is LPS, which represent a major building block of the outer leaflet of the outer membrane of most Gram-negative bacteria, including E. coli. While LPS, and in particular its Lipid A moiety, is an excellent stimulator of innate and adaptive immunity, an excess of LPS is reactogenic and toxic. Such reactogenicity is due to the fact that LPS binds CD14 and the TLR4/MD2 complex on the surface of host immune cells, triggering the activation of several genes involved in inflammatory responses. Therefore, the possibility to modulate amount, compartmentalization and structure of LPS present in OMVs while maintaining the self-adjuvanticity of the vesicles is key to develop effective and safe vaccines.

A number of in vitro and in vivo assays can be used to measure the LPS-dependent immunostimulatory activity of OMVs and, indirectly, their reactogenicity. One convenient in vitro assay is based on the use of cell lines, for instance HEK 293 cell line, expressing human TLR4 gene. Such cell lines can be constructed in house but are also easily accessible from specialized manufacturers, such as the HEK-Blue™ hTLR4 cell line from Invivogen. HEK-Blue™ hTLR4 cells are specifically designed for studying the stimulation of human TLR4 by monitoring the activation of NF-kB. They were obtained from HEK293 by co-transfecting the hTLR4 gene, the MD-2/CD14 co-receptor genes and a secreted embryonic alkaline phosphatase (SEAP) reporter gene. The SEAP reporter gene is placed under the control of an IL-12 p40 minimal promoter fused to five NF-kB and AP-1-binding sites. Stimulation with a TLR4 ligand activates NF-kB and AP-1 which, in turn, induces the production of SEAP which can be detected by a simple colorimetric assay. The beauty of the assay based on HEK-Blue™ hTLR4 cells is that it is quantitative: the higher the amount of LPS in the test sample, the higher the optical density of the reaction mixture after sample addition.

To investigate the TLR4 agonistic activity of OMVs, HEK-Blue™ hTLR4 cells were grown as recommended by the provider, in complete DMEM with 10% endotoxin-free FBS and proper antibiotics. Endotoxin-free water was employed for the preparation of solution of the alkaline phosphatase detection reagent QUANTI-Blue™, and for diluting OMV samples and purified LPS. More specifically, $5 \times 10^4$ cells/well were seeded in a flat-bottom 96-well plate and stimulated for 16-17 hours with different concentrations of OMVs or LPS-EK ultrapure (TLR4 agonist) as positive control. Detection of SEAP activity from cell culture supernatants was performed the following day by mixing 200 μl QUANTI-Blue™ per well of a U-bottom 96-well plate with 20 μl supernatant of stimulated and control cells. After 1 h OD (655 nm) was measured with a spectrophotometer.

Different preparations of OMVs were tested. First of all, the TLR4 agonistic activity of OMVs from E. coli BL21 (DE3) ΔompA and E. coli BL21(DE3) ΔompA/ΔmsbB/ΔpagP strains was tested. As shown in FIG. 26, vesicles purified from E. coli BL21(DE3) ΔompA displayed a TLR4 agonistic activity approximately fiftyfold higher than the same amount of OMVs from E. coli BL21(DE3) ΔompA/ΔmsbB/ΔpagP. This is consistent with the fact that E. coli BL21(DE3) ΔompA produces an hexa-acylated LPS, while E. coli BL21(DE3) ΔompA/ΔmsbB/ΔpagP carries a less-toxigenic/reactogenic penta-acylated variant (Dong H. L. et al., (2011) Vaccine, 29, 8293-8301). OMVs were also purified from E. coli BL21(DE3) ΔompA(pET-Lpp_FhuD2) and E. coli BL21(DE3) ΔompA(pET-Lpp_CsA1) strains expressing the lipidated forms of FhuD2 and CsA1, respectively. When tested in the TLR4 assay, these vesicles displayed a TLR4 agonist activity quantitatively similar to the ones purified from the recipient E. coli BL21(DE3) ΔompA strain. A third set of OMVs were obtained from the four E. coli strains: BL21(DE3) ΔompA/ΔmsbB/ΔpagP(pET-Lpp_FhuD2), BL21(DE3) ΔompA/ΔmsbB/ΔpagP(pET-Lpp_CsA1), BL21(DE3) ΔompA/ΔmsbB/ΔpagP(pET-Lpp_Hla) and BL21(DE3) ΔompA/ΔmsbB/ΔpagP (pET-Lpp_LukE). The four OMV preparations were tested in the TLR4 stimulation in vitro assay. Quite surprisingly and completely unexpected, all vesicles engineered with the lipidated forms of bacterial antigens could appreciably stimulate TLR4 only at concentrations higher than 0.1-1 µg/ml and never reached a plateau under the conditions used in the assay.

These data indicate that by expressing lipidated heterologous antigens in strains carrying mutations in genes involved in membrane structure and trafficking, and in particular, in strains carrying mutation in ompA, msbB and pagP genes, the reactogenic/toxigenic of OMVs carrying the engineered antigens, can be substantially reduced.

5.7 Example 7—Immunogenicity of Engineered OMVs Carrying Recombinant Lipidated Antigens To test whether OMVs expressing lipidated antigens could elicit antigen-specific-antibody responses two sets of experiments were carried out. First, mice were immunized with 30 µg or 3 µg of OMVs from E. coli BL21(DE3) ΔompA strain expressing Lpp-Slo$_{dm}$ (Lpp-Slo$_{dm}$-OMV$_{\Delta ompA}$) in the presence or absence of Alum (2 mg/ml) and total IgG were measured by ELISA. As a comparison, mice were also immunized with 30 µg of OMVs from E. coli BL21(DE3) ΔompA expressing non-lipidated Sloan, (Lpp-Slo$_{dm}$C>A-OMV$_{\Delta ompA}$). Sera were collected seven days after the third vaccine dose (post3) and IgGs against Sloan, were detected by using plates coated in each well with purified Slo. More specifically, coating was carried out by incubating plates overnight at 4° C. with 100 µl of Sloan, (3 µg/ml). Subsequently, wells were washed three times with PBST (0.05% Tween 20 in PBS, pH 7.4), incubated with 100 µl of 1% BSA in PBS for 1 h at room temperature and washed again three times with PBST. Serial dilutions of serum samples in PBST containing 1% BSA were added to the plates, incubated 2 h at 37° C., and washed three times with PBST. Then 100 µl/well of 1:2.000 diluted, alkaline phosphatase-conjugated goat anti-mouse IgGs, were added and left for 2 h at 37° C. After triple PBST wash, bound alkaline phosphatase-conjugated antibodies were detected by adding 100 µl/well of 3 mg/ml para-nitrophenyl-phosphate disodium hexahydrate (Sigma-Aldrich) in 1M diethanolamine buffer (pH 9.8). After 10 minute incubation at room temperature, the reaction was stopped with 100 µl 7% EDTA and substrate hydrolysis was analyzed at 405 nm in a microplate spectrophotometer. As shown in FIG. 27A, OMVs carrying lipidated Sloan, induced consistently higher IgG titers with respect to the OMVs carrying the non-lipidated antigen, 3 µg of Lpp-Slo$_{dm}$-OMV$_{\Delta ompA}$ eliciting a titer similar to the one measured in mice immunized with tenfold higher amount of Lpp-Slo$_{dm}$C>A-OMV$_{\Delta ompA}$. In the presence of Alum the superiority of Lpp-Slo$_{dm}$-OMV$_{\Delta ompA}$ was even more pronounced.

Next the five OMV preparations from BL21(DE3) ΔompA/ΔmsbB/ΔpagP strains carrying lipidated Csa1, Hla$_{H35L}$, FhuD2, Spa$_{KKAA}$, and LukE were mixed together (20 µg each) and used to immunized CD1 mice in the absence of Alum. After three immunization total IgGs against each antigen were measured as described above. As shown in FIG. 27B, a the combination of OMVs carrying lipidated antigens were able to induce IgG titers against all the antigens.

Finally, the isotype of the antigen specific antibodies induced by Lpp-Slo$_{dm}$-OMV$_{\Delta ompA}$ and by the five OMV COMBO described above was analyzed. To this aim, ELISA was carried out as illustrated previously with the only difference that as secondary antibodies alkaline phosphatase-conjugated goat anti-mouse IgG1 or IgG2A antibodies were used. FIG. 28 shows the IgG1 and IgG2A induced against Slo$_{dm}$ by Lpp-Slo$_{dm}$-OMV$_{\Delta ompA}$ and the IgG1 and IgG2A induced against FhuD2 and CsA1 by the COMBO. The data indicate that even if the OMVs from BL21(DE3) ΔompA/ΔmsbB/ΔpagP expressing lipidated antigens have a much lower TLR4 stimulatory activity and (beneficially) much less reactogenicity with respect to the OMVs from BL21(DE3) ΔompA, immune responses skewed toward a Th1 profile were induced.

TABLE

List of oligonucleotides/primers used in this study

| Name | Sequence |
|---|---|
| Lpp-F (SEQ ID NO: 37) | GGAGATATACATATGATGAAAGCTACTAAACTGGTACTGGG |
| Lpp-25-R-bis (SEQ ID NO: 38) | GTTTTGTTTGTTGCTGGAGCAACCTGCCAGCAGAG |
| 25-lpp-F (SEQ ID NO: 39) | GGTTGCTCCAGCAACAAACAAAACACTGCTAGTACAG |
| 25-R (SEQ ID NO: 40) | GTGATGGTGATGTTACTACTTATAAGTAATCGAACCATATG |
| Petno (SEQ ID NO: 41) | CATATGTATATCTCCTTCTTAAAGTTAAAC |
| Nohisflag (SEQ ID NO: 42) | TAACATCACCATCACCATCACGATTACAAAGA |
| 57-lpp-F (SEQ ID NO: 43) | GCAGGTTGCTCCAGCGCAGCAGATGAGCTAAGCA |
| Spycep-R (SEQ ID NO: 44) | GTGATGGTGATGTTATTAGGCTTTTGCTGTTGCTGAGGT |
| Lpp-R-plasmid (SEQ ID NO: 45) | GCTGGAGCAACCTGCCAGCAGAG |
| lpp-hla-f1 (SEQ ID NO: 46) | ctgctggcaggttgcGCAGATTCTGATATTAATATTAAAACCGGT |

TABLE-continued

List of oligonucleotides/primers used in this study

| Name | Sequence |
|---|---|
| hla-r1 (SEQ ID NO: 47) | gtgatggtgatgttaATTTGTCATTTCTTCTTTTTCCCAATCGAT |
| lpp-sta006-f1 (SEQ ID NO: 48) | ctgctggcaggttgcGGGAACCAAGGTGAAAAAAATAACAAAG |
| sta006-r1 (SEQ ID NO: 49) | gtgatggtgatgttaTTTTGCAGCTTTAATTAATTTTTCTTTTAAATCTTTAC |
| lpp-sta011-f1 (SEQ ID NO: 50) | ctgctggcaggttgcGGCATAGGTAAAGAAGCGGAAG |
| sta011-r1 (SEQ ID NO: 51) | gtgatggtgatgttaTACATCTCCGCTTTTTTTATAATCTAAGC |
| lpp-spa-f1 (SEQ ID NO: 52) | ctgctggcaggttgcGCACAGCATGATGAAGCCAAAAAA |
| spa-r1 (SEQ ID NO: 53) | gtgatggtgatgttaTTTAGGTGCCTGTGCGTCGTT |
| lpp-luke-f1 (SEQ ID NO: 54) | ctgctggcaggttgcAATACTAATATTGAAAATATTGGTGATGGTGC |
| luke-r1 (SEQ ID NO: 55) | gtgatggtgatgttaATTATGTCCTTTCACTTTAATTTCGTGTGTTTTCCA |
| lpp-F-ALA-25 (SEQ ID NO: 56) | CAGGTGCCTCCAGCAACAAACAAAACACTG |
| lpp-F-ALA- (SEQ ID NO: 57) | CAGGTGCCTCCAGCGCAGCAGATGAGC |
| Lpp-R-ALA (SEQ ID NO: 58) | GCTGGAGGCACCTGCCAGCAGAG |
| C > A Common rev (SEQ ID NO: 59) | ACCTGCCAGCAGAGTAGAACCCAGGATTACCGCGCC |
| C21A-Csa1_F (SEQ ID NO: 60) | ACT CTG CTG GCA GGT gcC GGC ATA GGT AAA GAA GCG |
| C21A-Sta006_F (SEQ ID NO: 61) | ACT CTG CTG GCA GGT gcC GGG AAC CAA GGT G |
| C21A-SPAKKAA_F (SEQ ID NO: 62) | ACT CTG CTG GCA GGT gcC GCA CAG CAT GAT G |
| C21A-LukE_F (SEQ ID NO: 63) | ACT CTG CTG GCA GGT gcC AAT ACT AAT ATT G |
| C21A-HLA_F (SEQ ID NO: 64) | ACT CTG CTG GCA GGT gcC GCA GAT TCT GAT ATT |
| gompA f (SEQ ID NO: 65) | aaacTGTTGGCTTTGAAATGGGTTACGACTGGTTg |
| gompA R (SEQ ID NO: 66) | aaaacAACCAGTCGTAACCCATTTCAAAGCCAACA |
| gmsbB f (SEQ ID NO: 67) | aaacTCCTTTCGCCACCCGCGCTACTGGGGAGCAg |
| gmsbB R (SEQ ID NO: 68) | aaaacTGCTCCCCAGTAGCGCGGGTGGCGAAAGGA |
| gpagP f (SEQ ID NO: 69) | aaacACAACGTTTAGAGAAAATATTGCACAAACCg |
| gpagP R (SEQ ID NO: 70) | aaaacGGCATGCACGTTTCGCTTACGACAAAGAAA |
| Donor ΔompA f (SEQ ID NO: 71) | ACCGTGTTATCTCGTTGGAGATATTCATGGCGTATTTTGGATGATAACGAGGCGCAAAAGTTCTCGTCTGGTAGAAA |

TABLE-continued

List of oligonucleotides/primers used in this study

| Name | Sequence |
|---|---|
| | AACCCCGCTGCTGCGGGGTTTTTTTTGCCTTTAGTAAATTGA |
| Donor ompA rev (SEQ ID NO: 72) | TCAATTTACTAAAGGCAAAAAAAACCCCGCAGCAGCGGGGTTTTTCTACCAGACGAGAACTTTTTGCGCCTCGTTATCATCCAAAATACGCCATGAATATCTCCAACGAGATAACACGGT |
| Donor ΔmsbB f (SEQ ID NO: 73) | CAAGTTGCGCCGCTACACTATCACCAGATTGATTTTTGCCTTATCCGAAACTGGAAAAGCAAAGCCTCTCGCGAGGAGAGGCCTTCGCCTGATGATAAGTTCAAGTTTGCTTCAGAATA |
| Donor msbB rev (SEQ ID NO: 74) | TATTCTGAAGCAAACTTGAACTTATCATCAGGCGAAGGCCTCTCCTCGCGAGAGGCTTTTGCTTTTCCAGTTTCGGATAAGGCAAAAATCAATCTGGTGATAGTGTAGCGGCGCAACTTG |
| Donor ΔpagP f (SEQ ID NO: 75) | TGTTAATTGTAGCTTTGCTATGCTAGTAGTAGATTTTGATAAATGTTTTATGGTCACAAAGTTTTAGTAACTTCTTTAAATCAATAGCTAAAATAAGTAACATCAAAAATAACGCGAC |
| Donor pagP rev (SEQ ID NO: 76) | GTCGCGTTATTTTTGATGTTACTTATTTTAGCTATTGATTTTAAAGAAGTTACTAAAACTTTGTGACCATAAAACATTTATCAAAAATCTACTACTAGCATAGCAAAGCTACAATTACA |
| ompA F (SEQ ID NO: 77) | CGTTGTAGACTTTACATCGCCAG |
| ompA R (SEQ ID NO: 78) | GTCTTCTCTGAAGCAGGATCTGC |
| msbB F (SEQ ID NO: 79) | GCCAAAGAGATTGTGCCGCAGC |
| msbB R (SEQ ID NO: 80) | CGGTAGAGTAAGTACGTTGCCG |
| pagP F (SEQ ID NO: 81) | GCATCATCTTTAATCGATGCGCGG |
| pagP R (SEQ ID NO: 82) | GCTGTGTCGGTTACCAGTACACC |

| SEQUENCES | |
|---|---|
| SEQ ID NO: 1 | Lpp-Slo$_{dm}$: sequence of Lpp-slo$_{dm}$ gene |
| SEQ ID NO: 20 | lipidated Slo$_{dm}$ protein |
| SEQ ID NO: 2 | Lpp-C > A slo$_{dm}$ gene |
| SEQ ID NO: 21 | non-lipidated Slo$_{dm}$ protein |
| SEQ ID NO: 3 | hla$_{H35L}$ synthetic gene |
| SEQ ID NO: 22 | Hla$_{H35L}$ protein |
| SEQ ID NO: 4 | Lpp-hla$_{H35L}$ gene |
| SEQ ID NO: 23 | lipidated Hla$_{H35L}$ protein |
| SEQ ID NO: 5 | Lpp-C > A hla$_{H35L}$ gene |
| SEQ ID NO: 24 | non-lipidated Hla$_{H35L}$ protein |
| SEQ ID NO: 6 | fhuD2 synthetic gene |
| SEQ ID NO: 25 | FhuD2 protein |
| SEQ ID NO: 7 | Lpp-fhuD2 gene |
| SEQ ID NO: 26 | lipidated FhuD2 protein |
| SEQ ID NO: 8 | Lpp-C > A fhuD2 gene |
| SEQ ID NO: 27 | non-lipidated FhuD2 protein |
| SEQ ID NO: 9 | csA1 synthetic gene |
| SEQ ID NO: 28 | CsA1 protein |
| SEQ ID NO: 10 | Lpp-csA1 gene |
| SEQ ID NO: 29 | lipidated CsA1 protein |
| SEQ ID NO: 11 | Lpp-C > A csA1 gene |
| SEQ ID NO: 30 | non-lipidated CsA1 protein |
| SEQ ID NO: 12 | spa$_{KKAA}$ synthetic gene |
| SEQ ID NO: 31 | Spa$_{KKAA}$ protein |
| SEQ ID NO: 13 | Lpp-spa$_{KKAA}$ gene |
| SEQ ID NO: 32 | lipidated Spa$_{KKAA}$ protein |
| SEQ ID NO: 14 | Lpp-C > A spa$_{KKAA}$ gene |
| SEQ ID NO: 33 | non-lipidated Spa$_{KKAA}$ protein |
| SEQ ID NO: 15 | lukE synthetic gene |
| SEQ ID NO: 34 | LukE protein |
| SEQ ID NO: 16 | Lpp-lukE gene |
| SEQ ID NO: 35 | lipidated LukE protein |
| SEQ ID NO: 17 | Lpp-C > A lukE gene |
| SEQ ID NO: 36 | non-lipidated LukE protein |
| SEQ ID NO: 18 | Lambda-red cassette gene sequence |
| SEQ ID NO: 19 | Kanamycin-sacB cassette gene cassette |

1.
Lpp-Slo$_{dm}$: sequence of Lpp-slo$_{dm}$ gene (SEQ ID NO: 1) and the
lipidated Slo$_{dm}$ protein (SEQ ID NO: 20)
DNA sequence
ATGAAAGCTACTAAACTGGTACTGGGCGCGGTAATCCTGGGTTCTACTCTGCTGGCAGGT

TGCAACAAACAAAACACTGCTAGTACAGAAACCACAACGACAAATGAGCAACCAAAGCCA

GAAAGTAGTGAGCTAACTACTGAAAAAGCAGGTCAGAAAACGGATGATATGCTTAACTCT

AACGATATGATTAAGCTTGCTCCCAAAGAAATGCCACTAGAATCTGCAGAAAAAGAAGAA

AAAAAGTCAGAAGACAAAAAAAAGAGCGAAGAAGATCACACTGAAGAAATCAATGACAAG

ATTTATTCACTAAATTATAATGAGCTTGAAGTACTTGCTAAAAATGGTGAAACCATTGAA

AATTTTGTTCCTAAAGAAGGCGTTAAGAAAGCTGATAAATTTATTGTCATTGAAAGAAAG

AAAAAAAATATCAACACTACACCAGTCGATATTTCCATTATTGACTCTGTCACTGATAGG

ACCTATCCAGCAGCCCTTCAGCTGGCTAATAAAGGTTTTACCGAAAACAAACCAGACGCG

GTAGTCACCAAGCGAAACCCACAAAAAATCCATATTGATTTACCAGGTATGGGAGACAAA

GCAACGGTTGAGGTCAATGACCCTACCTATGCCAATGTTTCAACAGCTATTGATAATCTT

GTTAACCAATGGCATGATAATTATTCTGGTGGTAATACGCTTCCTGCCAGAACACAATAT

ACTGAATCAATGGTATATTCTAAGTCACAGATTGAGGCAGCTCTAAATGTTAATAGCAAA

ATCTTAGATGGTACTTTAGGCATTGATTTCAAGTCGATTTCAAAAGGTGAAAAGAAGGTG

ATGATTGCAGCATACAAGCAAATTTTTTACACCGTATCAGCAAACCTTCCTAATAATCCT

GCGGATGTGTTTGATAAATCGGTGACCTTTAAAGAGTTGCAACGAAAAGGTGTCAGCAAT

GAAGCTCCGCCACTCTTTGTGAGTAACGTAGCCTATGGTCGAACTGTTTTTGTCAAACTA

GAAACAAGTTCTAAAAGTAATGATGTTGAAGCGGCCTTTAGTGCAGCTCTAAAAGGAACA

GATGTTAAAACTAATGGAAAATATTCTGATATCTTAGAAAATAGCTCATTTACAGCTGTC

GTTTTAGGAGGAGATGCTGCAGAGCACAATAAGGTAGTCACAAAAGACTTTGATGTTATT

AGAAACGTTATCAAAGACAATGCTACCTTCAGTAGAAAAAACCTAGCTTATCCTATTTCA

TACACCAGTGTTTTCCTTAAAAATAATAAAATTGCGGGTGTCAATAACAGAACTGAATAC

GTTGAAACAACATCTACCGAGTACACTAGTGGAAAAATTAACCTGTCTCATCAAGGCGCG

TATGTTGCTCAATATGAAATCCTTTGGGATGAAATCAATTATGATGACAAAGGAAAAGAA

GTGATTACAAAACGACGTTGGGACAACAACTGGTATAGTAAGACATCACCATTTAGCACA

GTTATCCCACTAGGAGCTAATTCACGAAATATCCGTATCATGGCTAGAGAGTGCACTGGC

TTAGCTTTCGAATGGTGGCGAAAAGTGATCGACGAAAGAGATGTGAAACTGTCTAAAGAA

ATCAATGTCAATATCTCAGGATCAACCTTGAGCCCATATGGTTCGATTACTTATAAGTAG

Amino acid sequence
MKATKLVLGAVILGSTLLAGCNKQNTASTETTTTNEQPKPESSELTTEKAGQKTDDMLNS

NDMIKLAPKEMPLESAEKEEKKSEDKKKSEEDHTEEINDKIYSLNYNELEVLAKNGETIE

NFVPKEGVKKADKFIVIERKKKNINTTPVDISIIDSVTDRTYPAALQLANKGFTENKPDA

VVTKRNPQKIHIDLPGMGDKATVEVNDPTYANVSTAIDNLVNQWHDNYSGGNTLPARTQY

TESMVYSKSQIEAALNVNSKILDGTLGIDFKSISKGEKKVMIAAYKQIFYTVSANLPNNP

ADVFDKSVTFKELQRKGVSNEAPPLFVSNVAYGRTVFVKLETSSKSNDVEAAFSAALKGT

DVKTNGKYSDILENSSFTAVVLGGDAAEHNKVVTKDFDVIRNVIKDNATFSRKNLAYPIS

YTSVFLKNNKIAGVNNRTEYVETTSTEYTSGKINLSHQGAYVAQYEILWDEINYDDKGKE

VITKRRWDNNWYSKTSPFSTVIPLGANSRNIRIMARECTGLAFEWWRKVIDERDVKLSKE

INVNISGSTLSPYGSITYK

-continued

2.
Lpp-C > A-Slo$_{dm}$: sequence of the lpp-C > A slo$_{dm}$ gene (SEQ ID NO: 2) and non-lipidated Slo$_{dm}$ protein (SEQ ID NO: 21)

DNA sequence
ATGAAAGCTACTAAACTGGTACTGGGCGCGGTAATCCTGGGTTCTACTCTGCTGGCAGGT

GCCAACAAACAAAACACTGCTAGTACAGAAACCACAACGACAAATGAGCAACCAAAGCCA

GAAAGTAGTGAGCTAACTACTGAAAAAGCAGGTCAGAAAACGGATGATATGCTTAACTCT

AACGATATGATTAAGCTTGCTCCCAAAGAAATGCCACTAGAATCTGCAGAAAAAGAAGAA

AAAAAGTCAGAAGACAAAAAAAAGAGCGAAGAAGATCACACTGAAGAAATCAATGACAAG

ATTTATTCACTAAATTATAATGAGCTTGAAGTACTTGCTAAAAATGGTGAAACCATTGAA

AATTTTGTTCCTAAAGAAGGCGTTAAGAAAGCTGATAAATTTATTGTCATTGAAAGAAAG

AAAAAAAATATCAACACTACACCAGTCGATATTTCCATTATTGACTCTGTCACTGATAGG

ACCTATCCAGCAGCCCTTCAGCTGGCTAATAAAGGTTTTACCGAAAACAAACCAGACGCG

GTAGTCACCAAGCGAAACCCACAAAAAATCCATATTGATTTACCAGGTATGGGAGACAAA

GCAACGGTTGAGGTCAATGACCCTACCTATGCCAATGTTTCAACAGCTATTGATAATCTT

GTTAACCAATGGCATGATAATTATTCTGGTGGTAATACGCTTCCTGCCAGAACACAATAT

ACTGAATCAATGGTATATTCTAAGTCACAGATTGAGGCAGCTCTAAATGTTAATAGCAAA

ATCTTAGATGGTACTTTAGGCATTGATTTCAAGTCGATTTCAAAAGGTGAAAAGAAGGTG

ATGATTGCAGCATACAAGCAAATTTTTTACACCGTATCAGCAAACCTTCCTAATAATCCT

GCGGATGTGTTTGATAAATCGGTGACCTTTAAAGAGTTGCAACGAAAAGGTGTCAGCAAT

GAAGCTCCGCCACTCTTTGTGAGTAACGTAGCCTATGGTCGAACTGTTTTTGTCAAACTA

GAAACAAGTTCTAAAAGTAATGATGTTGAAGCGGCCTTTAGTGCAGCTCTAAAAGGAACA

GATGTTAAAACTAATGGAAAATATTCTGATATCTTAGAAAATAGCTCATTTACAGCTGTC

GTTTTAGGAGGAGATGCTGCAGAGCACAATAAGGTAGTCACAAAAGACTTTGATGTTATT

AGAAACGTTATCAAAGACAATGCTACCTTCAGTAGAAAAAACCTAGCTTATCCTATTTCA

TACACCAGTGTTTTCCTTAAAAATAATAAAATTGCGGGTGTCAATAACAGAACTGAATAC

GTTGAAACAACATCTACCGAGTACACTAGTGGAAAAATTAACCTGTCTCATCAAGGCGCG

TATGTTGCTCAATATGAAATCCTTTGGGATGAAATCAATTATGATGACAAAGGAAAAGAA

GTGATTACAAAACGACGTTGGGACAACAACTGGTATAGTAAGACATCACCATTTAGCACA

GTTATCCCACTAGGAGCTAATTCACGAAATATCCGTATCATGGCTAGAGAGTGCACTGGC

TTAGCTTTCGAATGGTGGCGAAAAGTGATCGACGAAAGAGATGTGAAACTGTCTAAAGAA

ATCAATGTCAATATCTCAGGATCAACCTTGAGCCCATATGGTTCGATTACTTATAAGTAG

Amino acid sequence
MKATKLVLGAVILGSTLLAGANKQNTASTETTTTNEQPKPESSELTTEKAGQKTDDMLNS

NDMIKLAPKEMPLESAEKEEKKSEDKKKSEEDHTEEINDKIYSLNYNELEVLAKNGETIE

NFVPKEGVKKADKFIVIERKKKNINTTPVDISIIDSVTDRTYPAALQLANKGFTENKPDA

VVTKRNPQKIHIDLPGMGDKATVEVNDPTYANVSTAIDNLVNQWHDNYSGGNTLPARTQY

TESMVYSKSQIEAALNVNSKILDGTLGIDFKSISKGEKKVMIAAYKQIFYTVSANLPNNP

ADVFDKSVTFKELQRKGVSNEAPPLFVSNVAYGRTVFVKLETSSKSNDVEAAFSAALKGT

DVKTNGKYSDILENSSFTAVVLGGDAAEHNKVVTKDFDVIRNVIKDNATFSRKNLAYPIS

YTSVFLKNNKIAGVNNRTEYVETTSTEYTSGKINLSHQGAYVAQYEILWDEINYDDKGKE

VITKRRWDNNWYSKTSPFSTVIPLGANSRNIRIMARECTGLAFEWWRKVIDERDVKLSKE

INVNISGSTLSPYGSITYK*

-continued 3.
hla$_{H35L}$:sequence of hla$_{H35L}$ synthetic gene (SEQ ID NO: 3) and
Hla$_{H35L}$ protein (SEQ ID NO: 22)
DNA sequence
GCAGATTCTGATATTAATATTAAAACCGGTACTACAGATATTGGAAGCAATACTACAGTA

AAAACAGGTGATTTAGTCACTTATGATAAAGAAAATGGCATGTTAAAAAAAGTATTTTAT

AGTTTTATCGATGATAAAAATCATAATAAAAAACTGCTAGTTATTAGAACGAAAGGTACC

ATTGCTGGTCAATATAGAGTTTATAGCGAAGAAGGTGCTAACAAAAGTGGTTTAGCCTGG

CCTTCAGCCTTTAAGGTACAGTTGCAACTACCTGATAATGAAGTAGCTCAAATATCTGAT

TACTATCCAAGAAATTCGATTGATACAAAAGAGTATATGAGTACTTTAACTTATGGATTC

AACGGTAATGTTACTGGTGATGATACAGGAAAAATTGGCGGCCTTATTGGTGCAAATGTT

TCGATTGGTCATACACTGAAATATGTTCAACCTGATTTCAAAACAATTTTAGAGAGCCCA

ACTGATAAAAAAGTAGGCTGGAAAGTGATATTTAACAATATGGTGAATCAAAATTGGGGA

CCATATGATAGAGATTCTTGGAACCCGGTATATGGCAATCAACTTTTCATGAAAACTAGA

AATGGCTCTATGAAAGCAGCAGATAACTTCCTTGATCCTAACAAAGCAAGTTCTCTATTA

TCTTCAGGGTTTTCACCAGACTTCGCTACAGTTATTACTATGGATAGAAAAGCATCCAAA

CAACAAACAAATATAGATGTAATATACGAACGAGTTCGTGATGACTACCAATTGCACTGG

ACTTCAACAAATTGGAAAGGTACCAATACTAAAGATAAATGGATAGATCGTTCTTCAGAA

AGATATAAAATCGATTGGGAAAAAGAAGAAATGACAAATtaa

Amino acid sequence
ADSDINIKTGTTDIGSNTTVKTGDLVTYDKENGMLKKVFYSFIDDKNHNKKLLVIRTKGT

IAGQYRVYSEEGANKSGLAWPSAFKVQLQLPDNEVAQISDYYPRNSIDTKEYMSTLTYGF

NGNVTGDDTGKIGGLIGANVSIGHTLKYVQPDFKTILESPTDKKVGWKVIFNNMVNQNWG

PYDRDSWNPVYGNQLFMKTRNGSMKAADNFLDPNKASSLLSSGFSPDFATVITMDRKASK

QQTNIDVIYERVRDDYQLHWTSTNWKGTNTKDKWIDRSSERYKIDWEKEEMTN*

4.
Lpp-hla$_{H35L}$:sequence of the Lpp-hla$_{H35L}$ gene (SEQ ID NO: 4) and
lipidated Hla$_{H35L}$ protein (SEQ ID NO: 23)
DNA sequence
ATGAAAGCTACTAAACTGGTACTGGGCGCGGTAATCCTGGGTTCTATTTTGCTGGCAGGT

TGCGCAGATTCTGATATTAATATTAAAACCGGTACTACAGATATTGGAAGCAATACTACA

GTAAAAACAGGTGATTTAGTCACTTATGATAAAGAAAATGGCATGCTCAAAAAAGTATTT

TATAGTTTTATCGATGATAAAAATCATAATAAAAAACTGCTAGTTATTAGAACGAAAGGT

ACCATTGCTGGTCAATATAGAGTTTATAGCGAAGAAGGTGCTAACAAAAGTGGTTTAGCC

TGGCCTTCAGCCTTTAAGGTACAGTTGCAACTACCTGATAATGAAGTAGCTCAAATATCT

GATTACTATCCAAGAAATTCGATTGATACAAAAGAGTATATGAGTACTTTAACTTATGGA

TTCAACGGTAATGTTACTGGTGATGATACAGGAAAAATTGGCGGCCTTATTGGTGCAAAT

GTTTCGATTGGTCATACACTGAAATATGTTCAACCTGATTTCAAAACAATTTTAGAGAGC

CCAACTGATAAAAAAGTAGGCTGGAAAGTGATATTTAACAATATGGTGAATCAAAATTGG

GGACCATATGATAGAGATTCTTGGAACCCGGTATATGGCAATCAACTTTTCATGAAAACT

AGAAATGGCTCTATGAAAGCAGCAGATAACTTCCTTGATCCTAACAAAGCAAGTTCTCTA

TTATCTTCAGGGTTTTCACCAGACTTCGCTACAGTTATTACTATGGATAGAAAAGCATCC

AAACAACAAACAAATATAGATGTAATATACGAACGAGTTCGTGATGACTACCAATTGCAC

TGGACTTCAACAAATTGGAAAGGTACCAATACTAAAGATAAATGGATAGATCGTTCTTCA

GAAAGATATAAAATCGATTGGGAAAAAGAAGAAATGACAAATTAA

Amino acid sequence (sequence 23)
MKATKLVLGAVILGSILLAGCADSDINIKTGTTDIGSNTTVKTGDLVTYDKENGMLKKVF

YSFIDDKNHNKKLLVIRTKGTIAGQYRVYSEEGANKSGLAWPSAFKVQLQLPDNEVAQIS

DYYPRNSIDTKEYMSTLTYGFNGNVTGDDTGKIGGLIGANVSIGHTLKYVQPDFKTILES

PTDKKVGWKVIFNNMVNQNWGPYDRDSWNPVYGNQLFMKTRNGSMKAADNFLDPNKASSL

LSSGFSPDFATVITMDRKASKQQTNIDVIYERVRDDYQLHWTSTNWKGTNTKDKWIDRSS

ERYKIDWEKEEMTN*

5.
Lpp-C > A hla$_{H35L}$: sequence of the Lpp-C > A hla$_{H35L}$ gene (SEQ ID
NO: 5) and non-lipidated Hla$_{H35L}$ protein (SEQ ID NO: 24)
DNA Sequence
ATGATGAAAGCTACTAAACTGGTACTGGGCGCGGTAATCCTGGGTTCTACTCTGCTGGCA GGTGCcGCAGATTCTGATATTAATATTAAAACCGGTACTACAGATATTGGAAGCAATACT

ACAGTAAAAACAGGTGATTTAGTCACTTATGATAAAGAAAATGGCATGTTAAAAAAAGTA

TTTTATAGTTTTATCGATGATAAAAATCATAATAAAAAACTGCTAGTTATTAGAACGAAA

GGTACCATTGCTGGTCAATATAGAGTTTATAGCGAAGAAGGTGCTAACAAAAGTGGTTTA

GCCTGGCCTTCAGCCTTTAAGGTACAGTTCAACTACCTGATAATGAAGTAGCTCAAATAT

CTGATTACTATCCAAGAAATTCGATTGATACAAAAGAGTATATGAGTACTTTAACTTATG

GATTCAACGGTAATGTTACTGGTGATGATACAGGAAAAATTGGCGGCCTTATTGGTGCAA

ATGTTTCGATTGGTCATACACTGAAATATGTTCAACCTGATTTCAAAACAATTTTAGAGA

GCCCAACTGATAAAAAAGTAGGCTGGAAAGTGATATTTAACAATATGGTGAATCAAAATT

GGGGACCATATGATAGAGATTCTTGGAACCCGGTATATGGCAATCAACTTTTCATGAAAA

CTAGAAATGGCTCTATGAAAGCAGCAGATAACTTCCTTGATCCTAACAAAGCAAGTTCTC

TATTATCTTCAGGGTTTTCACCAGACTTCGCTACAGTTATTACTATGGATAGAAAAGCAT

CCAAACAACAAACAAATATAGATGTAATATACGAACGAGTTCGTGATGACTACCAATTGC

ACTGGACTTCAACAAATTGGAAAGGTACCAATACTAAAGATAAATGGATAGATCGTTCTT

CAGAAAGATATAAAATCGATTGGGAAAAAGAAGAAATGACAAATtaa

Amino Acid sequence
MKATKLVLGAVILGSTLLAGAADSDINIKTGTTDIGSNTTVKTGDLVTYDKENGMLKKVF

YSFIDDKNHNKKLLVIRTKGTIAGQYRVYSEEGANKSGLAWPSAFKVQLQLPDNEVAQIS

DYYPRNSIDTKEYMSTLTYGFNGNVTGDDTGKIGGLIGANVSIGHTLKYVQPDFKTILES

PTDKKVGWKVIFNNMVNQNWGPYDRDSWNPVYGNQLFMKTRNGSMKAADNFLDPNKASSL

LSSGFSPDFATVITMDRKASKQQTNIDVIYERVRDDYQLHWTSTNWKGTNTKDKWIDRSS

ERYKIDWEKEEMTN*

6.
FhuD2: sequence of the fhuD2 synthetic gene (SEQ ID NO: 6)
and FhuD2 protein (SEQ ID NO: 25)
DNA sequence
TGTGGGAACCAAGGTGAAAAAAATAACAAAGCTGAAACTAAATCTTATAAAATGGACGAT

GGCAAAACGGTAGATATTCCGAAAGACCCTAAACGCATTGCAGTAGTTGCGCCAACATAT

GCTGGTGGACTTAAAAAATTAGGTGCAAACATTGTAGCTGTAAATCAACAAGTCGATCAA

AGCAAAGTATTAAAAGATAAATTTAAAGGTGTTACAAAAATTGGTGATGGCGATGTAGAA

AAAGTTGCTAAAGAAAAGCCAGATTTAATTATTGTATACTCTACTGACAAAGATATTAAA

-continued

```
AAATATCAAAAAGTAGCACCAACAGTAGTTGTTGACTATAATAAGCATAAATATTTAGAA

CAACAAGAAATGTTAGGGAAAATTGTTGGTAAAGAAGATAAAGTAAAAGCTTGGAAGAAA

GATTGGGAAGAAACAACTGCTAAAGACGGTAAAGAAATTAAAAAAGCAATTGGACAAGAT

GCAACAGTGTCATTGTTTGATGAATTTGATAAAAAATTATACACTTACGGCGATAACTGG

GGTCGTGGTGGAGAAGTATTATATCAAGCATTTGGTTTGAAAATGCAACCAGAACAACAA

AAGTTAACTGCAAAAGCAGGTTGGGCTGAAGTGAAACAAGAAGAAATTGAAAAATATGCT

GGTGATTACATTGTGAGTACAAGTGAAGGTAAACCTACACCAGGATACGAATCAACAAAC

ATGTGGAAGAATTTGAAAGCTACTAAAGAAGGACATATTGTTAAAGTTGATGCTGGTACA

TACTGGTACAACGATCCTTATACATTAGATTTCATGCGTAAAGATTTAAAAGAAAAATTA

ATTAAAGCTGCAAAAtaa
``` amino acid sequence
```
CGNQGEKNNKAETKSYKMDDGKTVDIPKDPKRIAVVAPTYAGGLKKLGANIVAVNQQVDQ

SKVLKDKFKGVTKIGDGDVEKVAKEKPDLIIVYSTDKDIKKYQKVAPTVVVDYNKHKYLE

QQEMLGKIVGKEDKVKAWKKDWEETTAKDGKEIKKAIGQDATVSLFDEFDKKLYTYGDNW

GRGGEVLYQAFGLKMQPEQQKLTAKAGWAEVKQEEIEKYAGDYIVSTSEGKPTPGYESTN

MWKNLKATKEGHIVKVDAGTYWYNDPYTLDFMRKDLKEKLIKAAK*
```

7.
Lpp-fhuD2: sequence of the Lpp-fhuD2 gene (SEQ ID NO: 7) and
lipidated FhuD2 protein (SEQ ID NO: 26)
DNA sequence
```
ATGAtgaAAGCTACTAAACTGGTACTGGGCGCGGTAATCCTGGGTTCTACTCTGCTGGCA GGTtgcGGGAACCAAGGTGAAAAAAATAACAAAGCTGAAACTAAATCTTATAAAATGGAC

GATGGCAAAACGGTAGATATTCCGAAAGACCCTAAACGCATTGCAGTAGTTGCGCCAACA

TATGCTGGTGGACTTAAAAAATTAGGTGCAAACATTGTAGCTGTAAATCAACAAGTCGAT

CAAAGCAAAGTATTAAAAGATAAATTTAAAGGTGTTACAAAAATTGGTGATGGCGATGTA

GAAAAAGTTGCTAAAGAAAAGCCAGATTTAATTATTGTATACTCTACTGACAAAGATATT

AAAAAATATCAAAAAGTAGCACCAACAGTAGTTGTTGACTATAATAAGCATAAATATTTA

GAACAACAAGAAATGTTAGGGAAAATTGTTGGTAAAGAAGATAAAGTAAAAGCTTGGAAG

AAAGATTGGGAAGAAACAACTGCTAAAGACGGTAAAGAAATTAAAAAAGCAATTGGACAA

GATGCAACAGTGTCATTGTTTGATGAATTTGATAAAAAATTATACACTTACGGCGATAAC

TGGGGTCGTGGTGGAGAAGTATTATATCAAGCATTTGGTTTGAAAATGCAACCAGAACAA

CAAAAGTTAACTGCAAAAGCAGGTTGGGCTGAAGTGAAACAAGAAGAAATTGAAAAATAT

GCTGGTGATTACATTGTGAGTACAAGTGAAGGTAAACCTACACCAGGATACGAATCAACA

AACATGTGGAAGAATTTGAAAGCTACTAAAGAAGGACATATTGTTAAAGTTGATGCTGGT

ACATACTGGTACAACGATCCTTATACATTAGATTTCATGCGTAAAGATTTAAAAGAAAAA

TTAATTAAAGCTGCAAAATAA
```

Amino acid sequence
```
MKATKLVLGAVILGSTLLAGCGNQGEKNNKAETKSYKMDDGKTVDIPKDPKRIAVVAPTY

AGGLKKLGANIVAVNQQVDQSKVLKDKFKGVTKIGDGDVEKVAKEKPDLIIVYSTDKDIK

KYQKVAPTVVVDYNKHKYLEQQEMLGKIVGKEDKVKAWKKDWEETTAKDGKEIKKAIGQD

ATVSLFDEFDKKLYTYGDNWGRGGEVLYQAFGLKMQPEQQKLTAKAGWAEVKQEEIEKYA

GDYIVSTSEGKPTPGYESTNMWKNLKATKEGHIVKVDAGTYWYNDPYTLDFMRKDLKEKL

IKAAK*
```

8.
Lpp C > A-fhuD2: sequence of the Lpp-C > A fhuD2 gene (SEQ ID NO: 8) and non-lipidated FhuD2 protein (SEQ ID NO: 27)
DNA sequence
ATGAtgaAAGCTACTAAACTGGTACTGGGCGCGGTAATCCTGGGTTCTACTCTGCTGGCA GGTgccGGGAACCAAGGTGAAAAAAATAACAAAGCTGAAACTAAATCTTATAAAATGGAC

GATGGCAAAACGGTAGATATTCCGAAAGACCCTAAACGCATTGCAGTAGTTGCGCCAACA

TATGCTGGTGGACTTAAAAAATTAGGTGCAAACATTGTAGCTGTAAATCAACAAGTCGAT

CAAAGCAAAGTATTAAAAGATAAATTTAAAGGTGTTACAAAAATTGGTGATGGCGATGTA

GAAAAAGTTGCTAAAGAAAAGCCAGATTTAATTATTGTATACTCTACTGACAAAGATATT

AAAAAATATCAAAAAGTAGCACCAACAGTAGTTGTTGACTATAATAAGCATAAATATTTA

GAACAACAAGAAATGTTAGGGAAAATTGTTGGTAAAGAAGATAAAGTAAAAGCTTGGAAG

AAAGATTGGGAAGAAACAACTGCTAAAGACGGTAAAGAAATTAAAAAAGCAATTGGACAA

GATGCAACAGTGTCATTGTTTGATGAATTTGATAAAAAATTATACACTTACGGCGATAAC

TGGGGTCGTGGTGGAGAAGTATTATATCAAGCATTTGGTTTGAAAATGCAACCAGAACAA

CAAAAGTTAACTGCAAAAGCAGGTTGGGCTGAAGTGAAACAAGAAGAAATTGAAAAATAT

GCTGGTGATTACATTGTGAGTACAAGTGAAGGTAAACCTACACCAGGATACGAATCAACA

AACATGTGGAAGAATTTGAAAGCTACTAAAGAAGGACATATTGTTAAAGTTGATGCTGGT

ACATACTGGTACAACGATCCTTATACATTAGATTTCATGCGTAAAGATTTAAAAGAAAAA

TTAATTAAAGCTGCAAAATAA

Amino acid sequence
MKATKLVLGAVILGSTLLAGAGNQGEKNNKAETKSYKMDDGKTVDIPKDPKRIAVVAPTY

AGGLKKLGANIVAVNQQVDQSKVLKDKFKGVTKIGDGDVEKVAKEKPDLIIVYSTDKDIK

KYQKVAPTVVVDYNKHKYLEQQEMLGKIVGKEDKVKAWKKDWEETTAKDGKEIKKAIGQD

ATVSLFDEFDKKLYTYGDNWGRGGEVLYQAFGLKMQPEQQKLTAKAGWAEVKQEEIEKYA

GDYIVSTSEGKPTPGYESTNMWKNLKATKEGHIVKVDAGTYWYNDPYTLDFMRKDLKEKL

IKAAK*

9.
csA1: sequence of the csA1 synthetic gene (SEQ ID NO: 9) and CsA1 protein (SEQ ID NO: 28)
DNA sequence
ATGATGAAACGATTAAACAAATTAGTGTTAGGCATTATTTTTCTGTTTTTAGTCATTAGT

ATCACTGCTGGTTGTGGCATAGGTAAAGAAGCGGAAGTTAAGAAAAGCTTTGAAAAAACA

TTGAGTATGTACCCTATTAAAAATCTAGAGGATTTATACGATAAGGAAGGCTATCGTGAT

GATCAGTTTGATAAAAATGATAAAGGTACATGGATTATAAATTCTGAAATGGTTATTCAA

CCTAATAATGAAGATATGGTAGCTAAAGGCATGGTTCTATATATGAATAGAAATACCAAA

ACAACAAATGGTTACTACTATGTCGATGTGACTAAGGACGAGGATGAAGGAAAACCGCAC

GACAATGAAAAAGATATCCGGTTAAAATGGTCGATAATAAAATCATTCCAACAAAAGAA

ATTAAAGATGAAAAAATAAAAAAGAAATCGAAAACTTTAAGTTCTTTGTTCAATATGGC

GACTTTAAAAATTTGAAAAATTATAAAGACGGAGATATTTCATATAATCCAGAGGTGCCG

AGTTATTCGGCTAAATATCAATTAACTAATGATGATTATAATGTAAAACAATTACGCAAA

AGATATGATATACCGACGAGTAAAGCTCCAAAGTTATTGTTAAAAGGTTCAGGGAATTTA

AAAGGCTCATCAGTTGGATATAAAGATATTGAATTTACGTTTGTAGAGAAAAAAGAAGAA

AATATATACTTTAGTGATAGCTTAGATTATAAAAAAAGCGGAGATGTATAA amino acid sequence
MMKRLNKLVLGIIFLFLVISITAGCGIGKEAEVKKSFEKTLSMYPIKNLEDLYDKEGYRD

DQFDKNDKGTWIINSEMVIQPNNEDMVAKGMVLYMNRNTKTTNGYYYVDVTKDEDEGKPH

DNEKRYPVKMVDNKIIPTKEIKDEKIKKEIENFKFFVQYGDFKNLKNYKDGDISYNPEVP

SYSAKYQLTNDDYNVKQLRKRYDIPTSKAPKLLLKGSGNLKGSSVGYKDIEFTFVEKKEE

NIYFSDSLDYKKSGDV

10.
Lpp-csA1: sequence of the Lpp-csA1 gene (SEQ ID NO: 10) and
lipidated CsA1 protein (SEQ ID NO: 29)
DNA sequence
ATGAAAGCTACTAAACTGGTACTGGGCGCGGTAATCCTGGGTTCTACTCTGCTGGCAGGT

TGCGGCATAGGTAAAGAAGCGGAAGTTAAGAAAAGCTTTGAAAAAACATTGAGTATGTAC

CCTATTAAAAATCTAGAGGATTTATACGATAAGGAAGGCTATCGTGATGATCAGTTTGAT

AAAAATGATAAAGGTACATGGATTATAAATTCTGAAATGGTTATTCAACCTAATAATGAA

GATATGGTAGCTAAAGGCATGGTTCTATATATGAATAGAAATACCAAAACAACAAATGGT

TACTACTATGTCGATGTGACTAAGGACGAGGATGAAGGAAAACCGCACGACAATGAAAAA

AGATATCCGGTTAAAATGGTCGATAATAAAATCATTCCAACAAAAGAAATTAAAGATGAA

AAAATAAAAAAAGAAATCGAAAACTTTAAGTTCTTTGTTCAATATGGCGACTTTAAAAAT

TTGAAAAATTATAAAGACGGAGATATTTCATATAATCCAGAGGTGCCGAGTTATTCGGCT

AAATATCAATTAACTAATGATGATTATAATGTAAAACAATTACGCAAAAGATATGATATA

CCGACGAGTAAAGCTCCAAAGTTATTGTTAAAAGGTTCAGGGAATTTAAAAGGCTCATCA

GTTGGATATAAAGATATTGAATTTACGTTTGTAGAGAAAAAAGAAGAAAATATATACTTT

AGTGATAGCTTAGATTATAAAAAAAGCGGAGATGTATAA

Amino acid sequence
MKATKLVLGAVILGSTLLAGCGIGKEAEVKKSFEKTLSMYPIKNLEDLYDKEGYRDDQFD

KNDKGTWIINSEMVIQPNNEDMVAKGMVLYMNRNIKTINGYYYVDVTKDEDEGKPHDNEK

RYPVKMVDNKIIPTKEIKDEKIKKEIENFKFFVQYGDFKNLKNYKDGDISYNPEVPSYSA

KYQLTNDDYNVKQLRKRYDIPTSKAPKLLLKGSGNLKGSSVGYKDIEFTFVEKKEENIYF

SDSLDYKKSGDV*

11.
Lpp-C > A csA1: sequence of the Lpp-C > A csA1 gene (SEQ ID
NO: 11) and non-lipidated CsA1 protein (SEQ ID NO: 30)
DNA sequence
ATGAAAGCTACTAAACTGGTACTGGGCGCGGTAATCCTGGGTTCTACTCTGCTGGCAGGT gcCGGCATAGGTAAAGAAGCGGAAGTTAAGAAAAGCTTTGAAAAAACATTGAGTATGTAC

CCTATTAAAAATCTAGAGGATTTATACGATAAGGAAGGCTATCGTGATGATCAGTTTGAT

AAAAATGATAAAGGTACATGGATTATAAATTCTGAAATGGTTATTCAACCTAATAATGAA

GATATGGTAGCTAAAGGCATGGTTCTATATATGAATAGAAATACCAAAACAACAAATGGT

TACTACTATGTCGATGTGACTAAGGACGAGGATGAAGGAAAACCGCACGACAATGAAAAA

AGATATCCGGTTAAAATGGTCGATAATAAAATCATTCCAACAAAAGAAATTAAAGATGAA

AAAATAAAAAAAGAAATCGAAAACTTTAAGTTCTTTGTTCAATATGGCGACTTTAAAAAT

TTGAAAAATTATAAAGACGGAGATATTTCATATAATCCAGAGGTGCCGAGTTATTCGGCT

AAATATCAATTAACTAATGATGATTATAATGTAAAACAATTACGCAAAAGATATGATATA

CCGACGAGTAAAGCTCCAAAGTTATTGTTAAAAGGTTCAGGGAATTTAAAAGGCTCATCA

-continued

GTTGGATATAAAGATATTGAATTTACGTTTGTAGAGAAAAAAGAAGAAAATATATACTTT

AGTGATAGCTTAGATTATAAAAAAAGCGGAGATGTATAA

Amino acid sequence
MKATKLVLGAVILGSTLLAGAGIGKEAEVKKSFEKTLSMYPIKNLEDLYDKEGYRDDQFD

KNDKGTWIINSEMVIQPNNEDMVAKGMVLYMNRNTKTTNGYYYVDVTKDEDEGKPHDNEK

RYPVKMVDNKIIPTKEIKDEKIKKEIENFKFFVQYGDFKNLKNYKDGDISYNPEVPSYSA

KYQLTNDDYNVKQLRKRYDIPTSKAPKLLLKGSGNLKGSSVGYKDIEFTFVEKKEENIYF

SDSLDYKKSGDV*

12.
Spa$_{KKAA}$: sequence of the spa$_{KKAA}$ synthetic gene (SEQ ID NO: 12)
and Spa$_{KKAA}$ protein (SEQ ID NO: 31)
DNA sequence
GCACAGCATGATGAAGCCAAAAAAAACGCCTTTTATCAGGTTCTGAATATGCCGAATCTG

AATGCCGATCAGCGTAATGGTTTTATTCAGAGCCTGAAAGCAGCACCGAGCCAGAGCGCA

AATGTTCTGGGTGAAGCACAGAAACTGAATGATAGCCAGGCACCGAAAGCAGATGCCAAA

CGCAACAATTTTAACAAAGATAAAAAAAGCGCGTTTTATGAAATCCTGAACATGCCTAAC

CTGAATGAAGCACAGCGCAATGGCTTTATCCAGTCTCTGAAAGCCGCACCGTCACAGTCT

ACCAATGTGCTGGGCGAAGCGAAAAAACTGAACGAATCCCAGGCTCCGAAAGCCGATAAT

AACTTCAACAAAGAGAAAAAAAACGCCTTTTATGAAATTCTGAATATGCCAAATCTGAAC

GAAGAACAGCGTAACGGTTTTATTCAGTCACTGAAAGCGGCTCCTAGCCAGTCTGCAAAT

CTGCTGTCTGAAGCCAAAAAACTGAATGAAAGTCAGGCACCTAAAGCGGATAACAAATTT

AACAAAGAGAAAAAAAACGCATTTTATGAAATCCTGCATCTGCCGAATCTGAATGAAGAA

CAGCGCAACGGCTTTATTCAGAGTCTGAAAGCCGCTCCGTCCCAGAGCGCCAACCTGCTG

GCCGAAGCAAAAAAACTGAATGATGCGCAGGCTCCGAAAGCAGATAACAAATTTAACAAA

GAGAAAAAAAACGCCTTCTATGAAATTCTGCACCTGCCTAACCTGACCGAAGAACAGCGT

AATGGTTTTATCCAGTCCCTGAAAGCGGCTCCTAGCGTTAGCAAAGAAATCCTGGCAGAG

GCCAAAAAACTGAACGACGCACAGGCACCTAAA

Amino acid sequence
AQHDEAKKNAFYQVLNMPNLNADQRNGFIQSLKAAPSQSANVLGEAQKLNDSQAPKADAK

RNNFNKDKKSAFYEILNMPNLNEAQRNGFIQSLKAAPSQSTNVLGEAKKLNESQAPKADN

NFNKEKKNAFYEILNMPNLNEEQRNGFIQSLKAAPSQSANLLSEAKKLNESQAPKADNKF

NKEKKNAFYEILHLPNLNEEQRNGFIQSLKAAPSQSANLLAEAKKLNDAQAPKADNKFNK

EKKNAFYEILHLPNLTEEQRNGFIQSLKAAPSVSKEILAEAKKLNDAQAPK

13,
Lpp-spa$_{KKAA}$: sequence of the Lpp-spa$_{KKAA}$ gene (SEQ ID NO: 13)
and lipidated Spa$_{KKAA}$ protein (SEQ ID NO: 32)
DNA sequence
ATGATGAAAGCTACTAAACTGGTACTGGGCGCGGTAATCCTGGGTTCTACTCTGCTGGCA GGTtgCGCACAGCATGATGAAGCCAAAAAAAACGCCTTTTATCAGGTTCTGAATATGCCG

AATCTGAATGCCGATCAGCGTAATGGTTTTATTCAGAGCCTGAAAGCAGCACCGAGCCAG

AGCGCAAATGTTCTGGGTGAAGCACAGAAACTGAATGATAGCCAGGCACCGAAAGCAGAT

GCCAAACGCAACAATTTTAACAAAGATAAAAAAAGCGCGTTTTATGAAATCCTGAACATG

CCTAACCTGAATGAAGCACAGCGCAATGGCTTTATCCAGTCTCTGAAAGCCGCACCGTCA

CAGTCTACCAATGTGCTGGGCGAAGCGAAAAAACTGAACGAATCCCAGGCTCCGAAAGCC

GATAATAACTTCAACAAAGAGAAAAAAAACGCCTTTTATGAAATTCTGAATATGCCAAAT

-continued

```
CTGAACGAAGAACAGCGTAACGGTTTTATTCAGTCACTGAAAGCGGCTCCTAGCCAGTCT

GCAAATCTGCTGTCTGAAGCCAAAAAACTGAATGAAAGTCAGGCACCTAAAGCGGATAAC

AAATTTAACAAAGAGAAAAAAAACGCATTTTATGAAATCCTGCATCTGCCGAATCTGAAT

GAAGAACAGCGCAACGGCTTTATTCAGAGTCTGAAAGCCGCTCCGTCCCAGAGCGCCAAC

CTGCTGGCCGAAGCAAAAAAACTGAATGATGCGCAGGCTCCGAAAGCAGATAACAAATTT

AACAAAGAGAAAAAAAACGCCTTCTATGAAATTCTGCACCTGCCTAACCTGACCGAAGAA

CAGCGTAATGGTTTTATCCAGTCCCTGAAAGCGGCTCCTAGCGTTAGCAAAGAAATCCTG

GCAGAGGCCAAAAAACTGAACGACGCACAGGCACCTAAATAA
```

Amino acid sequence
MKATKLVLGAVILGSTLLAGCAQHDEAKKNAFYQVLNMPNLNADQRNGFIQSLKAAPSQS

ANVLGEAQKLNDSQAPKADAKRNNFNKDKKSAFYEILNMPNLNEAQRNGFIQSLKAAPSQ

STNVLGEAKKLNESQAPKADNNFNKEKKNAFYEILNMPNLNEEQRNGFIQSLKAAPSQSA

NLLSEAKKLNESQAPKADNKFNKEKKNAFYEILHLPNLNEEQRNGFIQSLKAAPSQSANL

LAEAKKLNDAQAPKADNKFNKEKKNAFYEILHLPNLTEEQRNGFIQSLKAAPSVSKEILA

EAKKLNDAQAPK*

14.
Lpp-C > A spa$_{KKAA}$: sequence of the Lpp-C > A spa$_{KKAA}$ gene (SEQ ID NO: 14) and non-lipidated Spa$_{KKAA}$ protein (SEQ ID NO: 33)
DNA sequence
```
ATGATGAAAGCTACTAAACTGGTACTGGGCGCGGTAATCCTGGGTTCTACTCTGCTGGCA

GGTGCCGCACAGCATGATGAAGCCAAAAAAAACGCCTTTTATCAGGTTCTGAATATGCCG

AATCTGAATGCCGATCAGCGTAATGGTTTTATTCAGAGCCTGAAAGCAGCACCGAGCCAG

AGCGCAAATGTTCTGGGTGAAGCACAGAAACTGAATGATAGCCAGGCACCGAAAGCAGAT

GCCAAACGCAACAATTTTAACAAAGATAAAAAAAGCGCGTTTTATGAAATCCTGAACATG

CCTAACCTGAATGAAGCACAGCGCAATGGCTTTATCCAGTCTCTGAAAGCCGCACCGTCA

CAGTCTACCAATGTGCTGGGCGAAGCGAAAAAACTGAACGAATCCCAGGCTCCGAAAGCC

GATAATAACTTCAACAAAGAGAAAAAAAACGCCTTTTATGAAATTCTGAATATGCCAAAT

CTGAACGAAGAACAGCGTAACGGTTTTATTCAGTCACTGAAAGCGGCTCCTAGCCAGTCT

GCAAATCTGCTGTCTGAAGCCAAAAAACTGAATGAAAGTCAGGCACCTAAAGCGGATAAC

AAATTTAACAAAGAGAAAAAAAACGCATTTTATGAAATCCTGCATCTGCCGAATCTGAAT

GAAGAACAGCGCAACGGCTTTATTCAGAGTCTGAAAGCCGCTCCGTCCCAGAGCGCCAAC

CTGCTGGCCGAAGCAAAAAAACTGAATGATGCGCAGGCTCCGAAAGCAGATAACAAATTT

AACAAAGAGAAAAAAAACGCCTTCTATGAAATTCTGCACCTGCCTAACCTGACCGAAGAA

CAGCGTAATGGTTTTATCCAGTCCCTGAAAGCGGCTCCTAGCGTTAGCAAAGAAATCCTG

GCAGAGGCCAAAAAACTGAACGACGCACAGGCACCTAAATAA
```

Amino acid sequence
MKATKLVLGAVILGSTLLAGAAQHDEAKKNAFYQVLNMPNLNADQRNGFIQSLKAAPSQS

ANVLGEAQKLNDSQAPKADAKRNNFNKDKKSAFYEILNMPNLNEAQRNGFIQSLKAAPSQ

STNVLGEAKKLNESQAPKADNNFNKEKKNAFYEILNMPNLNEEQRNGFIQSLKAAPSQSA

NLLSEAKKLNESQAPKADNKFNKEKKNAFYEILHLPNLNEEQRNGFIQSLKAAPSQSANL

LAEAKKLNDAQAPKADNKFNKEKKNAFYEILHLPNLTEEQRNGFIQSLKAAPSVSKEILA

EAKKLNDAQAPK*

15.
LukE: sequence of the lukE synthetic gene (SEQ ID NO: 15) and
LukE protein (SEQ ID NO: 34)
DNA sequence
TTGTCAGTAGGACTGATTGCACCTTTAGCATCTCCGATTCAAGAATCTAGAGCAAATACT

AATATTGAAAATATTGGTGATGGTGCTGAAGTAATCAAACGTACGGAGGATGTAAGTAGT

AAGAAATGGGGCGTTACTCAAAATGTCCAATTCGACTTTGTAAAAGATAAAAAATATAAC

AAAGACGCTTTAATTGTTAAAATGCAAGGTTTTATTAATTCCAGAACTTCATTTTCAGAT

GTGAAGGGTAGTGGATATGAATTAACTAAACGAATGATTTGGCCATTCCAATATAATATA

GGACTGACGACTAAAGATCCAAATGTTAGCTTAATCAATTACCTTCCTAAAAACAAATA

GAAACTACTGATGTTGGTCAAACATTAGGATATAACATTGGAGGTAATTTCCAGTCAGCA

CCATCTATAGGTGGCAATGGCTCATTTAATTATTCTAAAACAATTAGTTATACCCAAAAG

AGTTATGTCAGTGAAGTAGACAAGCAAAACTCAAAATCTGTTAAATGGGGTGTTAAAGCA

AACGAATTTGTTACGCCTGATGGAAAAAAATCTGCGCATGATAGATATTTATTCGTACAA

AGTCCAAATGGTCCAACAGGTTCAGCAAGAGAATATTTTGCTCCTGATAATCAATTGCCA

CCTTTAGTTCAAAGTGGCTTTAATCCATCGTTTATCACTACACTATCACATGAAAAAGGT

TCAAGTGATACGAGTGAATTTGAAATTTCATATGGTAGAAACTTAGATATTACATATGCG

ACTTTATTCCCTAGAACTGGTATTTACGCAGAAAGAAAGCATAATGCATTTGTAAATAGA

AACTTTGTAGTTAGATATGAAGTTAATTGGAAAACACACGAAATTAAAGTGAAAGGACAT

AATTAA amino acid sequence
NTNIENIGDGAEVIKRTEDVSSKKWGVTQNVQFDFVKDKKYNKDALIVKMQGFINSRTSF

SDVKGSGYELTKRMIWPFQYNIGLTTKDPNVSLINYLPKNKIETTDVGQTLGYNIGGNFQ

SAPSIGGNGSFNYSKTISYTQKSYVSEVDKQNSKSVKWGVKANEFVTPDGKKSAHDRYLF

VQSPNGPTGSAREYFAPDNQLPPLVQSGFNPSFITTLSHEKGSSDTSEFEISYGRNLDIT

YATLFPRTGIYAERKHNAFVNRNFVVRYEVNWKTHEIKVKGHN*

16.
Lpp-lukE: sequence of the Lpp-lukE gene (SEQ ID NO: 16) and
lipidated LukE protein (SEQ ID NO: 35)
DNA sequence
ATGAAAGCTACTAAACTGGTACTGGGCGCGGTAATCCTGGGTTCTACTCTGCTGGCAGGT tgcaatactAATATTGAAAATATTGGTGATGGTGCTGAAGTAATCAAACGTACGGAGGAT

GTAAGTAGTAAGAAATGGGGCGTTACTCAAAATGTCCAATTCGACTTTGTAAAAGATAAA

AAATATAACAAAGACGCTTTAATTGTTAAAATGCAAGGTTTTATTAATTCCAGAACTTCA

TTTTCAGATGTGAAGGGTAGTGGATATGAATTAACTAAACGAATGATTTGGCCATTCCAA

TATAATATAGGACTGACGACTAAAGATCCAAATGTTAGCTTAATCAATTACCTTCCTAAA

AACAAAATAGAAACTACTGATGTTGGTCAAACATTAGGATATAACATTGGAGGTAATTTC

CAGTCAGCACCATCTATAGGTGGCAATGGCTCATTTAATTATTCTAAAACAATTAGTTAT

ACCCAAAAGAGTTATGTCAGTGAAGTAGACAAGCAAAACTCAAAATCTGTTAAATGGGGT

GTTAAAGCAAACGAATTTGTTACGCCTGATGGAAAAAAATCTGCGCATGATAGATATTTA

TTCGTACAAAGTCCAAATGGTCCAACAGGTTCAGCAAGAGAATATTTTGCTCCTGATAAT

CAATTGCCACCTTTAGTTCAAAGTGGCTTTAATCCATCGTTTATCACTACACTATCACAT

GAAAAAGGTTCAAGTGATACGAGTGAATTTGAAATTTCATATGGTAGAAACTTAGATATT

ACATATGCGACTTTATTCCCTAGAACTGGTATTTACGCAGAAAGAAAGCATAATGCATTT

GTAAATAGAAACTTTGTAGTTAGATATGAAGTTAATTGGAAAACACACGAAATTAAAGTG

AAAGGACATAATTAATAA

Amino acid sequence
MKATKLVLGAVILGSTLLAGCNTNIENIGDGAEVIKRTEDVSSKKWGVTQNVQFDFVKDK

KYNKDALIVKMQGFINSRTSFSDVKGSGYELTKRMIWPFQYNIGLTTKDPNVSLINYLPK

NKIETTDVGQTLGYNIGGNFQSAPSIGGNGSFNYSKTISYTQKSYVSEVDKQNSKSVKWG

VKANEFVTPDGKKSAHDRYLFVQSPNGPTGSAREYFAPDNQLPPLVQSGFNPSFITTLSH

EKGSSDTSEFEISYGRNLDITYATLFPRTGIYAERKHNAFVNRNFVVRYEVNWKTHEIKV

KGHN

17.
Lpp-C > A lukE: sequence of the Lpp-C > A lukE gene (SEQ ID
NO: 17) and non-lipidated LukE protein (SEQ ID NO: 36)
DNA sequence
ATGAAAGCTACTAAACTGGTACTGGGCGCGGTAATCCTGGGTTCTACTCTGCTGGCAGGT GCcAATACTAATATTGAAAATATTGGTGATGGTGCTGAAGTAATCAAACGTACGGAGGAT

GTAAGTAGTAAGAAATGGGGCGTTACTCAAAATGTCCAATTCGACTTTGTAAAAGATAAA

AAATATAACAAAGACGCTTTAATTGTTAAAATGCAAGGTTTTATTAATTCCAGAACTTCA

TTTTCAGATGTGAAGGGTAGTGGATATGAATTAACTAAACGAATGATTTGGCCATTCCAA

TATAATATAGGACTGACGACTAAAGATCCAAATGTTAGCTTAATCAATTACCTTCCTAAA

AACAAAATAGAAACTACTGATGTTGGTCAAACATTAGGATATAACATTGGAGGTAATTTC

CAGTCAGCACCATCTATAGGTGGCAATGGCTCATTTAATTATTCTAAAACAATTAGTTAT

ACCCAAAAGAGTTATGTCAGTGAAGTAGACAAGCAAAACTCAAAATCTGTTAAATGGGGT

GTTAAAGCAAACGAATTTGTTACGCCTGATGGAAAAAAATCTGCGCATGATAGATATTTA

TTCGTACAAAGTCCAAATGGTCCAACAGGTTCAGCAAGAGAATATTTTGCTCCTGATAAT

CAATTGCCACCTTTAGTTCAAAGTGGCTTTAATCCATCGTTTATCACTACACTATCACAT

GAAAAAGGTTCAAGTGATACGAGTGAATTTGAAATTTCATATGGTAGAAACTTAGATATT

ACATATGCGACTTTATTCCCTAGAACTGGTATTTACGCAGAAAGAAAGCATAATGCATTT

GTAAATAGAAACTTTGTAGTTAGATATGAAGTTAATTGGAAAACACACGAAATTAAAGTG

AAAGGACATAATTAATAA

Amino acid sequence
MKATKLVLGAVILGSTLLAGANTNIENIGDGAEVIKRTEDVSSKKWGVTQNVQFDFVKDK

KYNKDALIVKMQGFINSRTSFSDVKGSGYELTKRMIWPFQYNIGLTTKDPNVSLINYLPK

NKIETTDVGQTLGYNIGGNFQSAPSIGGNGSFNYSKTISYTQKSYVSEVDKQNSKSVKWG

VKANEFVTPDGKKSAHDRYLFVQSPNGPTGSAREYFAPDNQLPPLVQSGFNPSFITTLSH

EKGSSDTSEFEISYGRNLDITYATLFPRTGIYAERKHNAFVNRNFVVRYEVNWKTHEIKV

KGHN

18.
Lambda-red cassette gene sequence (SEQ ID NO: 18)
CATCGATTTATTATGACAACTTGACGGCTACATCATTCACTTTTTCTTCACAACCGGCAC

GGAACTCGCTCGGGCTGGCCCCGGTGCATTTTTTAAATACCCGCGAGAAATAGAGTTGAT

CGTCAAAACCAACATTGCGACCGACGGTGGCGATAGGCATCCGGGTGGTGCTCAAAAGCA

GCTTCGCCTGGCTGATACGTTGGTCCTCGCGCCAGCTTAAGACGCTAATCCCTAACTGCT

GGCGGAAAAGATGTGACAGACGCGACGGCGACAAGCAAACATGCTGTGCGACGCTGGCGA

TATCAAAATTGCTGTCTGCCAGGTGATCGCTGATGTACTGACAAGCCTCGCGTACCCGAT

-continued

```
TATCCATCGGTGGATGGAGCGACTCGTTAATCGCTTCCATGCGCCGCAGTAACAATTGCT

CAAGCAGATTTATCGCCAGCAGCTCCGAATAGCGCCCTTCCCCTTGCCCGGCGTTAATGA

TTTGCCCAAACAGGTCGCTGAAATGCGGCTGGTGCGCTTCATCCGGGCGAAAGAACCCCG

TATTGGCAAATATTGACGGCCAGTTAAGCCATTCATGCCAGTAGGCGCGCGGACGAAAGT

AAACCCACTGGTGATACCATTCGCGAGCCTCCGGATGACGACCGTAGTGATGAATCTCTC

CTGGCGGGAACAGCAAAATATCACCCGGTCGGCAAACAAATTCTCGTCCCTGATTTTTCA

CCACCCCCTGACCGCGAATGGTGAGATTGAGAATATAACCTTTCATTCCCAGCGGTCGGT

CGATAAAAAAATCGAGATAACCGTTGGCCTCAATCGGCGTTAAACCCGCCACCAGATGGG

CATTAAACGAGTATCCCGGCAGCAGGGGATCATTTTGCGCTTCAGCCATACTTTTCATAC

TCCCGCCATTCAGAGAAGAAACCAATTGTCCATATTGCATCAGACATTGCCGTCACTGCG

TCTTTTACTGGCTCTTCTCGCTAACCAAACCGGTAACCCCGCTTATTAAAAGCATTCTGT

AACAAAGCGGGACCAAAGCCATGACAAAAACGCGTAACAAAAGTGTCTATAATCACGGCA

GAAAAGTCCACATTGATTATTTGCACGGCGTCACACTTTGCTATGCCATAGCATTTTTAT

CCATAAGATTAGCGGATCCTACCTGACGCTTTTTATCGCAACTCTCTACTGTTTCTCCAT

ACCCGTTTTTTTGGGAATTCGAGCTCTAAGGAGGTTATAAAAAATGGATATTAATACTGA

AACTGAGATCAAGCAAAAGCATTCACTAACCCCCTTTCCTGTTTTCCTAATCAGCCCGGC

ATTTCGCGGGCGATATTTTCACAGCTATTTCAGGAGTTCAGCCATGAACGCTTATTACAT

TCAGGATCGTCTTGAGGCTCAGAGCTGGGCGCGTCACTACCAGCAGCTCGCCCGTGAAGA

GAAAGAGGCAGAACTGGCAGACGACATGGAAAAAGGCCTGCCCCAGCACCTGTTTGAATC

GCTATGCATCGATCATTTGCAACGCCACGGGGCCAGCAAAAAATCCATTACCCGTGCGTT

TGATGACGATGTTGAGTTTCAGGAGCGCATGGCAGAACACATCCGGTACATGGTTGAAAC

CATTGCTCACCACCAGGTTGATATTGATTCAGAGGTATAAAACGAATGAGTACTGCACTC

GCAACGCTGGCTGGGAAGCTGGCTGAACGTGTCGGCATGGATTCTGTCGACCCACAGGAA

CTGATCACCACTCTTCGCCAGACGGCATTTAAAGGTGATGCCAGCGATGCGCAGTTCATC

GCATTACTGATCGTTGCCAACCAGTACGGCCTTAATCCGTGGACGAAAGAAATTTACGCC

TTTCCTGATAAGCAGAATGGCATCGTTCCGGTGGTGGGCGTTGATGGCTGGTCCCGCATC

ATCAATGAAAACCAGCAGTTTGATGGCATGGACTTTGAGCAGGACAATGAATCCTGTACA

TGCCGGATTTACCGCAAGGACCGTAATCATCCGATCTGCGTTACCGAATGGATGGATGAA

TGCCGCCGCGAACCATTCAAAACTCGCGAAGGCAGAGAAATCACGGGCCGTGGCAGTCG

CATCCCAAACGGATGTTACGTCATAAAGCCATGATTCAGTGTGCCCGTCTGGCCTTCGGA

TTTGCTGGTATCTATGACAAGGATGAAGCCGAGCGCATTGTCGAAAATACTGCATACACT

GCAGAACGTCAGCCGGAACGCGACATCACTCCGGTTAACGATGAAACCATGCAGGAGATT

AACACTCTGCTGATCGCCCTGGATAAAACATGGGATGACGACTTATTGCCGCTCTGTTCC

CAGATATTTCGCCGCGACATTCGTGCATCGTCAGAACTGACACAGGCCGAAGCAGTAAAA

GCTCTTGGATTCCTGAAACAGAAAGCCGCAGAGCAGAAGGTGGCAGCATGACACCGGACA

TTATCCTGCAGCGTACCGGGATCGATGTGAGAGCTGTCGAACAGGGGATGATGCGTGGC

ACAAATTACGGCTCGGCGTCATCACCGCTTCAGAAGTTCACAACGTGATAGCAAAACCCC

GCTCCGGAAAGAAGTGGCCTGACATGAAAATGTCCTACTTCCACACCCTGCTTGCTGAGG

TTTGCACCGGTGTGGCTCCGGAAGTTAACGCTAAAGCACTGGCCTGGGGAAAACAGTACG

AGAACGACGCCAGAACCCTGTTTGAATTCACTTCCGGCGTGAATGTTACTGAATCCCCGA
```

-continued

```
TCATCTATCGCGACGAAAGTATGCGTACCGCCTGCTCTCCCGATGGTTTATGCAGTGACG

GCAACGGCCTTGAACTGAAATGCCCGTTTACCTCCCGGGATTTCATGAAGTTCCGGCTCG

GTGGTTTCGAGGCCATAAAGTCAGCTTACATGGCCCAGGTGCAGTACAGCATGTGGGTGA

CGCGAAAAAATGCCTGGTACTTTGCCAACTATGACCCGCGTATGAAGCGTGAAGGCCTGC

ATTATGTCGTGATTGAGCGGGATGAAAAGTACATGGCGAGTTTTGACGAGATCGTGCCGG

AGTTCATCGAAAAAATGGACGAGGCACTGGCTGAAATTGGTTTTGTATTTGGGGAGCAAT

GGCGATGA
```

19.
Kanamycin-sacB cassette gene cassette (SEQ ID NO: 19)
```
GGGCACCAATAACTGCCTTAAAAAAAATGATTGAACAAGATGGATTGCACGCAGGTTCTC

CGGCCGCTTGGGTGGAGAGGCTATTCGGCTATGACTGGGCACAACAGACAATCGGCTGCT

CTGATGCCGCCGTGTTCCGGCTGTCAGCGCAGGGGCGCCCGGTTCTTTTTGTCAAGACCG

ACCTGTCCGGTGCCCTGAATGAACTGCAGGACGAGGCAGCGCGGCTATCGTGGCTGGCCA

CGACGGGCGTTCCTTGCGCAGCTGTGCTCGACGTTGTCACTGAAGCGGGAAGGGACTGGC

TGCTATTGGGCGAAGTGCCGGGGCAGGATCTCCTGTCATCTCACCTTGCTCCTGCCGAGA

AAGTATCCATCATGGCTGATGCAATGCGGCGGCTGCATACGCTTGATCCGGCTACCTGCC

CATTCGACCACCAAGCGAAACATCGCATCGAGCGAGCACGTACTCGGATGGAAGCCGGTC

TTGTCGATCAGGATGATCTGGACGAAGAGCATCAGGGGCTCGCGCCAGCCGAACTGTTCG

CCAGGCTCAAGGCGCGCATGCCCGACGGCGAGGATCTCGTCGTGACCCATGGCGATGCCT

GCTTGCCGAATATCATGGTGGAAAATGGCCGCTTTTCTGGATTCATCGACTGTGGCCGGC

TGGGTGTGGCGGACCGCTATCAGGACATAGCGTTGGCTACCCGTGATATTGCTGAAGAGC

TTGGCGGCGAATGGGCTGACCGCTTCCTCGTGCTTTACGGTATCGCCGCTCCCGATTCGC

AGCGCATCGCCTTCTATCGCCTTCTTGACGAGTTCTTCTGATTTAGCTTCCTTAGCTCCT

GAAAATCTCGATAACTCAAAAAATACGCCCGGTAGTGATCTTATTTCATTATGGTGAAAG

TTGGAACCTCTTACGTGCCGATCAACGTCTCACGGGATCCTTAATTAAGTCTAGAGTCGA

CTGTTTAAACCTGCAGATCCTTTTTAACCCATCACATATACCTGCCGTTCACTATTATTT

AGTGAAATGAGATATTATGATATTTTCTGAATTGTGATTAAAAAGGCAACTTTATGCCCA

TGCAACAGAAACTATAAAAAATACAGAGAATGAAAAGAAACAGATAGATTTTTTAGTTCT

TTAGGCCCGTAGTCTGCAAATCCTTTTATGATTTTCTATCAAACAAAAGAGGAAAATAGA

CCAGTTGCAATCCAAACGAGAGTCTAATAGAATGAGGTCGAAAAGTAAATCGCGCGGGTT

TGTTACTGATAAAGCAGGCAAGACCTAAAATGTGTAAAGGGCAAAGTGTATACTTTGGCG

TCACCCCTTACATATTTTAGGTCTTTTTTTATTGTGCGTAACTAACTTGCCATCTTCAAA

CAGGAGGGCTGGAAGAAGCAGACCGCTAACACAGTACATAAAAAAGGAGACATGAACGAT

GAACATCAAAAAGTTTGCAAAACAAGCAACAGTATTAACCTTTACTACCGCACTGCTGGC

AGGAGGCGCAACTCAAGCGTTTGCGAAAGAAACGAACCAAAAGCCATATAAGGAAACATA

CGGCATTTCCCATATTACACGCCATGATATGCTGCAAATCCCTGAACAGCAAAAAAATGA

AAAATATCAAGTTCCTGAATTCGATTCGTCCACAATTAAAAATATCTCTTCTGCAAAAGG

CCTGGACGTTTGGGACAGCTGGCCATTACAAAACGCTGACGGCACTGTCGCAAACTATCA

CGGCTACCACATCGTCTTTGCATTAGCCGGAGATCCTAAAAATGCGGATGACACATCGAT

TTACATGTTCTATCAAAAAGTCGGCGAAACTTCTATTGACAGCTGGAAAAACGCTGGCCG

CGTCTTTAAAGACAGCGACAAATTCGATGCAAATGATTCTATCCTAAAAGACCAAACACA

AGAATGGTCAGGTTCAGCCACATTTACATCTGACGGAAAAATCCGTTTATTCTACACTGA
```

-continued

TTTCTCCGGTAAACATTACGGCAAACAAACACTGACAACTGCACAAGTTAACGTATCAGC

ATCAGACAGCTCTTTGAACATCAACGGTGTAGAGGATTATAAATCAATCTTTGACGGTGA

CGGAAAAACGTATCAAAATGTACAGCAGTTCATCGATGAAGGCAACTACAGCTCAGGCGA

CAACCATACGCTGAGAGATCCTCACTACGTAGAAGATAAAGGCCACAAATACTTAGTATT

TGAAGCAAACACTGGAACTGAAGATGGCTACCAAGGCGAAGAATCTTTATTTAACAAAGC

ATACTATGGCAAAAGCACATCATTCTTCCGTCAAGAAAGTCAAAAACTTCTGCAAAGCGA

TAAAAAACGCACGGCTGAGTTAGCAAACGGCGCTCTCGGTATGATTGAGCTAAACGATGA

TTACACACTGAAAAAAGTGATGAAACCGCTGATTGCATCTAACACAGTAACAGATGAAAT

TGAACGCGCGAACGTCTTTAAAATGAACGGCAAATGGTACCTGTTCACTGACTCCCGCGG

ATCAAAAATGACGATTGACGGCATTACGTCTAACGATATTTACATGCTTGGTTATGTTTC

TAATTCTTTAACTGGCCCATACAAGCCGCTGAACAAAACTGGCCTTGTGTTAAAAATGGA

TCTTGATCCTAACGATGTAACCTTTACTTACTCACACTTCGCTGTACCTCAAGCGAAAGG

AAACAATGTCGTGATTACAAGCTATATGACAAACAGAGGATTCTACGCAGACAAACAATC

AACGTTTGCGCCAAGCTTCCTGCTGAACATCAAAGGCAAGAAAACATCTGTTGTCAAAGA

CAGCATCCTTGAACAAGGACAATTAACAGTTAACAAATAAAAACGCAAAGAAAATGCCG

AT

---

The invention claimed is:

1. A method of preparing an outer membrane vesicle (OMV) from a Gram-negative bacterium, wherein
said OMV comprises a lipoprotein consisting of a heterologous protein which is a bacterial, viral, parasitic, cancer protein or polypeptide-carrying an acylated N-terminal cysteine,
said heterologous protein is fused to a lipoprotein leader sequence, said lipoprotein leader sequence causing said heterologous proteins to become lipidated,
and
said OMV is capable of eliciting an immune response to the heterologous protein when administered to a mammal,
said method comprising the following steps:
(i) expressing, in a Gram-negative bacterium, the heterologous protein fused to said leader sequence carrying a C-terminal Cysteine, wherein the leader sequence comprises the sequence Leu-(Ala/Ser)-(Gly/Ala)-Cys (lipobox), SEQ ID NO:111; and
(ii) isolating the OMV containing the heterologous protein.

2. The method according to claim 1, wherein the leader sequence is the murine lipoprotein Lpp MKATKLVLGAVILGSTLLAGC, SEQ ID NO:83, according to the one-letter amino acid code.

3. The method according to claim 1, wherein said Gram-negative bacterium is a hyperblebbing strain of the Gram-negative bacterium.

4. The method according to claim 1, wherein the Gram-negative bacterium carries mutations at the ompA, msbB and pagP genes causing inactivation or deletion thereof.

5. The method according to claim 1, wherein the Gram-negative bacterium is selected from the group consisting of *Escherichia coli, Neisseria menigitidis, Salmonella* sp. and *Shigella* sp.

6. The method according to claim 1, wherein the heterologous protein is expressed in the Gram-negative bacterium by means of an expression vector comprising a nucleic acid encoding the heterologous protein linked to a nucleic acid encoding a signal sequence of a lipoprotein.

7. The method according to claim 6, wherein said vector is either a plasmid or a vector which is integrated into the genome of the host strain producing the OMV.

8. The method of claim 1, wherein the heterologous protein is selected from: double mutant of extracellular cholesterol depending streptolysin O (Slo-dm) from *Streptococcus pyogenes*; HlaH35L from *Staphylococcus aureus*; SpaKKAA antigen from *Staphylococcus aureus*; and LukE antigen from *Staphylococcus aureus*.

* * * * *

SEQUENCE LISTING

<160> NUMBER OF SEQ ID NOS: 111

<210> SEQ ID NO 1
<211> LENGTH: 1680
<212> TYPE: DNA
<213> ORGANISM: Artificial Sequence
<220> FEATURE:
<223> OTHER INFORMATION: recombinant plasmidic DNA

<400> SEQUENCE: 1
atgaaagcta ctaaactggt actgggcgcg gtaatcctgg gttctactct gctggcaggt      60
tgcaacaaac aaaacactgc tagtacagaa accacaacga caaatgagca accaaagcca     120
gaaagtagtg agctaactac tgaaaaagca ggtcagaaaa cggatgatat gcttaactct     180
aacgatatga ttaagcttgc tcccaaagaa atgccactag aatctgcaga aaaagaagaa     240
aaaaagtcag aagacaaaaa aaagagcgaa gaagatcaca ctgaagaaat caatgacaag     300
atttattcac taaattataa tgagcttgaa gtacttgcta aaaatggtga accattgaa      360 aattttgttc ctaaagaagg cgttaagaaa gctgataaat ttattgtcat tgaaagaaag     420
aaaaaaaata tcaacactac accagtcgat atttccatta ttgactctgt cactgatagg     480
acctatccag cagcccttca gctggctaat aaaggttta ccgaaaacaa accagacgcg      540
gtagtcacca agcgaaaccc acaaaaaatc catattgatt taccaggtat gggagacaaa     600
gcaacggttg aggtcaatga ccctacctat gccaatgttt caacagctat tgataatctt     660
gttaaccaat ggcatgataa ttattctggt ggtaatacgc ttcctgccag aacacaatat     720
actgaatcaa tggtatattc taagtcacag attgaggcag ctctaaatgt taatagcaaa     780
atcttagatg gtactttagg cattgatttc aagtcgattt caaaggtga aaagaaggtg      840 atgattgcag catacaagca aattttttac accgtatcag caaaccttcc taataatcct     900
gcggatgtgt ttgataaatc ggtgaccttt aaagagttgc aacgaaaagg tgtcagcaat     960

```
gaagctccgc cactctttgt gagtaacgta gcctatggtc gaactgtttt tgtcaaacta    1020
gaaacaagtt ctaaaagtaa tgatgttgaa gcggccttta gtgcagctct aaaaggaaca    1080
gatgttaaaa ctaatggaaa atattctgat atcttagaaa atagctcatt tacagctgtc    1140
gttttaggag gagatgctgc agagcacaat aaggtagtca caaaagactt tgatgttatt    1200
agaaacgtta tcaaagacaa tgctaccttc agtagaaaaa acctagctta tcctatttca    1260
tacaccagtg ttttccttaa aaataataaa attgcgggtg tcaataacag aactgaatac    1320
gttgaaacaa catctaccga gtacactagt ggaaaaatta acctgtctca tcaaggcgcg    1380
tatgttgctc aatatgaaat cctttgggat gaaatcaatt atgatgacaa aggaaaagaa    1440
gtgattacaa aacgacgttg ggacaacaac tggtatagta agacatcacc atttagcaca    1500
gttatcccac taggagctaa ttcacgaaat atccgtatca tggctagaga gtgcactggc    1560
ttagctttcg aatggtggcg aaaagtgatc gacgaaagag atgtgaaact gtctaaagaa    1620
atcaatgtca atatctcagg atcaaccttg agcccatatg gttcgattac ttataagtag    1680

<210> SEQ ID NO 2
<211> LENGTH: 1680
<212> TYPE: DNA
<213> ORGANISM: Artificial Sequence
<220> FEATURE:
<223> OTHER INFORMATION: recombinant plasmidic DNA

<400> SEQUENCE: 2
atgaaagcta ctaaactggt actgggcgcg gtaatcctgg gttctactct gctggcaggt      60
gccaacaaac aaaacactgc tagtacagaa accacaacga caaatgagca accaaagcca     120
gaaagtagtg agctaactac tgaaaaagca ggtcagaaaa cggatgatat gcttaactct     180
aacgatatga ttaagcttgc tcccaaagaa atgccactag aatctgcaga aaagaagaa     240 aaaaagtcag aagacaaaaa aaagagcgaa gaagatcaca ctgaagaaat caatgacaag    300
atttattcac taaattataa tgagcttgaa gtacttgcta aaaatggtga aaccattgaa    360
aattttgttc ctaaagaagg cgttaagaaa gctgataaat ttattgtcat tgaaagaaag    420
aaaaaaaata tcaacactac accagtcgat atttccatta ttgactctgt cactgatagg    480
acctatccag cagcccttca gctggctaat aaaggttttta ccgaaaacaa accagacgcg    540
gtagtcacca agcgaaaccc acaaaaaatc catattgatt taccaggtat gggagacaaa    600
gcaacggttg aggtcaatga ccctacctat gccaatgttt caacagctat tgataatctt    660
gttaaccaat ggcatgataa ttattctggt ggtaatacgc ttcctgccag aacacaatat    720
actgaatcaa tggtatattc taagtcacag attgaggcag ctctaaatgt taatagcaaa    780
atcttagatg gtactttagg cattgatttc aagtcgattt caaaaggtga aaagaaggtg    840
atgattgcag catacaagca aatttttttac accgtatcag caaaccttcc taataatcct    900
gcggatgtgt ttgataaatc ggtgaccttt aagagttgc aacgaaaagg tgtcagcaat    960
gaagctccgc cactctttgt gagtaacgta gcctatggtc gaactgtttt tgtcaaacta   1020
gaaacaagtt ctaaaagtaa tgatgttgaa gcggccttta gtgcagctct aaaaggaaca   1080
gatgttaaaa ctaatggaaa atattctgat atcttagaaa atagctcatt tacagctgtc   1140
gttttaggag gagatgctgc agagcacaat aaggtagtca caaaagactt tgatgttatt   1200
agaaacgtta tcaaagacaa tgctaccttc agtagaaaaa acctagctta tcctatttca   1260
tacaccagtg ttttccttaa aaataataaa attgcgggtg tcaataacag aactgaatac   1320
```

| | | |
|---|---|---|
| gttgaaacaa catctaccga gtacactagt ggaaaaatta acctgtctca tcaaggcgcg | 1380 |
| tatgttgctc aatatgaaat cctttgggat gaaatcaatt atgatgacaa aggaaaagaa | 1440 |
| gtgattacaa aacgacgttg ggacaacaac tggtatagta agacatcacc atttagcaca | 1500 |
| gttatcccac taggagctaa ttcacgaaat atccgtatca tggctagaga gtgcactggc | 1560 |
| ttagctttcg aatggtggcg aaaagtgatc gacgaaagag atgtgaaact gtctaaagaa | 1620 |
| atcaatgtca atatctcagg atcaaccttg agcccatatg gttcgattac ttataagtag | 1680 |

<210> SEQ ID NO 3
<211> LENGTH: 882
<212> TYPE: DNA
<213> ORGANISM: Artificial Sequence
<220> FEATURE:
<223> OTHER INFORMATION: recombinant plasmidic DNA

<400> SEQUENCE: 3

| | | |
|---|---|---|
| gcagattctg atattaatat taaaaccggt actacagata ttggaagcaa tactacagta | 60 |
| aaaacaggtg atttagtcac ttatgataaa gaaaatggca tgttaaaaaa agtatttat | 120 |
| agttttatcg atgataaaaa tcataataaa aaactgctag ttattagaac gaaaggtacc | 180 |
| attgctggtc aatatagagt ttatagcgaa gaaggtgcta caaaagtgg tttagcctgg | 240 |
| ccttcagcct ttaaggtaca gttgcaacta cctgataatg aagtagctca atatctgat | 300 |
| tactatccaa gaaattcgat tgatacaaaa gagtatatga gtactttaac ttatggattc | 360 |
| aacggtaatg ttactggtga tgatacagga aaaattggcg gccttattgg tgcaaatgtt | 420 |
| tcgattggtc atacactgaa atatgttcaa cctgatttca aaacaatttt agagagccca | 480 |
| actgataaaa aagtaggctg gaaagtgata tttaacaata tggtgaatca aaattgggga | 540 |
| ccatatgata gagattcttg gaacccggta tatggcaatc aactttcat gaaaactaga | 600 |
| aatggctcta tgaaagcagc agataacttc cttgatccta acaaagcaag ttctctatta | 660 |
| tcttcagggt tttcaccaga cttcgctaca gttattacta tggatagaaa agcatccaaa | 720 |
| caacaaacaa atatagatgt aatatacgaa cgagttcgtg atgactacca attgcactgg | 780 |
| acttcaacaa attggaaagg taccaatact aaagataaat ggatagatcg ttcttcagaa | 840 |
| agatataaaa tcgattggga aaagaagaa atgacaaatt aa | 882 |

<210> SEQ ID NO 4
<211> LENGTH: 945
<212> TYPE: DNA
<213> ORGANISM: Artificial Sequence
<220> FEATURE:
<223> OTHER INFORMATION: recombinant plasmidic DNA

<400> SEQUENCE: 4

| | | |
|---|---|---|
| atgaaagcta ctaaactggt actgggcgcg gtaatcctgg gttctatttt gctggcaggt | 60 |
| tgcgcagatt ctgatattaa tattaaaacc ggtactacag atattggaag caatactaca | 120 |
| gtaaaaacag gtgatttagt cacttatgat aaagaaaatg gcatgctcaa aaagtatt | 180 |
| tatagttta tcgatgataa aaatcataat aaaaaactgc tagttattag aacgaaaggt | 240 |
| accattgctg gtcaatatag agtttatagc gaagaaggtg ctaacaaaag tggtttagcc | 300 |
| tggccttcag cctttaaggt acagttgcaa ctacctgata tgaagtagc tcaaatatct | 360 |
| gattactatc caagaaattc gattgataca aaagagtata tgagtacttt aacttatgga | 420 |
| ttcaacggta atgttactgg tgatgataca ggaaaaattg gcggcctta tggtgcaaat | 480 |
| gtttcgattg gtcatacact gaaatatgtt caacctgatt tcaaaacaat tttagagagc | 540 |

```
ccaactgata aaaaagtagg ctggaaagtg atatttaaca atatggtgaa tcaaaattgg       600
ggaccatatg atagagattc ttggaacccg gtatatggca atcaactttt catgaaaact       660
agaaatggct ctatgaaagc agcagataac ttccttgatc ctaacaaagc aagttctcta       720
ttatcttcag ggttttcacc agacttcgct acagttatta ctatggatag aaaagcatcc       780
aaacaacaaa caaatataga tgtaatatac gaacgagttc gtgatgacta ccaattgcac       840
tggacttcaa caaattggaa aggtaccaat actaaagata aatggataga tcgttcttca       900
gaaagatata aaatcgattg ggaaaaagaa gaaatgacaa attaa                      945
```

<210> SEQ ID NO 5
<211> LENGTH: 947
<212> TYPE: DNA
<213> ORGANISM: Artificial Sequence
<220> FEATURE:
<223> OTHER INFORMATION: recombinant plasmidic DNA

<400> SEQUENCE: 5

```
atgatgaaag ctactaaact ggtactgggc gcggtaatcc tgggttctac tctgctggca        60
ggtgccgcag attctgatat taatattaaa accggtacta cagatattgg aagcaatact       120
acagtaaaaa caggtgattt agtcacttat gataaagaaa atggcatgtt aaaaaaagta       180
ttttatagtt ttatcgatga taaaaatcat aataaaaaac tgctagttat tagaacgaaa       240
ggtaccattg ctggtcaata tagagtttat agcgaagaag gtgctaacaa agtggttta       300 gcctggcctt cagcctttaa ggtacagttc aactacctga atgaagta gctcaaatat        360 ctgattacta tccaagaaat tcgattgata caaagagta tatgagtact ttaacttatg       420
gattcaacgg taatgttact ggtgatgata caggaaaaat tggcggcctt attggtgcaa       480
atgtttcgat tggtcataca ctgaaatatg ttcaacctga tttcaaaaca attttagaga       540
gcccaactga taaaaagta ggctggaaag tgatatttaa caatatggtg aatcaaaatt       600
ggggaccata tgatagagat tcttggaacc cggtatatgg caatcaactt ttcatgaaaa       660
ctagaaatgg ctctatgaaa gcagcagata acttccttga tcctaacaaa gcaagttctc       720
tattatcttc agggttttca ccagacttcg ctacagttat tactatggat agaaaagcat       780
ccaaacaaca acaaatata gatgtaatat acgaacgagt tcgtgatgac taccaattgc       840
actggacttc aacaaattgg aaaggtacca atactaaaga taaatggata gatcgttctt       900
cagaaagata taaatcgat tgggaaaaag aagaaatgac aaattaa                    947
```

<210> SEQ ID NO 6
<211> LENGTH: 858
<212> TYPE: DNA
<213> ORGANISM: Artificial Sequence
<220> FEATURE:
<223> OTHER INFORMATION: synthetic gene

<400> SEQUENCE: 6

```
tgtgggaacc aaggtgaaaa aaataacaaa gctgaaacta atcttataa aatggacgat        60 ggcaaaacgg tagatattcc gaaagaccct aaacgcattg cagtagttgc gccaacatat       120
gctggtggac ttaaaaaatt aggtgcaaac attgtagctg taaatcaaca agtcgatcaa       180
agcaaagtat taaagataa atttaaaggt gttacaaaaa ttggtgatgg cgatgtagaa       240
aaagttgcta agaaaagcc agatttaatt attgtatact ctactgacaa agatattaaa       300
aaatatcaaa aagtagcacc aacagtagtt gttgactata taagcataa atatttagaa       360
```

| | |
|---|---|
| caacaagaaa tgttagggaa aattgttggt aaagaagata aagtaaaagc ttggaagaaa | 420 |
| gattgggaag aaacaactgc taaagacggt aaagaaatta aaaagcaat tggacaagat | 480 |
| gcaacagtgt cattgtttga tgaatttgat aaaaaattat acacttacgg cgataactgg | 540 |
| ggtcgtggtg gagaagtatt atatcaagca tttggttga aatgcaacc agaacaacaa | 600 |
| aagttaactg caaaagcagg ttgggctgaa gtgaacaag aagaattga aaatatgct | 660 |
| ggtgattaca ttgtgagtac aagtgaaggt aaacctacac caggatacga atcaacaaac | 720 |
| atgtggaaga atttgaaagc tactaaagaa ggacatattg ttaaagttga tgctggtaca | 780 |
| tactggtaca acgatcctta tacattagat ttcatgcgta aagatttaaa agaaaaatta | 840 |
| attaaagctg caaaataa | 858 |

<210> SEQ ID NO 7
<211> LENGTH: 921
<212> TYPE: DNA
<213> ORGANISM: Artificial Sequence
<220> FEATURE:
<223> OTHER INFORMATION: recombinant plasmidic DNA

<400> SEQUENCE: 7

| | |
|---|---|
| atgatgaaag ctactaaact ggtactgggc gcggtaatcc tgggttctac tctgctggca | 60 |
| ggttgcggga accaaggtga aaaaaataac aaagctgaaa ctaaatctta taaaatggac | 120 |
| gatggcaaaa cggtagatat tccgaaagac cctaaacgca ttgcagtagt tgcgccaaca | 180 |
| tatgctggtg gacttaaaaa attaggtgca aacattgtag ctgtaaatca acaagtcgat | 240 |
| caaagcaaag tattaaaaga taaatttaaa ggtgttacaa aaattggtga tggcgatgta | 300 |
| gaaaagttg ctaagaaaa gccagattta attattgtat actctactga caaagatatt | 360 |
| aaaaatatc aaaagtagc accaacagta gttgttgact ataataagca taatatttta | 420 |
| gaacaacaag aaatgttagg gaaaattgtt ggtaaagaag ataagtaaa gcttggaag | 480 |
| aaagattggg aagaaacaac tgctaaagac ggtaaagaaa ttaaaaaagc aattggacaa | 540 |
| gatgcaacag tgtcattgtt tgatgaattt gataaaaaat tatacactta cggcgataac | 600 |
| tggggtcgtg gtggagaagt attatatcaa gcatttggtt tgaaaatgca accagaacaa | 660 |
| caaaagttaa ctgcaaaagc aggttgggct gaagtgaaac aagaagaaat tgaaaatat | 720 |
| gctggtgatt acattgtgag tacaagtgaa ggtaaaccta caccaggata cgaatcaaca | 780 |
| aacatgtgga agaatttgaa agctactaaa gaaggacata ttgttaaagt tgatgctggt | 840 |
| acatactggt acaacgatcc ttatacatta gatttcatgc gtaaagattt aaaagaaaaa | 900 |
| ttaattaaag ctgcaaaata a | 921 |

<210> SEQ ID NO 8
<211> LENGTH: 921
<212> TYPE: DNA
<213> ORGANISM: Artificial Sequence
<220> FEATURE:
<223> OTHER INFORMATION: recombinant plasmidic DNA

<400> SEQUENCE: 8

| | |
|---|---|
| atgatgaaag ctactaaact ggtactgggc gcggtaatcc tgggttctac tctgctggca | 60 |
| ggtgccggga accaaggtga aaaaaataac aaagctgaaa ctaaatctta taaaatggac | 120 |
| gatggcaaaa cggtagatat tccgaaagac cctaaacgca ttgcagtagt tgcgccaaca | 180 |
| tatgctggtg gacttaaaaa attaggtgca aacattgtag ctgtaaatca acaagtcgat | 240 |
| caaagcaaag tattaaaaga taaatttaaa ggtgttacaa aaattggtga tggcgatgta | 300 |

```
gaaaaagttg ctaaagaaaa gccagattta attattgtat actctactga caaagatatt    360
aaaaaatatc aaaagtagc accaacagta gttgttgact ataataagca taaatatttta    420
```

```
gaaaaagttg ctaaagaaaa gccagattta attattgtat actctactga caaagatatt    360
aaaaaatatc aaaagtagc  accaacagta gttgttgact ataataagca taaatatttta   420 gaacaacaag aaatgttagg gaaaattgtt ggtaaagaag ataaagtaaa agcttggaag    480
aaagattggg aagaaacaac tgctaaagac ggtaaagaaa ttaaaaaagc aattggacaa    540
gatgcaacag tgtcattgtt tgatgaattt gataaaaaat tatacactta cggcgataac    600
tggggtcgtg gtggagaagt attatatcaa gcatttggtt tgaaaatgca accagaacaa    660
caaaagttaa ctgcaaaagc aggttgggct gaagtgaaac aagaagaaat tgaaaaatat    720
gctggtgatt acattgtgag tacaagtgaa ggtaaaccta caccaggata cgaatcaaca    780
aacatgtgga agaatttgaa agctactaaa gaaggacata ttgttaaagt tgatgctggt    840
acatactggt acaacgatcc ttatacatta gatttcatgc gtaaagattt aaaagaaaaa    900
ttaattaaag ctgcaaaata a                                              921

<210> SEQ ID NO 9
<211> LENGTH: 771
<212> TYPE: DNA
<213> ORGANISM: Artificial Sequence
<220> FEATURE:
<223> OTHER INFORMATION: synthetic gene

<400> SEQUENCE: 9
atgatgaaac gattaaacaa attagtgtta ggcattattt ttctgttttt agtcattagt    60
atcactgctg ttgtggcat  aggtaaagaa gcggaagtta agaaaagctt gaaaaaaca    120 ttgagtatgt accctattaa aaatctagag gatttatacg ataaggaagg ctatcgtgat    180
gatcagtttg ataaaaatga taaggtaca tggattataa attctgaaat ggttattcaa    240
cctaataatg aagatatggt agctaaaggc atggttctat atgaatagaa aataccaaa    300 acaacaaatg gttactacta tgtcgatgtg actaaggacg aggatgaagg aaaaccgcac    360
gacaatgaaa aaagatatcc ggttaaaatg gtcgataata aaatcattcc aacaaaagaa    420
attaaagatg aaaaaataaa aaaagaaatc gaaaactttta agttctttgt tcaatatggc    480
gactttaaaa atttgaaaaa ttataaagac ggagatattt catataatcc agaggtgccg    540
agttattcgg ctaaatatca attaactaat gatgattata atgtaaaaca attacgcaaa    600
agatatgata taccgacgag taaagctcca agtgttattgt taaaaggttc agggaattta    660
aaaggctcat cagttggata taaagatatt gaatttacgt tgtagagaa aaagaagaa    720 aatatatact ttagtgatag cttagattat aaaaaaagcg agatgtata a              771

<210> SEQ ID NO 10
<211> LENGTH: 759
<212> TYPE: DNA
<213> ORGANISM: Artificial Sequence
<220> FEATURE:
<223> OTHER INFORMATION: recombinant DNA

<400> SEQUENCE: 10
atgaaagcta ctaaactggt actgggcgcg gtaatcctgg ttctactct gctggcaggt     60 tgcggcatag gtaagaagc  ggaagttaag aaaagctttg aaaaaacatt gagtatgtac    120
cctattaaaa atctagagga tttatacgat aaggaaggct atcgtgatga tcagtttgat    180
aaaaatgata aggtacatg  gattataaat tctgaaatgg ttattcaacc taataatgaa    240
gatatggtag ctaaaggcat ggttctatat atgaatagaa ataccaaaac aacaaatggt    300
```

| | | | |
|---|---|---|---|
| tactactatg tcgatgtgac taaggacgag gatgaaggaa aaccgcacga caatgaaaaa | 360 | | |
| agatatccgg ttaaaatggt cgataataaa atcattccaa caaaagaaat taaagatgaa | 420 | | |
| aaaataaaaa aagaaatcga aaactttaag ttctttgttc aatatggcga ctttaaaaat | 480 | | |
| ttgaaaaatt ataagacgg agatatttca tataatccag aggtgccgag ttattcggct | 540 | | |
| aaatatcaat taactaatga tgattataat gtaaaacaat tacgcaaaag atatgatata | 600 | | |
| ccgacgagta aagctccaaa gttattgtta aaaggttcag ggaatttaaa aggctcatca | 660 | | |
| gttggatata aagatattga atttacgttt gtagagaaaa aagaagaaaa tatatacttt | 720 | | |
| agtgatagct tagattataa aaaaagcgga gatgtataa | 759 | | |

<210> SEQ ID NO 11
<211> LENGTH: 759
<212> TYPE: DNA
<213> ORGANISM: Artificial Sequence
<220> FEATURE:
<223> OTHER INFORMATION: recombinant DNA

<400> SEQUENCE: 11

| | | | |
|---|---|---|---|
| atgaaagcta ctaaactggt actgggcgcg gtaatcctgg gttctactct gctggcaggt | 60 | | |
| gccggcatag gtaagaagc ggaagttaag aaaagctttg aaaaaacatt gagtatgtac | 120 | | |
| cctattaaaa atctagagga tttatacgat aaggaaggct atcgtgatga tcagtttgat | 180 | | |
| aaaaatgata aaggtacatg gattataaat tctgaaatgg ttattcaacc taataatgaa | 240 | | |
| gatatggtag ctaaaggcat ggttctatat atgaatagaa ataccaaaac aacaaatggt | 300 | | |
| tactactatg tcgatgtgac taaggacgag gatgaaggaa aaccgcacga caatgaaaaa | 360 | | |
| agatatccgg ttaaaatggt cgataataaa atcattccaa caaaagaaat taaagatgaa | 420 | | |
| aaaataaaaa aagaaatcga aaactttaag ttctttgttc aatatggcga ctttaaaaat | 480 | | |
| ttgaaaaatt ataagacgg agatatttca tataatccag aggtgccgag ttattcggct | 540 | | |
| aaatatcaat taactaatga tgattataat gtaaaacaat tacgcaaaag atatgatata | 600 | | |
| ccgacgagta aagctccaaa gttattgtta aaaggttcag ggaatttaaa aggctcatca | 660 | | |
| gttggatata aagatattga atttacgttt gtagagaaaa aagaagaaaa tatatacttt | 720 | | |
| agtgatagct tagattataa aaaaagcgga gatgtataa | 759 | | |

<210> SEQ ID NO 12
<211> LENGTH: 873
<212> TYPE: DNA
<213> ORGANISM: Artificial Sequence
<220> FEATURE:
<223> OTHER INFORMATION: recombinant DNA

<400> SEQUENCE: 12

| | | | |
|---|---|---|---|
| gcacagcatg atgaagccaa aaaaaacgcc ttttatcagg ttctgaatat gccgaatctg | 60 | | |
| aatgccgatc agcgtaatgg ttttattcag agcctgaaag cagcaccgag ccagagcgca | 120 | | |
| aatgttctgg gtgaagcaca gaaactgaat gatagccagg caccgaaagc agatgccaaa | 180 | | |
| cgcaacaatt ttaacaaaga taaaaaaagc gcgttttatg aaatcctgaa catgcctaac | 240 | | |
| ctgaatgaag cacagcgcaa tggctttatc cagtctctga agccgcacc gtcacagtct | 300 | | |
| accaatgtgc tgggcgaagc gaaaaaactg aacgaatccc aggctccgaa agccgataat | 360 | | |
| aacttcaaca aagagaaaaa aaacgccttt tatgaaattc tgaatatgcc aaatctgaac | 420 | | |
| gaagaacagc gtaacggttt tattcagtca ctgaaagcgg ctcctagcca gtctgcaaat | 480 | | |
| ctgctgtctg aagccaaaaa actgaatgaa agtcaggcac ctaaagcgga taacaaattt | 540 | | |

```
aacaaagaga aaaaaaacgc attttatgaa atcctgcatc tgccgaatct gaatgaagaa      600
cagcgcaacg gctttattca gagtctgaaa gccgctccgt cccagagcgc caacctgctg      660
gccgaagcaa aaaaactgaa tgatgcgcag gctccgaaag cagataacaa atttaacaaa      720
gagaaaaaaa acgccttcta tgaaattctg cacctgccta acctgaccga agaacagcgt      780 aatggttttta tccagtccct gaaagcggct cctagcgtta gcaaagaaat cctggcagag      840
gccaaaaaac tgaacgacgc acaggcacct aaa                                   873
```

<210> SEQ ID NO 13
<211> LENGTH: 942
<212> TYPE: DNA
<213> ORGANISM: Artificial Sequence
<220> FEATURE:
<223> OTHER INFORMATION: recombinant DNA

<400> SEQUENCE: 13

```
atgatgaaag ctactaaact ggtactgggc gcggtaatcc tgggttctac tctgctggca       60
ggttgcgcac agcatgatga agccaaaaaa aacgcctttt atcaggttct gaatatgccg      120
aatctgaatg ccgatcagcg taatggtttt attcagagcc tgaaagcagc accgagccag      180
agcgcaaatg ttctgggtga agcacagaaa ctgaatgata gccaggcacc gaaagcagat      240
gccaaacgca acaattttaa caagataaa aaaagcgcgt tttatgaaat cctgaacatg      300
cctaacctga atgaagcaca gcgcaatggc tttatccagt ctctgaaagc cgcaccgtca      360
cagtctacca atgtgctggg cgaagcgaaa aaactgaacg aatcccaggc tccgaaagcc      420
gataataact tcaacaaaga gaaaaaaaac gccttttatg aaattctgaa tatgccaaat      480
ctgaacgaag aacagcgtaa cggttttatt cagtcactga aagcggctcc tagccagtct      540
gcaaatctgc tgtctgaagc caaaaaactg aatgaaagtc aggcacctaa agcggataac      600
aaatttaaca agagaaaaa aaacgcattt tatgaaatcc tgcatctgcc gaatctgaat      660
gaagaacagc gcaacggctt tattcagagt ctgaaagccg ctccgtccca gagcgccaac      720
ctgctggccg aagcaaaaaa actgaatgat gcgcaggctc cgaaagcaga taacaaattt      780
aacaaagaga aaaaaacgc cttctatgaa attctgcacc tgcctaacct gaccgaagaa      840
cagcgtaatg gttttatcca gtccctgaaa gcggctccta gcgttagcaa agaaatcctg      900
gcagaggcca aaaaactgaa cgacgcacag gcacctaaat aa                         942
```

<210> SEQ ID NO 14
<211> LENGTH: 942
<212> TYPE: DNA
<213> ORGANISM: Artificial Sequence
<220> FEATURE:
<223> OTHER INFORMATION: recombinant DNA

<400> SEQUENCE: 14

```
atgatgaaag ctactaaact ggtactgggc gcggtaatcc tgggttctac tctgctggca       60
ggtgccgcac agcatgatga agccaaaaaa aacgcctttt atcaggttct gaatatgccg      120
aatctgaatg ccgatcagcg taatggtttt attcagagcc tgaaagcagc accgagccag      180
agcgcaaatg ttctgggtga agcacagaaa ctgaatgata gccaggcacc gaaagcagat      240
gccaaacgca acaattttaa caagataaa aaaagcgcgt tttatgaaat cctgaacatg      300
cctaacctga atgaagcaca gcgcaatggc tttatccagt ctctgaaagc cgcaccgtca      360
cagtctacca atgtgctggg cgaagcgaaa aaactgaacg aatcccaggc tccgaaagcc      420
```

| | |
|---|---|
| gataataact tcaacaaaga gaaaaaaaac gccttttatg aaattctgaa tatgccaaat | 480 |
| ctgaacgaag aacagcgtaa cggttttatt cagtcactga aagcggctcc tagccagtct | 540 |
| gcaaatctgc tgtctgaagc caaaaaactg aatgaaagtc aggcacctaa agcggataac | 600 |
| aaatttaaca agagaaaaaa aaacgcattt tatgaaatcc tgcatctgcc gaatctgaat | 660 |
| gaagaacagc gcaacggctt tattcagagt ctgaaagccg ctccgtccca gagcgccaac | 720 |
| ctgctggccg aagcaaaaaa actgaatgat gcgcaggctc cgaaagcaga taacaaattt | 780 |
| aacaaagaga aaaaaacgc cttctatgaa attctgcacc tgcctaacct gaccgaagaa | 840 |
| cagcgtaatg gttttatcca gtccctgaaa gcggctccta gcgttagcaa agaaatcctg | 900 |
| gcagaggcca aaaaactgaa cgacgcacag gcacctaaat aa | 942 |

<210> SEQ ID NO 15
<211> LENGTH: 906
<212> TYPE: DNA
<213> ORGANISM: Artificial Sequence
<220> FEATURE:
<223> OTHER INFORMATION: recombinant DNA

<400> SEQUENCE: 15

| | |
|---|---|
| ttgtcagtag gactgattgc acctttagca tctccgattc aagaatctag agcaaatact | 60 |
| aatattgaaa atattggtga tggtgctgaa gtaatcaaac gtacggagga tgtaagtagt | 120 |
| aagaaatggg gcgttactca aatgtccaa ttcgactttg taaagataa aaatataac | 180 |
| aaagacgctt taattgttaa atgcaaggt tttattaatt ccagaacttc attttcagat | 240 |
| gtgaagggta gtggatatga attaactaaa cgaatgattt ggccattcca atataatata | 300 |
| ggactgacga ctaaagatcc aaatgttagc ttaatcaatt accttcctaa aaacaaaata | 360 |
| gaaactactg atgttggtca acattagga tataacattg gaggtaattt ccagtcagca | 420 |
| ccatctatag gtggcaatgg ctcatttaat tattctaaaa caattagtta tacccaaaag | 480 |
| agttatgtca gtgaagtaga caagcaaaac tcaaaatctg ttaaatgggg tgttaaagca | 540 |
| aacgaatttg ttacgcctga tggaaaaaaa tctgcgcatg atagatattt attcgtacaa | 600 |
| agtccaaatg gtccaacagg ttcagcaaga gaatattttg ctcctgataa tcaattgcca | 660 |
| cctttagttc aaagtggctt taatccatcg tttatcacta cactatcaca tgaaaaaggt | 720 |
| tcaagtgata cgagtgaatt tgaaatttca tatggtagaa acttagatat tacatatgcg | 780 |
| actttattcc ctagaactgg tatttacgca gaaagaaagc ataatgcatt tgtaaataga | 840 |
| aactttgtag ttagatatga agttaattgg aaaacacacg aaattaaagt gaaaggacat | 900 |
| aattaa | 906 |

<210> SEQ ID NO 16
<211> LENGTH: 918
<212> TYPE: DNA
<213> ORGANISM: Artificial Sequence
<220> FEATURE:
<223> OTHER INFORMATION: recombinant DNA

<400> SEQUENCE: 16

| | |
|---|---|
| atgaaagcta ctaaactggt actgggcgcg gtaatcctgg ttctactctc gctggcaggt | 60 |
| tgcaatacta atattgaaaa tattggtgat ggtgctgaag taatcaaacg tacggaggat | 120 |
| gtaagtagta agaaatgggg cgttactcaa atgtccaat tcgactttgt aaagataaa | 180 |
| aaatataaca aagacgcttt aattgttaaa atgcaaggtt ttattaattc agaacttca | 240 |
| ttttcagatg tgaagggtag tggatatgaa ttaactaaac gaatgatttg gccattccaa | 300 |

| | |
|---|---|
| tataatatag gactgacgac taaagatcca aatgttagct taatcaatta ccttcctaaa | 360 |
| aacaaaatag aaactactga tgttggtcaa acattaggat ataacattgg aggtaatttc | 420 |
| cagtcagcac catctatagg tggcaatggc tcatttaatt attctaaaac aattagttat | 480 |
| acccaaaaga gttatgtcag tgaagtagac aagcaaaact caaaatctgt taaatggggt | 540 |
| gttaaagcaa acgaatttgt tacgcctgat ggaaaaaaat ctgcgcatga tagatattta | 600 |
| ttcgtacaaa gtccaaatgg tccaacaggt tcagcaagag aatattttgc tcctgataat | 660 |
| caattgccac ctttagttca aagtggcttt aatccatcgt ttatcactac actatcacat | 720 |
| gaaaaaggtt caagtgatac gagtgaattt gaaatttcat atggtagaaa cttagatatt | 780 |
| acatatgcga ctttattccc tagaactggt atttacgcag aaagaaagca taatgcattt | 840 |
| gtaaatagaa actttgtagt tagatatgaa gttaattgga aaacacacga aattaaagtg | 900 |
| aaaggacata attaataa | 918 |

<210> SEQ ID NO 17
<211> LENGTH: 918
<212> TYPE: DNA
<213> ORGANISM: Artificial Sequence
<220> FEATURE:
<223> OTHER INFORMATION: recombinant DNA

<400> SEQUENCE: 17

| | |
|---|---|
| atgaaagcta ctaaactggt actgggcgcg gtaatcctgg ttctactct gctggcaggt | 60 |
| gccaatacta atattgaaaa tattggtgat ggtgctgaag taatcaaacg tacggaggat | 120 |
| gtaagtagta agaaatgggg cgttactcaa aatgtccaat tcgactttgt aaaagataaa | 180 |
| aaatataaca aagacgcttt aattgttaaa atgcaaggtt ttattaattc cagaacttca | 240 |
| ttttcagatg tgaagggtag tggatatgaa ttaactaaac gaatgatttg gccattccaa | 300 |
| tataatatag gactgacgac taaagatcca aatgttagct taatcaatta ccttcctaaa | 360 |
| aacaaaatag aaactactga tgttggtcaa acattaggat ataacattgg aggtaatttc | 420 |
| cagtcagcac catctatagg tggcaatggc tcatttaatt attctaaaac aattagttat | 480 |
| acccaaaaga gttatgtcag tgaagtagac aagcaaaact caaaatctgt taaatggggt | 540 |
| gttaaagcaa acgaatttgt tacgcctgat ggaaaaaaat ctgcgcatga tagatattta | 600 |
| ttcgtacaaa gtccaaatgg tccaacaggt tcagcaagag aatattttgc tcctgataat | 660 |
| caattgccac ctttagttca aagtggcttt aatccatcgt ttatcactac actatcacat | 720 |
| gaaaaaggtt caagtgatac gagtgaattt gaaatttcat atggtagaaa cttagatatt | 780 |
| acatatgcga ctttattccc tagaactggt atttacgcag aaagaaagca taatgcattt | 840 |
| gtaaatagaa actttgtagt tagatatgaa gttaattgga aaacacacga aattaaagtg | 900 |
| aaaggacata attaataa | 918 |

<210> SEQ ID NO 18
<211> LENGTH: 3128
<212> TYPE: DNA
<213> ORGANISM: Artificial Sequence
<220> FEATURE:
<223> OTHER INFORMATION: recombinant DNA

<400> SEQUENCE: 18

| | |
|---|---|
| catcgattta ttatgacaac ttgacggcta catcattcac tttttcttca caaccggcac | 60 |
| ggaactcgct cgggctggcc ccggtgcatt ttttaaatac ccgcgagaaa tagagttgat | 120 |

-continued

```
cgtcaaaacc aacattgcga ccgacggtgg cgataggcat ccgggtggtg ctcaaaagca    180
gcttcgcctg gctgatacgt tggtcctcgc gccagcttaa gacgctaatc cctaactgct    240
ggcggaaaag atgtgacaga cgcgacggcg acaagcaaac atgctgtgcg acgctggcga    300
tatcaaaatt gctgtctgcc aggtgatcgc tgatgtactg acaagcctcg cgtacccgat    360
tatccatcgg tggatggagc gactcgttaa tcgcttccat gcgccgcagt aacaattgct    420
caagcagatt tatcgccagc agctccgaat agcgcccttc cccttgcccg gcgttaatga    480
tttgcccaaa caggtcgctg aaatgcggct ggtgcgcttc atccgggcga agaaccccg    540 tattggcaaa tattgacggc cagttaagcc attcatgcca gtaggcgcgc ggacgaaagt    600
aaacccactg gtgataccat tcgcgagcct ccggatgacg accgtagtga tgaatctctc    660
ctggcgggaa cagcaaaata tcacccggtc ggcaaacaaa ttctcgtccc tgattttca    720 ccaccccctg accgcgaatg gtgagattga aatataacc tttcattccc agcggtcggt    780
cgataaaaaa atcgagataa ccgttggcct caatcgcgt taaacccgcc accagatggg    840
cattaaacga gtatcccggc agcaggggat catttttgcgc ttcagccata cttttcatac    900
tcccgccatt cagagaagaa accaattgtc catattgcat cagacattgc cgtcactgcg    960
tcttttactg gctcttctcg ctaaccaaac cggtaacccc gcttattaaa agcattctgt   1020
aacaaagcgg gaccaaagcc atgacaaaaa cgcgtaacaa aagtgtctat aatcacggca   1080
gaaaagtcca cattgattat ttgcacggcg tcacactttg ctatgccata gcatttttat   1140
ccataagatt agcggatcct acctgacgct ttttatcgca actctctact gtttctccat   1200
acccgttttt ttgggaattc gagctctaag gaggttataa aaaatggata ttaatactga   1260
aactgagatc aagcaaaagc attcactaac ccccttcct gttttcctaa tcagcccggc   1320
atttcgcggg cgatattttc acagctattt caggagttca gccatgaacg cttattacat   1380
tcaggatcgt cttgaggctc agagctgggc gcgtcactac cagcagctcg cccgtgaaga   1440
gaaagaggca gaactggcag acgacatgga aaaaggcctg ccccagcacc tgtttgaatc   1500
gctatgcatc gatcatttgc aacgccacgg ggccagcaaa aaatccatta cccgtgcgtt   1560
tgatgacgat gttgagtttc aggagcgcat ggcagaacac atccggtaca tggttgaaac   1620
cattgctcac caccaggttg atattgattc agaggtataa aacgaatgag tactgcactc   1680
gcaacgctgg ctgggaagct ggctgaacgt gtcggcatgg attctgtcga cccacaggaa   1740
ctgatcacca ctcttcgcca gacggcattt aaaggtgatg ccagcgatgc gcagttcatc   1800
gcattactga tcgttgccaa ccagtacggc cttaatccgt ggacgaaaga aatttacgcc   1860
tttcctgata agcagaatgg catcgttccg gtggtgggcg ttgatggctg gtcccgcatc   1920
atcaatgaaa accagcagtt tgatggcatg gactttgagc aggacaatga atcctgtaca   1980
tgccggattt accgcaagga ccgtaatcat ccgatctgcg ttaccgaatg gatggatgaa   2040
tgccgccgcg aaccattcaa aactcgcgaa ggcagagaaa tcacggggcc gtggcagtcg   2100
catcccaaac ggatgttacg tcataaagcc atgattcagt gtgcccgtct ggccttcgga   2160
tttgctggta tctatgacaa ggatgaagcc gagcgcattg tcgaaaatac tgcatacact   2220
gcagaacgtc agccggaacg cgacatcact ccggttaacg atgaaaccat gcaggagatt   2280
aacactctgc tgatcgccct ggataaaaca tgggatgacg acttattgcc gctctgttcc   2340
cagatatttc gccgcgacat tcgtgcatcg tcagaactga cacaggccga agcagtaaaa   2400
gctcttggat tcctgaaaca gaaagccgca gagcagaagg tggcagcatg acaccggaca   2460
ttatcctgca gcgtaccggg atcgatgtga gagctgtcga acagggggat gatgcgtggc   2520
```

-continued

```
acaaattacg gctcggcgtc atcaccgctt cagaagttca caacgtgata gcaaaacccc      2580
gctccggaaa gaagtggcct gacatgaaaa tgtcctactt ccacaccctg cttgctgagg      2640
tttgcaccgg tgtggctccg gaagttaacg ctaaagcact ggcctgggga aaacagtacg      2700
agaacgacgc cagaaccctg tttgaattca cttccggcgt gaatgttact gaatcccga      2760 tcatctatcg cgacgaaagt atgcgtaccg cctgctctcc cgatggttta tgcagtgacg      2820
gcaacggcct tgaactgaaa tgcccgttta cctcccggga tttcatgaag ttccggctcg      2880
gtggtttcga ggccataaag tcagcttaca tggcccaggt gcagtacagc atgtgggtga      2940
cgcgaaaaaa tgcctggtac tttgccaact atgacccgcg tatgaagcgt gaaggcctgc      3000
attatgtcgt gattgagcgg gatgaaaagt acatggcgag ttttgacgag atcgtgccgg      3060
agttcatcga aaaaatggac gaggcactgg ctgaaattgg ttttgtattt ggggagcaat      3120
ggcgatga                                                               3128
```

<210> SEQ ID NO 19
<211> LENGTH: 2882
<212> TYPE: DNA
<213> ORGANISM: Artificial Sequence
<220> FEATURE:
<223> OTHER INFORMATION: recombinant DNA

<400> SEQUENCE: 19

```
gggcaccaat aactgcctta aaaaaaatga ttgaacaaga tggattgcac gcaggttctc        60
cggccgcttg ggtggagagg ctattcggct atgactgggc acaacagaca atcggctgct       120
ctgatgccgc cgtgttccgg ctgtcagcgc agggggcgccc ggttcttttt gtcaagaccg      180
acctgtccgg tgccctgaat gaactgcagg acgaggcagc gcggctatcg tggctggcca      240
cgacgggcgt tccttgcgca gctgtgctcg acgttgtcac tgaagcggga agggactggc      300
tgctattggg cgaagtgccg gggcaggatc tcctgtcatc tcaccttgct cctgccgaga      360
aagtatccat catggctgat gcaatgcggc ggctgcatac gcttgatccg gctacctgcc      420
cattcgacca ccaagcgaaa catcgcatcg agcgagcacg tactcggatg aagccggtc       480 ttgtcgatca ggatgatctg gacgaagagc atcagggggct cgcgccagcc gaactgttcg      540
ccaggctcaa ggcgcgcatg cccgacggcg aggatctcgt cgtgacccat ggcgatgcct      600
gcttgccgaa tatcatggtg aaaatggcc gcttttctgg attcatcgac tgtggccggc       660
tgggtgtggc ggaccgctat caggacatag cgttggctac ccgtgatatt gctgaagagc      720
ttggcggcga atgggctgac cgcttcctcg tgctttacgg tatcgccgct cccgattcgc      780
agcgcatcgc cttctatcgc cttcttgacg agttcttctg atttagcttc cttagctcct      840
gaaaatctcg ataactcaaa aaatacgccc ggtagtgatc ttatttcatt atggtgaaag      900
ttggaacctc ttacgtgccg atcaacgtct cacgggatcc ttaattaagt ctagagtcga      960
ctgtttaaac ctgcagatcc ttttaaccc atcacatata cctgccgttc actattattt      1020
agtgaaatga gatattatga tattttctga attgtgatta aaaaggcaac tttatgccca      1080
tgcaacagaa actataaaaa atacagaaa tgaaagaaa cagatagatt ttttagttct       1140
ttaggcccgt agtctgcaaa tccttttatg attttctatc aaacaaaaga ggaaaataga      1200
ccagttgcaa tccaaacgag agtctaatag aatgaggtcg aaaagtaaat cgcgcgggtt      1260
tgttactgat aaagcaggca agacctaaaa tgtgtaaagg gcaaagtgta actttggcg       1320 tcaccccta catatttag gtctttttttt attgtgcgta actaacttgc catcttcaaa       1380
```

```
caggagggct ggaagaagca gaccgctaac acagtacata aaaaggaga catgaacgat    1440 gaacatcaaa aagtttgcaa acaagcaac agtattaacc tttactaccg cactgctggc    1500
aggaggcgca actcaagcgt tgcgaaaga acgaaccaa aagccatata aggaaacata    1560
cggcatttcc catattacac gccatgatat gctgcaaatc cctgaacagc aaaaaaatga    1620
aaaatatcaa gttcctgaat tcgattcgtc cacaattaaa aatatctctt ctgcaaaagg    1680
cctggacgtt tgggacagct ggccattaca aaacgctgac ggcactgtcg caaactatca    1740
cggctaccac atcgtctttg cattagccgg agatcctaaa aatgcggatg acacatcgat    1800
ttacatgttc tatcaaaaag tcggcgaaac ttctattgac agctggaaaa acgctggccg    1860 cgtcttttaaa gacagcgaca aattcgatgc aaatgattct atcctaaaag accaaacaca    1920
agaatggtca ggttcagcca catttacatc tgacggaaaa atccgtttat tctacactga    1980
tttctccggt aaacattacg gcaaacaaac actgacaact gcacaagtta acgtatcagc    2040
atcagacagc tctttgaaca tcaacggtgt agaggattat aaatcaatct ttgacggtga    2100
cggaaaaacg tatcaaaatg tacagcagtt catcgatgaa ggcaactaca gctcaggcga    2160
caaccatacg ctgagagatc ctcactacgt agaagataaa ggccacaaat acttagtatt    2220
tgaagcaaac actggaactg aagatggcta ccaaggcgaa gaatctttat ttaacaaagc    2280
atactatggc aaaagcacat cattcttccg tcaagaaagt caaaaacttc tgcaaagcga    2340
taaaaaacgc acggctgagt tagcaaacgg cgctctcggt atgattgagc taacgatga    2400 ttacacactg aaaaaagtga tgaaaccgct gattgcatct aacacagtaa cagatgaaat    2460
tgaacgcgcg aacgtcttta aaatgaacgg caaatggtac ctgttcactg actcccgcgg    2520
atcaaaaatg acgattgacg gcattacgtc taacgatatt tacatgcttg gttatgtttc    2580
taattcttta actggcccat acaagccgct gaacaaaact ggccttgtgt aaaaatgga    2640 tcttgatcct aacgatgtaa cctttactta ctcacacttc gctgtacctc aagcgaaagg    2700
aaacaatgtc gtgattacaa gctatatgac aaacagagga ttctacgcag acaaacaatc    2760
aacgtttgcg ccaagcttcc tgctgaacat caaaggcaag aaaacatctg ttgtcaaaga    2820
cagcatcctt gaacaaggac aattaacagt taacaaataa aaacgcaaaa gaaaatgccg    2880
at                                                                   2882
```

<210> SEQ ID NO 20
<211> LENGTH: 559
<212> TYPE: PRT
<213> ORGANISM: Artificial Sequence
<220> FEATURE:
<223> OTHER INFORMATION: recombinant protein

<400> SEQUENCE: 20

```
Met Lys Ala Thr Lys Leu Val Leu Gly Ala Val Ile Leu Gly Ser Thr
1               5                   10                  15

Leu Leu Ala Gly Cys Asn Lys Gln Asn Thr Ala Ser Thr Glu Thr Thr
            20                  25                  30

Thr Thr Asn Glu Gln Pro Lys Pro Glu Ser Ser Glu Leu Thr Thr Glu
        35                  40                  45

Lys Ala Gly Gln Lys Thr Asp Asp Met Leu Asn Ser Asn Asp Met Ile
    50                  55                  60

Lys Leu Ala Pro Lys Glu Met Pro Leu Glu Ser Ala Glu Lys Glu Glu
65                  70                  75                  80

Lys Lys Ser Glu Asp Lys Lys Ser Glu Glu Asp His Thr Glu Glu
            85                  90                  95
```

-continued

```
Ile Asn Asp Lys Ile Tyr Ser Leu Asn Tyr Asn Glu Leu Glu Val Leu
            100                 105                 110
Ala Lys Asn Gly Glu Thr Ile Glu Asn Phe Val Pro Lys Glu Gly Val
            115                 120                 125
Lys Lys Ala Asp Lys Phe Ile Val Ile Glu Arg Lys Lys Lys Asn Ile
130                 135                 140
Asn Thr Thr Pro Val Asp Ile Ser Ile Asp Ser Val Thr Asp Arg
145                 150                 155                 160
Thr Tyr Pro Ala Ala Leu Gln Leu Ala Asn Lys Gly Phe Thr Glu Asn
                    165                 170                 175
Lys Pro Asp Ala Val Val Thr Lys Arg Asn Pro Gln Lys Ile His Ile
            180                 185                 190
Asp Leu Pro Gly Met Gly Asp Lys Ala Thr Val Glu Val Asn Asp Pro
            195                 200                 205
Thr Tyr Ala Asn Val Ser Thr Ala Ile Asp Asn Leu Val Asn Gln Trp
            210                 215                 220
His Asp Asn Tyr Ser Gly Gly Asn Thr Leu Pro Ala Arg Thr Gln Tyr
225                 230                 235                 240
Thr Glu Ser Met Val Tyr Ser Lys Ser Gln Ile Glu Ala Ala Leu Asn
                    245                 250                 255
Val Asn Ser Lys Ile Leu Asp Gly Thr Leu Gly Ile Asp Phe Lys Ser
            260                 265                 270
Ile Ser Lys Gly Glu Lys Lys Val Met Ile Ala Ala Tyr Lys Gln Ile
            275                 280                 285
Phe Tyr Thr Val Ser Ala Asn Leu Pro Asn Asn Pro Ala Asp Val Phe
            290                 295                 300
Asp Lys Ser Val Thr Phe Lys Glu Leu Gln Arg Lys Gly Val Ser Asn
305                 310                 315                 320
Glu Ala Pro Pro Leu Phe Val Ser Asn Val Ala Tyr Gly Arg Thr Val
                    325                 330                 335
Phe Val Lys Leu Glu Thr Ser Ser Lys Ser Asn Asp Val Glu Ala Ala
            340                 345                 350
Phe Ser Ala Ala Leu Lys Gly Thr Asp Val Lys Thr Asn Gly Lys Tyr
            355                 360                 365
Ser Asp Ile Leu Glu Asn Ser Ser Phe Thr Ala Val Val Leu Gly Gly
            370                 375                 380
Asp Ala Ala Glu His Asn Lys Val Val Thr Lys Asp Phe Asp Val Ile
385                 390                 395                 400
Arg Asn Val Ile Lys Asp Asn Ala Thr Phe Ser Arg Lys Asn Leu Ala
                    405                 410                 415
Tyr Pro Ile Ser Tyr Thr Ser Val Phe Leu Lys Asn Asn Lys Ile Ala
            420                 425                 430
Gly Val Asn Asn Arg Thr Glu Tyr Val Glu Thr Thr Ser Thr Glu Tyr
            435                 440                 445
Thr Ser Gly Lys Ile Asn Leu Ser His Gln Gly Ala Tyr Val Ala Gln
            450                 455                 460
Tyr Glu Ile Leu Trp Asp Glu Ile Asn Tyr Asp Asp Lys Gly Lys Glu
465                 470                 475                 480
Val Ile Thr Lys Arg Arg Trp Asp Asn Asn Trp Tyr Ser Lys Thr Ser
                    485                 490                 495
Pro Phe Ser Thr Val Ile Pro Leu Gly Ala Asn Ser Arg Asn Ile Arg
            500                 505                 510
```

```
Ile Met Ala Arg Glu Cys Thr Gly Leu Ala Phe Glu Trp Trp Arg Lys
            515                 520                 525

Val Ile Asp Glu Arg Asp Val Lys Leu Ser Lys Glu Ile Asn Val Asn
        530                 535                 540

Ile Ser Gly Ser Thr Leu Ser Pro Tyr Gly Ser Ile Thr Tyr Lys
545                 550                 555

<210> SEQ ID NO 21
<211> LENGTH: 559
<212> TYPE: PRT
<213> ORGANISM: Artificial Sequence
<220> FEATURE:
<223> OTHER INFORMATION: recombinant protein

<400> SEQUENCE: 21

Met Lys Ala Thr Lys Leu Val Leu Gly Ala Val Ile Leu Gly Ser Thr
1               5                   10                  15

Leu Leu Ala Gly Ala Asn Lys Gln Asn Thr Ala Ser Thr Glu Thr Thr
            20                  25                  30

Thr Thr Asn Glu Gln Pro Lys Pro Glu Ser Ser Glu Leu Thr Thr Glu
        35                  40                  45

Lys Ala Gly Gln Lys Thr Asp Asp Met Leu Asn Ser Asn Asp Met Ile
50                  55                  60

Lys Leu Ala Pro Lys Glu Met Pro Leu Glu Ser Ala Glu Lys Glu Glu
65                  70                  75                  80

Lys Lys Ser Glu Asp Lys Lys Ser Glu Glu Asp His Thr Glu Glu
            85                  90                  95

Ile Asn Asp Lys Ile Tyr Ser Leu Asn Tyr Asn Glu Leu Glu Val Leu
            100                 105                 110

Ala Lys Asn Gly Glu Thr Ile Glu Asn Phe Val Pro Lys Glu Gly Val
            115                 120                 125

Lys Lys Ala Asp Lys Phe Ile Val Ile Glu Arg Lys Lys Lys Asn Ile
130                 135                 140

Asn Thr Thr Pro Val Asp Ile Ser Ile Ile Asp Ser Val Thr Asp Arg
145                 150                 155                 160

Thr Tyr Pro Ala Ala Leu Gln Leu Ala Asn Lys Gly Phe Thr Glu Asn
                165                 170                 175

Lys Pro Asp Ala Val Val Thr Lys Arg Asn Pro Gln Lys Ile His Ile
            180                 185                 190

Asp Leu Pro Gly Met Gly Asp Lys Ala Thr Val Glu Val Asn Asp Pro
        195                 200                 205

Thr Tyr Ala Asn Val Ser Thr Ala Ile Asp Asn Leu Val Asn Gln Trp
210                 215                 220

His Asp Asn Tyr Ser Gly Gly Asn Thr Leu Pro Ala Arg Thr Gln Tyr
225                 230                 235                 240

Thr Glu Ser Met Val Tyr Ser Lys Ser Gln Ile Glu Ala Ala Leu Asn
                245                 250                 255

Val Asn Ser Lys Ile Leu Asp Gly Thr Leu Gly Ile Asp Phe Lys Ser
            260                 265                 270

Ile Ser Lys Gly Glu Lys Lys Val Met Ile Ala Ala Tyr Lys Gln Ile
        275                 280                 285

Phe Tyr Thr Val Ser Ala Asn Leu Pro Asn Asn Pro Ala Asp Val Phe
290                 295                 300

Asp Lys Ser Val Thr Phe Lys Glu Leu Gln Arg Lys Gly Val Ser Asn
305                 310                 315                 320
```

Glu Ala Pro Pro Leu Phe Val Ser Asn Val Ala Tyr Gly Arg Thr Val
                325                 330                 335

Phe Val Lys Leu Glu Thr Ser Ser Lys Ser Asn Asp Val Glu Ala Ala
            340                 345                 350

Phe Ser Ala Ala Leu Lys Gly Thr Asp Val Lys Thr Asn Gly Lys Tyr
            355                 360                 365

Ser Asp Ile Leu Glu Asn Ser Ser Phe Thr Ala Val Val Leu Gly Gly
            370                 375                 380

Asp Ala Ala Glu His Asn Lys Val Val Thr Lys Asp Phe Asp Val Ile
385                 390                 395                 400

Arg Asn Val Ile Lys Asp Asn Ala Thr Phe Ser Arg Lys Asn Leu Ala
                405                 410                 415

Tyr Pro Ile Ser Tyr Thr Ser Val Phe Leu Lys Asn Asn Lys Ile Ala
                420                 425                 430

Gly Val Asn Asn Arg Thr Glu Tyr Val Glu Thr Thr Ser Thr Glu Tyr
                435                 440                 445

Thr Ser Gly Lys Ile Asn Leu Ser His Gln Gly Ala Tyr Val Ala Gln
            450                 455                 460

Tyr Glu Ile Leu Trp Asp Glu Ile Asn Tyr Asp Asp Lys Gly Lys Glu
465                 470                 475                 480

Val Ile Thr Lys Arg Arg Trp Asp Asn Asn Trp Tyr Ser Lys Thr Ser
                485                 490                 495

Pro Phe Ser Thr Val Ile Pro Leu Gly Ala Asn Ser Arg Asn Ile Arg
            500                 505                 510

Ile Met Ala Arg Glu Cys Thr Gly Leu Ala Phe Glu Trp Trp Arg Lys
            515                 520                 525

Val Ile Asp Glu Arg Asp Val Lys Leu Ser Lys Glu Ile Asn Val Asn
530                 535                 540

Ile Ser Gly Ser Thr Leu Ser Pro Tyr Gly Ser Ile Thr Tyr Lys
545                 550                 555

<210> SEQ ID NO 22
<211> LENGTH: 293
<212> TYPE: PRT
<213> ORGANISM: Artificial Sequence
<220> FEATURE:
<223> OTHER INFORMATION: recombinant protein

<400> SEQUENCE: 22

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met Leu Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Gly Ala Asn Lys Ser Gly Leu Ala Trp
65              70                  75                  80

Pro Ser Ala Phe Lys Val Gln Leu Gln Leu Pro Asp Asn Glu Val Ala
            85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
            115                 120                 125

```
Thr Gly Lys Ile Gly Gly Leu Ile Gly Ala Asn Val Ser Ile Gly His
130                 135                 140
Thr Leu Lys Tyr Val Gln Pro Asp Phe Lys Thr Ile Leu Glu Ser Pro
145                 150                 155                 160
Thr Asp Lys Lys Val Gly Trp Lys Val Ile Phe Asn Asn Met Val Asn
                165                 170                 175
Gln Asn Trp Gly Pro Tyr Asp Arg Asp Ser Trp Asn Pro Val Tyr Gly
            180                 185                 190
Asn Gln Leu Phe Met Lys Thr Arg Asn Gly Ser Met Lys Ala Ala Asp
        195                 200                 205
Asn Phe Leu Asp Pro Asn Lys Ala Ser Ser Leu Leu Ser Ser Gly Phe
210                 215                 220
Ser Pro Asp Phe Ala Thr Val Ile Thr Met Asp Arg Lys Ala Ser Lys
225                 230                 235                 240
Gln Gln Thr Asn Ile Asp Val Ile Tyr Glu Arg Val Arg Asp Asp Tyr
                245                 250                 255
Gln Leu His Trp Thr Ser Thr Asn Trp Lys Gly Thr Asn Thr Lys Asp
            260                 265                 270
Lys Trp Ile Asp Arg Ser Ser Glu Arg Tyr Lys Ile Asp Trp Glu Lys
        275                 280                 285
Glu Glu Met Thr Asn
        290

<210> SEQ ID NO 23
<211> LENGTH: 314
<212> TYPE: PRT
<213> ORGANISM: Artificial Sequence
<220> FEATURE:
<223> OTHER INFORMATION: recombinant protein

<400> SEQUENCE: 23

Met Lys Ala Thr Lys Leu Val Leu Gly Ala Val Ile Leu Gly Ser Ile
1               5                   10                  15
Leu Leu Ala Gly Cys Ala Asp Ser Asp Ile Asn Ile Lys Thr Gly Thr
            20                  25                  30
Thr Asp Ile Gly Ser Asn Thr Thr Val Lys Thr Gly Asp Leu Val Thr
        35                  40                  45
Tyr Asp Lys Glu Asn Gly Met Leu Lys Lys Val Phe Tyr Ser Phe Ile
    50                  55                  60
Asp Asp Lys Asn His Asn Lys Lys Leu Leu Val Ile Arg Thr Lys Gly
65                  70                  75                  80
Thr Ile Ala Gly Gln Tyr Arg Val Tyr Ser Glu Gly Ala Asn Lys
                85                  90                  95
Ser Gly Leu Ala Trp Pro Ser Ala Phe Lys Val Gln Leu Gln Leu Pro
            100                 105                 110
Asp Asn Glu Val Ala Gln Ile Ser Asp Tyr Tyr Pro Arg Asn Ser Ile
        115                 120                 125
Asp Thr Lys Glu Tyr Met Ser Thr Leu Thr Tyr Gly Phe Asn Gly Asn
    130                 135                 140
Val Thr Gly Asp Asp Thr Gly Lys Ile Gly Gly Leu Ile Gly Ala Asn
145                 150                 155                 160
Val Ser Ile Gly His Thr Leu Lys Tyr Val Gln Pro Asp Phe Lys Thr
                165                 170                 175
Ile Leu Glu Ser Pro Thr Asp Lys Lys Val Gly Trp Lys Val Ile Phe
            180                 185                 190
```

Asn Asn Met Val Asn Gln Asn Trp Gly Pro Tyr Asp Arg Asp Ser Trp
            195                 200                 205

Asn Pro Val Tyr Gly Asn Gln Leu Phe Met Lys Thr Arg Asn Gly Ser
        210                 215                 220

Met Lys Ala Ala Asp Asn Phe Leu Asp Pro Asn Lys Ala Ser Ser Leu
225                 230                 235                 240

Leu Ser Ser Gly Phe Ser Pro Asp Phe Ala Thr Val Ile Thr Met Asp
                245                 250                 255

Arg Lys Ala Ser Lys Gln Gln Thr Asn Ile Asp Val Ile Tyr Glu Arg
            260                 265                 270

Val Arg Asp Asp Tyr Gln Leu His Trp Thr Ser Thr Asn Trp Lys Gly
        275                 280                 285

Thr Asn Thr Lys Asp Lys Trp Ile Asp Arg Ser Ser Glu Arg Tyr Lys
290                 295                 300

Ile Asp Trp Glu Lys Glu Met Thr Asn
305                 310

<210> SEQ ID NO 24
<211> LENGTH: 314
<212> TYPE: PRT
<213> ORGANISM: Artificial Sequence
<220> FEATURE:
<223> OTHER INFORMATION: recombinant protein

<400> SEQUENCE: 24

Met Lys Ala Thr Lys Leu Val Leu Gly Ala Val Ile Leu Gly Ser Thr
1               5                   10                  15

Leu Leu Ala Gly Ala Ala Asp Ser Asp Ile Asn Ile Lys Thr Gly Thr
            20                  25                  30

Thr Asp Ile Gly Ser Asn Thr Thr Val Lys Thr Gly Asp Leu Val Thr
        35                  40                  45

Tyr Asp Lys Glu Asn Gly Met Leu Lys Lys Val Phe Tyr Ser Phe Ile
50                  55                  60

Asp Asp Lys Asn His Asn Lys Lys Leu Leu Val Ile Arg Thr Lys Gly
65                  70                  75                  80

Thr Ile Ala Gly Gln Tyr Arg Val Tyr Ser Glu Glu Gly Ala Asn Lys
                85                  90                  95

Ser Gly Leu Ala Trp Pro Ser Ala Phe Lys Val Gln Leu Gln Leu Pro
            100                 105                 110

Asp Asn Glu Val Ala Gln Ile Ser Asp Tyr Tyr Pro Arg Asn Ser Ile
        115                 120                 125

Asp Thr Lys Glu Tyr Met Ser Thr Leu Thr Tyr Gly Phe Asn Gly Asn
            130                 135                 140

Val Thr Gly Asp Asp Thr Gly Lys Ile Gly Gly Leu Ile Gly Ala Asn
145                 150                 155                 160

Val Ser Ile Gly His Thr Leu Lys Tyr Val Gln Pro Asp Phe Lys Thr
                165                 170                 175

Ile Leu Glu Ser Pro Thr Asp Lys Lys Val Gly Trp Lys Val Ile Phe
            180                 185                 190

Asn Asn Met Val Asn Gln Asn Trp Gly Pro Tyr Asp Arg Asp Ser Trp
            195                 200                 205

Asn Pro Val Tyr Gly Asn Gln Leu Phe Met Lys Thr Arg Asn Gly Ser
        210                 215                 220

Met Lys Ala Ala Asp Asn Phe Leu Asp Pro Asn Lys Ala Ser Ser Leu
225                 230                 235                 240

```
Leu Ser Ser Gly Phe Ser Pro Asp Phe Ala Thr Val Ile Thr Met Asp
                245                 250                 255

Arg Lys Ala Ser Lys Gln Gln Thr Asn Ile Asp Val Ile Tyr Glu Arg
            260                 265                 270

Val Arg Asp Asp Tyr Gln Leu His Trp Thr Ser Thr Asn Trp Lys Gly
        275                 280                 285

Thr Asn Thr Lys Asp Lys Trp Ile Asp Arg Ser Ser Glu Arg Tyr Lys
    290                 295                 300

Ile Asp Trp Glu Lys Glu Met Thr Asn
305                 310
```

<210> SEQ ID NO 25
<211> LENGTH: 285
<212> TYPE: PRT
<213> ORGANISM: Artificial Sequence
<220> FEATURE:
<223> OTHER INFORMATION: recombinant protein

<400> SEQUENCE: 25

```
Cys Gly Asn Gln Gly Glu Lys Asn Asn Lys Ala Glu Thr Lys Ser Tyr
1               5                   10                  15

Lys Met Asp Asp Gly Lys Thr Val Asp Ile Pro Lys Asp Pro Lys Arg
            20                  25                  30

Ile Ala Val Val Ala Pro Thr Tyr Ala Gly Gly Leu Lys Lys Leu Gly
        35                  40                  45

Ala Asn Ile Val Ala Val Asn Gln Gln Val Asp Gln Ser Lys Val Leu
    50                  55                  60

Lys Asp Lys Phe Lys Gly Val Thr Lys Ile Gly Asp Gly Asp Val Glu
65                  70                  75                  80

Lys Val Ala Lys Glu Lys Pro Asp Leu Ile Ile Val Tyr Ser Thr Asp
                85                  90                  95

Lys Asp Ile Lys Lys Tyr Gln Lys Val Ala Pro Thr Val Val Val Asp
            100                 105                 110

Tyr Asn Lys His Lys Tyr Leu Glu Gln Gln Glu Met Leu Gly Lys Ile
        115                 120                 125

Val Gly Lys Glu Asp Lys Val Lys Ala Trp Lys Lys Asp Trp Glu Glu
    130                 135                 140

Thr Thr Ala Lys Asp Gly Lys Glu Ile Lys Lys Ala Ile Gly Gln Asp
145                 150                 155                 160

Ala Thr Val Ser Leu Phe Asp Glu Phe Asp Lys Lys Leu Tyr Thr Tyr
                165                 170                 175

Gly Asp Asn Trp Gly Arg Gly Gly Glu Val Leu Tyr Gln Ala Phe Gly
            180                 185                 190

Leu Lys Met Gln Pro Glu Gln Gln Lys Leu Thr Ala Lys Ala Gly Trp
        195                 200                 205

Ala Glu Val Lys Gln Glu Glu Ile Glu Lys Tyr Ala Gly Asp Tyr Ile
    210                 215                 220

Val Ser Thr Ser Glu Gly Lys Pro Thr Pro Gly Tyr Glu Ser Thr Asn
225                 230                 235                 240

Met Trp Lys Asn Leu Lys Ala Thr Lys Glu Gly His Ile Val Lys Val
                245                 250                 255

Asp Ala Gly Thr Tyr Trp Tyr Asn Asp Pro Tyr Thr Leu Asp Phe Met
            260                 265                 270

Arg Lys Asp Leu Lys Glu Lys Leu Ile Lys Ala Ala Lys
        275                 280                 285
```

<210> SEQ ID NO 26
<211> LENGTH: 305
<212> TYPE: PRT
<213> ORGANISM: Artificial Sequence
<220> FEATURE:
<223> OTHER INFORMATION: recombinant protein

<400> SEQUENCE: 26

Met Lys Ala Thr Lys Leu Val Leu Gly Ala Val Ile Leu Gly Ser Thr
1               5                   10                  15

Leu Leu Ala Gly Cys Gly Asn Gln Gly Glu Lys Asn Asn Lys Ala Glu
            20                  25                  30

Thr Lys Ser Tyr Lys Met Asp Asp Gly Lys Thr Val Asp Ile Pro Lys
        35                  40                  45

Asp Pro Lys Arg Ile Ala Val Ala Pro Thr Tyr Ala Gly Gly Leu
    50                  55                  60

Lys Lys Leu Gly Ala Asn Ile Val Ala Val Asn Gln Gln Val Asp Gln
65                  70                  75                  80

Ser Lys Val Leu Lys Asp Lys Phe Lys Gly Val Thr Lys Ile Gly Asp
                85                  90                  95

Gly Asp Val Glu Lys Val Ala Lys Glu Lys Pro Asp Leu Ile Ile Val
            100                 105                 110

Tyr Ser Thr Asp Lys Asp Ile Lys Lys Tyr Gln Lys Val Ala Pro Thr
        115                 120                 125

Val Val Val Asp Tyr Asn Lys His Lys Tyr Leu Glu Gln Gln Glu Met
130                 135                 140

Leu Gly Lys Ile Val Gly Lys Glu Asp Lys Val Lys Ala Trp Lys Lys
145                 150                 155                 160

Asp Trp Glu Glu Thr Thr Ala Lys Asp Gly Lys Glu Ile Lys Lys Ala
                165                 170                 175

Ile Gly Gln Asp Ala Thr Val Ser Leu Phe Asp Glu Phe Asp Lys Lys
            180                 185                 190

Leu Tyr Thr Tyr Gly Asp Asn Trp Gly Arg Gly Gly Glu Val Leu Tyr
        195                 200                 205

Gln Ala Phe Gly Leu Lys Met Gln Pro Glu Gln Lys Leu Thr Ala
    210                 215                 220

Lys Ala Gly Trp Ala Glu Val Lys Gln Glu Glu Ile Glu Lys Tyr Ala
225                 230                 235                 240

Gly Asp Tyr Ile Val Ser Thr Ser Glu Gly Lys Pro Thr Pro Gly Tyr
                245                 250                 255

Glu Ser Thr Asn Met Trp Lys Asn Leu Lys Ala Thr Lys Glu Gly His
            260                 265                 270

Ile Val Lys Val Asp Ala Gly Thr Tyr Trp Tyr Asn Asp Pro Tyr Thr
        275                 280                 285

Leu Asp Phe Met Arg Lys Asp Leu Lys Glu Lys Leu Ile Lys Ala Ala
    290                 295                 300

Lys
305

<210> SEQ ID NO 27
<211> LENGTH: 305
<212> TYPE: PRT
<213> ORGANISM: Artificial Sequence
<220> FEATURE:
<223> OTHER INFORMATION: recombinant protein

<400> SEQUENCE: 27

Met Lys Ala Thr Lys Leu Val Leu Gly Ala Val Ile Leu Gly Ser Thr
1               5                   10                  15

Leu Leu Ala Gly Ala Gly Asn Gln Gly Glu Lys Asn Asn Lys Ala Glu
            20                  25                  30

Thr Lys Ser Tyr Lys Met Asp Asp Gly Lys Thr Val Asp Ile Pro Lys
        35                  40                  45

Asp Pro Lys Arg Ile Ala Val Val Ala Pro Thr Tyr Ala Gly Gly Leu
    50                  55                  60

Lys Lys Leu Gly Ala Asn Ile Val Ala Val Asn Gln Gln Val Asp Gln
65                  70                  75                  80

Ser Lys Val Leu Lys Asp Lys Phe Lys Gly Val Thr Lys Ile Gly Asp
                85                  90                  95

Gly Asp Val Glu Lys Val Ala Lys Glu Lys Pro Asp Leu Ile Ile Val
            100                 105                 110

Tyr Ser Thr Asp Lys Asp Ile Lys Lys Tyr Gln Lys Val Ala Pro Thr
        115                 120                 125

Val Val Val Asp Tyr Asn Lys His Lys Tyr Leu Glu Gln Gln Glu Met
    130                 135                 140

Leu Gly Lys Ile Val Gly Lys Glu Asp Lys Val Lys Ala Trp Lys Lys
145                 150                 155                 160

Asp Trp Glu Glu Thr Thr Ala Lys Asp Gly Lys Glu Ile Lys Lys Ala
                165                 170                 175

Ile Gly Gln Asp Ala Thr Val Ser Leu Phe Asp Glu Phe Asp Lys Lys
            180                 185                 190

Leu Tyr Thr Tyr Gly Asp Asn Trp Gly Arg Gly Gly Glu Val Leu Tyr
        195                 200                 205

Gln Ala Phe Gly Leu Lys Met Gln Pro Glu Gln Gln Lys Leu Thr Ala
    210                 215                 220

Lys Ala Gly Trp Ala Glu Val Lys Gln Glu Glu Ile Glu Lys Tyr Ala
225                 230                 235                 240

Gly Asp Tyr Ile Val Ser Thr Ser Glu Gly Lys Pro Thr Pro Gly Tyr
                245                 250                 255

Glu Ser Thr Asn Met Trp Lys Asn Leu Lys Ala Thr Lys Glu Gly His
            260                 265                 270

Ile Val Lys Val Asp Ala Gly Thr Tyr Trp Tyr Asn Asp Pro Tyr Thr
        275                 280                 285

Leu Asp Phe Met Arg Lys Asp Leu Lys Glu Lys Leu Ile Lys Ala Ala
    290                 295                 300

Lys
305

<210> SEQ ID NO 28
<211> LENGTH: 256
<212> TYPE: PRT
<213> ORGANISM: Artificial Sequence
<220> FEATURE:
<223> OTHER INFORMATION: recombinant protein

<400> SEQUENCE: 28

Met Met Lys Arg Leu Asn Lys Leu Val Leu Gly Ile Ile Phe Leu Phe
1               5                   10                  15

Leu Val Ile Ser Ile Thr Ala Gly Cys Gly Ile Gly Lys Glu Ala Glu
            20                  25                  30

Val Lys Lys Ser Phe Glu Lys Thr Leu Ser Met Tyr Pro Ile Lys Asn
        35                  40                  45

Leu Glu Asp Leu Tyr Asp Lys Glu Gly Tyr Arg Asp Asp Gln Phe Asp
            50                  55                  60

Lys Asn Asp Lys Gly Thr Trp Ile Ile Asn Ser Glu Met Val Ile Gln
 65                  70                  75                  80

Pro Asn Asn Glu Asp Met Val Ala Lys Gly Met Val Leu Tyr Met Asn
                85                  90                  95

Arg Asn Thr Lys Thr Thr Asn Gly Tyr Tyr Val Asp Val Thr Lys
            100                 105                 110

Asp Glu Asp Glu Gly Lys Pro His Asp Asn Glu Lys Arg Tyr Pro Val
            115                 120                 125

Lys Met Val Asp Asn Lys Ile Ile Pro Thr Lys Glu Ile Lys Asp Glu
130                 135                 140

Lys Ile Lys Lys Glu Ile Glu Asn Phe Lys Phe Phe Val Gln Tyr Gly
145                 150                 155                 160

Asp Phe Lys Asn Leu Lys Asn Tyr Lys Asp Gly Asp Ile Ser Tyr Asn
                165                 170                 175

Pro Glu Val Pro Ser Tyr Ser Ala Lys Tyr Gln Leu Thr Asn Asp Asp
                180                 185                 190

Tyr Asn Val Lys Gln Leu Arg Lys Arg Tyr Asp Ile Pro Thr Ser Lys
            195                 200                 205

Ala Pro Lys Leu Leu Lys Gly Ser Gly Asn Leu Lys Gly Ser Ser
210                 215                 220

Val Gly Tyr Lys Asp Ile Glu Phe Thr Phe Val Glu Lys Lys Glu Glu
225                 230                 235                 240

Asn Ile Tyr Phe Ser Asp Ser Leu Asp Tyr Lys Lys Ser Gly Asp Val
                245                 250                 255

<210> SEQ ID NO 29
<211> LENGTH: 252
<212> TYPE: PRT
<213> ORGANISM: Artificial Sequence
<220> FEATURE:
<223> OTHER INFORMATION: recombinant protein

<400> SEQUENCE: 29

Met Lys Ala Thr Lys Leu Val Leu Gly Ala Val Ile Leu Gly Ser Thr
 1               5                  10                  15

Leu Leu Ala Gly Cys Gly Ile Gly Lys Glu Ala Glu Val Lys Lys Ser
                20                  25                  30

Phe Glu Lys Thr Leu Ser Met Tyr Pro Ile Lys Asn Leu Glu Asp Leu
            35                  40                  45

Tyr Asp Lys Glu Gly Tyr Arg Asp Asp Gln Phe Asp Lys Asn Asp Lys
 50                  55                  60

Gly Thr Trp Ile Ile Asn Ser Glu Met Val Ile Gln Pro Asn Asn Glu
 65                  70                  75                  80

Asp Met Val Ala Lys Gly Met Val Leu Tyr Met Asn Arg Asn Thr Lys
                85                  90                  95

Thr Thr Asn Gly Tyr Tyr Val Asp Val Thr Lys Asp Glu Asp Glu
            100                 105                 110

Gly Lys Pro His Asp Asn Glu Lys Arg Tyr Pro Val Lys Met Val Asp
            115                 120                 125

Asn Lys Ile Ile Pro Thr Lys Glu Ile Lys Asp Glu Lys Ile Lys Lys
130                 135                 140

Glu Ile Glu Asn Phe Lys Phe Phe Val Gln Tyr Gly Asp Phe Lys Asn
145                 150                 155                 160

Leu Lys Asn Tyr Lys Asp Gly Asp Ile Ser Tyr Asn Pro Glu Val Pro
            165                 170                 175

Ser Tyr Ser Ala Lys Tyr Gln Leu Thr Asn Asp Asp Tyr Asn Val Lys
        180                 185                 190

Gln Leu Arg Lys Arg Tyr Asp Ile Pro Thr Ser Lys Ala Pro Lys Leu
    195                 200                 205

Leu Leu Lys Gly Ser Gly Asn Leu Lys Gly Ser Ser Val Gly Tyr Lys
210                 215                 220

Asp Ile Glu Phe Thr Phe Val Glu Lys Glu Glu Asn Ile Tyr Phe
225                 230                 235                 240

Ser Asp Ser Leu Asp Tyr Lys Lys Ser Gly Asp Val
            245                 250

<210> SEQ ID NO 30
<211> LENGTH: 252
<212> TYPE: PRT
<213> ORGANISM: Artificial Sequence
<220> FEATURE:
<223> OTHER INFORMATION: recombinant protein

<400> SEQUENCE: 30

Met Lys Ala Thr Lys Leu Val Leu Gly Ala Val Ile Leu Gly Ser Thr
1               5                   10                  15

Leu Leu Ala Gly Ala Gly Ile Gly Lys Glu Ala Glu Val Lys Lys Ser
            20                  25                  30

Phe Glu Lys Thr Leu Ser Met Tyr Pro Ile Lys Asn Leu Glu Asp Leu
        35                  40                  45

Tyr Asp Lys Glu Gly Tyr Arg Asp Asp Gln Phe Asp Lys Asn Asp Lys
    50                  55                  60

Gly Thr Trp Ile Ile Asn Ser Glu Met Val Ile Gln Pro Asn Asn Glu
65                  70                  75                  80

Asp Met Val Ala Lys Gly Met Val Leu Tyr Met Asn Arg Asn Thr Lys
                85                  90                  95

Thr Thr Asn Gly Tyr Tyr Tyr Val Asp Val Thr Lys Asp Glu Asp Glu
            100                 105                 110

Gly Lys Pro His Asp Asn Glu Lys Arg Tyr Pro Val Lys Met Val Asp
        115                 120                 125

Asn Lys Ile Ile Pro Thr Lys Glu Ile Lys Asp Glu Lys Ile Lys Lys
    130                 135                 140

Glu Ile Glu Asn Phe Lys Phe Phe Val Gln Tyr Gly Asp Phe Lys Asn
145                 150                 155                 160

Leu Lys Asn Tyr Lys Asp Gly Asp Ile Ser Tyr Asn Pro Glu Val Pro
                165                 170                 175

Ser Tyr Ser Ala Lys Tyr Gln Leu Thr Asn Asp Asp Tyr Asn Val Lys
            180                 185                 190

Gln Leu Arg Lys Arg Tyr Asp Ile Pro Thr Ser Lys Ala Pro Lys Leu
        195                 200                 205

Leu Leu Lys Gly Ser Gly Asn Leu Lys Gly Ser Ser Val Gly Tyr Lys
    210                 215                 220

Asp Ile Glu Phe Thr Phe Val Glu Lys Glu Glu Asn Ile Tyr Phe
225                 230                 235                 240

Ser Asp Ser Leu Asp Tyr Lys Lys Ser Gly Asp Val
            245                 250

<210> SEQ ID NO 31

<211> LENGTH: 291
<212> TYPE: PRT
<213> ORGANISM: Artificial Sequence
<220> FEATURE:
<223> OTHER INFORMATION: recombinant protein

<400> SEQUENCE: 31

```
Ala Gln His Asp Glu Ala Lys Lys Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Ala Ala Pro Ser Gln Ser Ala Asn Val Leu Gly Glu Ala Gln Lys
        35                  40                  45

Leu Asn Asp Ser Gln Ala Pro Lys Ala Asp Ala Lys Arg Asn Asn Phe
    50                  55                  60

Asn Lys Asp Lys Lys Ser Ala Phe Tyr Glu Ile Leu Asn Met Pro Asn
65                  70                  75                  80

Leu Asn Glu Ala Gln Arg Asn Gly Phe Ile Gln Ser Leu Lys Ala Ala
                85                  90                  95

Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Lys Lys Asn
        115                 120                 125

Ala Phe Tyr Glu Ile Leu Asn Met Pro Asn Leu Asn Glu Glu Gln Arg
    130                 135                 140

Asn Gly Phe Ile Gln Ser Leu Lys Ala Ala Pro Ser Gln Ser Ala Asn
145                 150                 155                 160

Leu Leu Ser Glu Ala Lys Lys Leu Asn Glu Ser Gln Ala Pro Lys Ala
                165                 170                 175

Asp Asn Lys Phe Asn Lys Glu Lys Lys Asn Ala Phe Tyr Glu Ile Leu
            180                 185                 190

His Leu Pro Asn Leu Asn Glu Glu Gln Arg Asn Gly Phe Ile Gln Ser
        195                 200                 205

Leu Lys Ala Ala Pro Ser Gln Ser Ala Asn Leu Leu Ala Glu Ala Lys
    210                 215                 220

Lys Leu Asn Asp Ala Gln Ala Pro Lys Ala Asp Asn Lys Phe Asn Lys
225                 230                 235                 240

Glu Lys Lys Asn Ala Phe Tyr Glu Ile Leu His Leu Pro Asn Leu Thr
                245                 250                 255

Glu Glu Gln Arg Asn Gly Phe Ile Gln Ser Leu Lys Ala Ala Pro Ser
            260                 265                 270

Val Ser Lys Glu Ile Leu Ala Glu Ala Lys Lys Leu Asn Asp Ala Gln
        275                 280                 285

Ala Pro Lys
    290
```

<210> SEQ ID NO 32
<211> LENGTH: 312
<212> TYPE: PRT
<213> ORGANISM: Artificial Sequence
<220> FEATURE:
<223> OTHER INFORMATION: recombinant protein

<400> SEQUENCE: 32

```
Met Lys Ala Thr Lys Leu Val Leu Gly Ala Val Ile Leu Gly Ser Thr
1               5                   10                  15

Leu Leu Ala Gly Cys Ala Gln His Asp Glu Ala Lys Lys Asn Ala Phe
```

```
            20                  25                  30
Tyr Gln Val Leu Asn Met Pro Asn Leu Asn Ala Asp Gln Arg Asn Gly
         35                  40                  45

Phe Ile Gln Ser Leu Lys Ala Ala Pro Ser Gln Ser Ala Asn Val Leu
 50                  55                  60

Gly Glu Ala Gln Lys Leu Asn Asp Ser Gln Ala Pro Lys Ala Asp Ala
 65                  70                  75                  80

Lys Arg Asn Asn Phe Asn Lys Asp Lys Lys Ser Ala Phe Tyr Glu Ile
                 85                  90                  95

Leu Asn Met Pro Asn Leu Asn Glu Ala Gln Arg Asn Gly Phe Ile Gln
                100                 105                 110

Ser Leu Lys Ala Ala Pro Ser Gln Ser Thr Asn Val Leu Gly Glu Ala
            115                 120                 125

Lys Lys Leu Asn Glu Ser Gln Ala Pro Lys Ala Asp Asn Asn Phe Asn
130                 135                 140

Lys Glu Lys Lys Asn Ala Phe Tyr Glu Ile Leu Asn Met Pro Asn Leu
145                 150                 155                 160

Asn Glu Glu Gln Arg Asn Gly Phe Ile Gln Ser Leu Lys Ala Ala Pro
                165                 170                 175

Ser Gln Ser Ala Asn Leu Leu Ser Glu Ala Lys Lys Leu Asn Glu Ser
            180                 185                 190

Gln Ala Pro Lys Ala Asp Asn Lys Phe Asn Lys Glu Lys Lys Asn Ala
            195                 200                 205

Phe Tyr Glu Ile Leu His Leu Pro Asn Leu Asn Glu Glu Gln Arg Asn
        210                 215                 220

Gly Phe Ile Gln Ser Leu Lys Ala Ala Pro Ser Gln Ser Ala Asn Leu
225                 230                 235                 240

Leu Ala Glu Ala Lys Lys Leu Asn Asp Ala Gln Ala Pro Lys Ala Asp
                245                 250                 255

Asn Lys Phe Asn Lys Glu Lys Lys Asn Ala Phe Tyr Glu Ile Leu His
            260                 265                 270

Leu Pro Asn Leu Thr Glu Glu Gln Arg Asn Gly Phe Ile Gln Ser Leu
            275                 280                 285

Lys Ala Ala Pro Ser Val Ser Lys Glu Ile Leu Ala Glu Ala Lys Lys
        290                 295                 300

Leu Asn Asp Ala Gln Ala Pro Lys
305                 310

<210> SEQ ID NO 33
<211> LENGTH: 312
<212> TYPE: PRT
<213> ORGANISM: Artificial Sequence
<220> FEATURE:
<223> OTHER INFORMATION: recombinant protein

<400> SEQUENCE: 33

Met Lys Ala Thr Lys Leu Val Leu Gly Ala Val Ile Leu Gly Ser Thr
 1               5                  10                  15

Leu Leu Ala Gly Ala Ala Gln His Asp Glu Ala Lys Lys Asn Ala Phe
            20                  25                  30

Tyr Gln Val Leu Asn Met Pro Asn Leu Asn Ala Asp Gln Arg Asn Gly
         35                  40                  45

Phe Ile Gln Ser Leu Lys Ala Ala Pro Ser Gln Ser Ala Asn Val Leu
 50                  55                  60

Gly Glu Ala Gln Lys Leu Asn Asp Ser Gln Ala Pro Lys Ala Asp Ala
```

```
                65                  70                  75                  80
Lys Arg Asn Asn Phe Asn Lys Asp Lys Ser Ala Phe Tyr Glu Ile
                    85                  90                  95

Leu Asn Met Pro Asn Leu Asn Glu Ala Gln Arg Asn Gly Phe Ile Gln
                100                 105                 110

Ser Leu Lys Ala Ala Pro Ser Gln Ser Thr Asn Val Leu Gly Glu Ala
                115                 120                 125

Lys Lys Leu Asn Glu Ser Gln Ala Pro Lys Ala Asp Asn Asn Phe Asn
130                 135                 140

Lys Glu Lys Lys Asn Ala Phe Tyr Glu Ile Leu Asn Met Pro Asn Leu
145                 150                 155                 160

Asn Glu Glu Gln Arg Asn Gly Phe Ile Gln Ser Leu Lys Ala Ala Pro
                165                 170                 175

Ser Gln Ser Ala Asn Leu Leu Ser Glu Ala Lys Lys Leu Asn Glu Ser
                180                 185                 190

Gln Ala Pro Lys Ala Asp Asn Lys Phe Asn Lys Glu Lys Lys Asn Ala
                195                 200                 205

Phe Tyr Glu Ile Leu His Leu Pro Asn Leu Asn Glu Glu Gln Arg Asn
                210                 215                 220

Gly Phe Ile Gln Ser Leu Lys Ala Ala Pro Ser Gln Ser Ala Asn Leu
225                 230                 235                 240

Leu Ala Glu Ala Lys Lys Leu Asn Asp Ala Gln Ala Pro Lys Ala Asp
                245                 250                 255

Asn Lys Phe Asn Lys Glu Lys Lys Asn Ala Phe Tyr Glu Ile Leu His
                260                 265                 270

Leu Pro Asn Leu Thr Glu Glu Gln Arg Asn Gly Phe Ile Gln Ser Leu
                275                 280                 285

Lys Ala Ala Pro Ser Val Ser Lys Glu Ile Leu Ala Glu Ala Lys Lys
                290                 295                 300

Leu Asn Asp Ala Gln Ala Pro Lys
305                 310

<210> SEQ ID NO 34
<211> LENGTH: 283
<212> TYPE: PRT
<213> ORGANISM: Artificial Sequence
<220> FEATURE:
<223> OTHER INFORMATION: recombinant protein

<400> SEQUENCE: 34

Asn Thr Asn Ile Glu Asn Ile Gly Asp Gly Ala Glu Val Ile Lys Arg
1               5                   10                  15

Thr Glu Asp Val Ser Ser Lys Lys Trp Gly Val Thr Gln Asn Val Gln
                20                  25                  30

Phe Asp Phe Val Lys Asp Lys Lys Tyr Asn Lys Asp Ala Leu Ile Val
                35                  40                  45

Lys Met Gln Gly Phe Ile Asn Ser Arg Thr Ser Phe Ser Asp Val Lys
                50                  55                  60

Gly Ser Gly Tyr Glu Leu Thr Lys Arg Met Ile Trp Pro Phe Gln Tyr
65                  70                  75                  80

Asn Ile Gly Leu Thr Thr Lys Asp Pro Asn Val Ser Leu Ile Asn Tyr
                85                  90                  95

Leu Pro Lys Asn Lys Ile Glu Thr Thr Asp Val Gly Gln Thr Leu Gly
                100                 105                 110

Tyr Asn Ile Gly Gly Asn Phe Gln Ser Ala Pro Ser Ile Gly Gly Asn
```

```
            115                 120                 125
Gly Ser Phe Asn Tyr Ser Lys Thr Ile Ser Tyr Thr Gln Lys Ser Tyr
        130                 135                 140

Val Ser Glu Val Asp Lys Gln Asn Ser Lys Ser Val Lys Trp Gly Val
145                 150                 155                 160

Lys Ala Asn Glu Phe Val Thr Pro Asp Gly Lys Lys Ser Ala His Asp
                165                 170                 175

Arg Tyr Leu Phe Val Gln Ser Pro Asn Gly Pro Thr Gly Ser Ala Arg
            180                 185                 190

Glu Tyr Phe Ala Pro Asp Asn Gln Leu Pro Pro Leu Val Gln Ser Gly
        195                 200                 205

Phe Asn Pro Ser Phe Ile Thr Thr Leu Ser His Glu Lys Gly Ser Ser
    210                 215                 220

Asp Thr Ser Glu Phe Glu Ile Ser Tyr Gly Arg Asn Leu Asp Ile Thr
225                 230                 235                 240

Tyr Ala Thr Leu Phe Pro Arg Thr Gly Ile Tyr Ala Glu Arg Lys His
                245                 250                 255

Asn Ala Phe Val Asn Arg Asn Phe Val Val Arg Tyr Glu Val Asn Trp
            260                 265                 270

Lys Thr His Glu Ile Lys Val Lys Gly His Asn
        275                 280

<210> SEQ ID NO 35
<211> LENGTH: 304
<212> TYPE: PRT
<213> ORGANISM: Artificial Sequence
<220> FEATURE:
<223> OTHER INFORMATION: recombinant protein

<400> SEQUENCE: 35

Met Lys Ala Thr Lys Leu Val Leu Gly Ala Val Ile Leu Gly Ser Thr
1               5                   10                  15

Leu Leu Ala Gly Cys Asn Thr Asn Ile Glu Asn Ile Gly Asp Gly Ala
            20                  25                  30

Glu Val Ile Lys Arg Thr Glu Asp Val Ser Ser Lys Lys Trp Gly Val
        35                  40                  45

Thr Gln Asn Val Gln Phe Asp Phe Val Lys Asp Lys Lys Tyr Asn Lys
    50                  55                  60

Asp Ala Leu Ile Val Lys Met Gln Gly Phe Ile Asn Ser Arg Thr Ser
65                  70                  75                  80

Phe Ser Asp Val Lys Gly Ser Gly Tyr Glu Leu Thr Lys Arg Met Ile
                85                  90                  95

Trp Pro Phe Gln Tyr Asn Ile Gly Leu Thr Thr Lys Asp Pro Asn Val
            100                 105                 110

Ser Leu Ile Asn Tyr Leu Pro Lys Asn Lys Ile Glu Thr Thr Asp Val
        115                 120                 125

Gly Gln Thr Leu Gly Tyr Asn Ile Gly Gly Asn Phe Gln Ser Ala Pro
    130                 135                 140

Ser Ile Gly Gly Asn Gly Ser Phe Asn Tyr Ser Lys Thr Ile Ser Tyr
145                 150                 155                 160

Thr Gln Lys Ser Tyr Val Ser Glu Val Asp Lys Gln Asn Ser Lys Ser
                165                 170                 175

Val Lys Trp Gly Val Lys Ala Asn Glu Phe Val Thr Pro Asp Gly Lys
            180                 185                 190

Lys Ser Ala His Asp Arg Tyr Leu Phe Val Gln Ser Pro Asn Gly Pro
```

```
                    195                 200                 205
Thr Gly Ser Ala Arg Glu Tyr Phe Ala Pro Asp Asn Gln Leu Pro Pro
    210                 215                 220
Leu Val Gln Ser Gly Phe Asn Pro Ser Phe Ile Thr Thr Leu Ser His
225                 230                 235                 240
Glu Lys Gly Ser Ser Asp Thr Ser Glu Phe Glu Ile Ser Tyr Gly Arg
                245                 250                 255
Asn Leu Asp Ile Thr Tyr Ala Thr Leu Phe Pro Arg Thr Gly Ile Tyr
            260                 265                 270
Ala Glu Arg Lys His Asn Ala Phe Val Asn Arg Asn Phe Val Val Arg
        275                 280                 285
Tyr Glu Val Asn Trp Lys Thr His Glu Ile Lys Val Lys Gly His Asn
    290                 295                 300

<210> SEQ ID NO 36
<211> LENGTH: 304
<212> TYPE: PRT
<213> ORGANISM: Artificial Sequence
<220> FEATURE:
<223> OTHER INFORMATION: recombinant proetin

<400> SEQUENCE: 36

Met Lys Ala Thr Lys Leu Val Leu Gly Ala Val Ile Leu Gly Ser Thr
1               5                   10                  15
Leu Leu Ala Gly Ala Asn Thr Asn Ile Glu Asn Ile Gly Asp Gly Ala
                20                  25                  30
Glu Val Ile Lys Arg Thr Glu Asp Val Ser Ser Lys Lys Trp Gly Val
            35                  40                  45
Thr Gln Asn Val Gln Phe Asp Phe Val Lys Asp Lys Lys Tyr Asn Lys
        50                  55                  60
Asp Ala Leu Ile Val Lys Met Gln Gly Phe Ile Asn Ser Arg Thr Ser
65                  70                  75                  80
Phe Ser Asp Val Lys Gly Ser Gly Tyr Glu Leu Thr Lys Arg Met Ile
                85                  90                  95
Trp Pro Phe Gln Tyr Asn Ile Gly Leu Thr Thr Lys Asp Pro Asn Val
                100                 105                 110
Ser Leu Ile Asn Tyr Leu Pro Lys Asn Lys Ile Glu Thr Thr Asp Val
            115                 120                 125
Gly Gln Thr Leu Gly Tyr Asn Ile Gly Gly Asn Phe Gln Ser Ala Pro
        130                 135                 140
Ser Ile Gly Gly Asn Gly Ser Phe Asn Tyr Ser Lys Thr Ile Ser Tyr
145                 150                 155                 160
Thr Gln Lys Ser Tyr Val Ser Glu Val Asp Lys Gln Asn Ser Lys Ser
                165                 170                 175
Val Lys Trp Gly Val Lys Ala Asn Glu Phe Val Thr Pro Asp Gly Lys
                180                 185                 190
Lys Ser Ala His Asp Arg Tyr Leu Phe Val Gln Ser Pro Asn Gly Pro
            195                 200                 205
Thr Gly Ser Ala Arg Glu Tyr Phe Ala Pro Asp Asn Gln Leu Pro Pro
        210                 215                 220
Leu Val Gln Ser Gly Phe Asn Pro Ser Phe Ile Thr Thr Leu Ser His
225                 230                 235                 240
Glu Lys Gly Ser Ser Asp Thr Ser Glu Phe Glu Ile Ser Tyr Gly Arg
                245                 250                 255
Asn Leu Asp Ile Thr Tyr Ala Thr Leu Phe Pro Arg Thr Gly Ile Tyr
```

```
                260               265               270
Ala Glu Arg Lys His Asn Ala Phe Val Asn Arg Asn Phe Val Val Arg
        275               280               285

Tyr Glu Val Asn Trp Lys Thr His Glu Ile Lys Val Lys Gly His Asn
        290               295               300
```

<210> SEQ ID NO 37
<211> LENGTH: 41
<212> TYPE: DNA
<213> ORGANISM: Artificial Sequence
<220> FEATURE:
<223> OTHER INFORMATION: synthetic oligonucleotide

<400> SEQUENCE: 37
ggagatatac atatgatgaa agctactaaa ctggtactgg g          41

<210> SEQ ID NO 38
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 38
gttttgtttg ttgctggagc aacctgccag cagag                 35

<210> SEQ ID NO 39
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 39
ggttgctcca gcaacaaaca aaacactgct agtacag               37

<210> SEQ ID NO 40
<211> LENGTH: 41
<212> TYPE: DNA
<213> ORGANISM: Artificial Sequence
<220> FEATURE:
<223> OTHER INFORMATION: synthetic oligonucleotide

<400> SEQUENCE: 40
gtgatggtga tgttactact tataagtaat cgaaccatat g          41

<210> SEQ ID NO 41
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 41
catatgtata tctccttctt aaagttaaac                       30

<210> SEQ ID NO 42
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 42
taacatcacc atcaccatca cgattacaaa ga                    32

<210> SEQ ID NO 43
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 43
gcaggttgct ccagcgcagc agatgagcta agca                           34

<210> SEQ ID NO 44
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 44
gtgatggtga tgttattagg cttttgctgt tgctgaggt                       39

<210> SEQ ID NO 45
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 45
gctggagcaa cctgccagca gag                                       23

<210> SEQ ID NO 46
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 46
ctgctggcag gttgcgcaga ttctgatatt aatattaaaa ccggt               45

<210> SEQ ID NO 47
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 47
gtgatggtga tgttaatttg tcatttcttc tttttcccaa tcgat               45

<210> SEQ ID NO 48
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 48
ctgctggcag gttgcgggaa ccaaggtgaa aaaaataaca aag                 43

<210> SEQ ID NO 49
<211> LENGTH: 53
<212> TYPE: DNA
<213> ORGANISM: Artificial Sequence
<220> FEATURE:

<223> OTHER INFORMATION: synthetic oligonucleotide

<400> SEQUENCE: 49
gtgatggtga tgttattttg cagctttaat taattttct tttaaatctt tac                    53

<210> SEQ ID NO 50
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 50
ctgctggcag gttgcggcat aggtaaagaa gcggaag                                     37

<210> SEQ ID NO 51
<211> LENGTH: 44
<212> TYPE: DNA
<213> ORGANISM: Artificial Sequence
<220> FEATURE:
<223> OTHER INFORMATION: synthetic oligonucleotide

<400> SEQUENCE: 51
gtgatggtga tgttatacat ctccgctttt tttataatct aagc                             44

<210> SEQ ID NO 52
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 52
ctgctggcag gttgcgcaca gcatgatgaa gccaaaaaa                                   39

<210> SEQ ID NO 53
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 53
gtgatggtga tgttatttag gtgcctgtgc gtcgtt                                      36

<210> SEQ ID NO 54
<211> LENGTH: 47
<212> TYPE: DNA
<213> ORGANISM: Artificial Sequence
<220> FEATURE:
<223> OTHER INFORMATION: synthetic oligonucleotide

<400> SEQUENCE: 54
ctgctggcag gttgcaatac taatattgaa aatattggtg atggtgc                          47

<210> SEQ ID NO 55
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 55
gtgatggtga tgttaattat gtcctttcac tttaatttcg tgtgttttcc a                     51

```
<210> SEQ ID NO 56
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 56
caggtgcctc cagcaacaaa caaaacactg                                    30

<210> SEQ ID NO 57
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 57
caggtgcctc cagcgcagca gatgagc                                       27

<210> SEQ ID NO 58
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 58
gctggaggca cctgccagca gag                                           23

<210> SEQ ID NO 59
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 59
acctgccagc agagtagaac ccaggattac cgcgcc                             36

<210> SEQ ID NO 60
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 60
actctgctgg caggtgccgg cataggtaaa gaagcg                             36

<210> SEQ ID NO 61
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 61
actctgctgg caggtgccgg gaaccaaggt g                                  31

<210> SEQ ID NO 62
<211> LENGTH: 31
<212> TYPE: DNA
<213> ORGANISM: Artificial Sequence
<220> FEATURE:
<223> OTHER INFORMATION: synthetic oligonucleotide
```

```
<400> SEQUENCE: 62
actctgctgg caggtgccgc acagcatgat g                            31

<210> SEQ ID NO 63
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 63
actctgctgg caggtgccaa tactaatatt g                            31

<210> SEQ ID NO 64
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 64
actctgctgg caggtgccgc agattctgat att                          33

<210> SEQ ID NO 65
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 65
aaactgttgg ctttgaaatg ggttacgact ggttg                        35

<210> SEQ ID NO 66
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 66
aaaacaacca gtcgtaaccc atttcaaagc caaca                        35

<210> SEQ ID NO 67
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 67 aaactcctttt cgccacccgc gctactgggg agcag                       35

<210> SEQ ID NO 68
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 68
aaaactgctc cccagtagcg cgggtggcga aagga                        35

<210> SEQ ID NO 69
<211> LENGTH: 35
```

<212> TYPE: DNA
<213> ORGANISM: Artificial Sequence
<220> FEATURE:
<223> OTHER INFORMATION: synthetic oligonucleotide

<400> SEQUENCE: 69
aaacacaacg tttagagaaa atattgcaca aaccg    35

<210> SEQ ID NO 70
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 70
aaaacggcat gcacgtttcg cttacgacaa agaaa    35

<210> SEQ ID NO 71
<211> LENGTH: 120
<212> TYPE: DNA
<213> ORGANISM: Artificial Sequence
<220> FEATURE:
<223> OTHER INFORMATION: synthetic oligonucleotide

<400> SEQUENCE: 71
accgtgttat ctcgttggag atattcatgg cgtattttgg atgataacga ggcgcaaaaa    60
gttctcgtct ggtagaaaaa ccccgctgct gcggggtttt ttttgccttt agtaaattga   120

<210> SEQ ID NO 72
<211> LENGTH: 120
<212> TYPE: DNA
<213> ORGANISM: Artificial Sequence
<220> FEATURE:
<223> OTHER INFORMATION: synthetic oligonucleotide

<400> SEQUENCE: 72
tcaatttact aaaggcaaaa aaaccccgc agcagcgggg ttttctacc agacgagaac    60 tttttgcgcc tcgttatcat ccaaaatacg ccatgaatat ctccaacgag ataacacggt   120

<210> SEQ ID NO 73
<211> LENGTH: 120
<212> TYPE: DNA
<213> ORGANISM: Artificial Sequence
<220> FEATURE:
<223> OTHER INFORMATION: synthetic oligonucleotide

<400> SEQUENCE: 73
caagttgcgc cgctacacta tcaccagatt gatttttgcc ttatccgaaa ctggaaaagc    60
aaaagcctct cgcgaggaga ggccttcgcc tgatgataag ttcaagtttg cttcagaata   120

<210> SEQ ID NO 74
<211> LENGTH: 120
<212> TYPE: DNA
<213> ORGANISM: Artificial Sequence
<220> FEATURE:
<223> OTHER INFORMATION: synthetic oligonucleotide

<400> SEQUENCE: 74
tattctgaag caaacttgaa cttatcatca ggcgaaggcc tctcctcgcg agaggctttt    60
gcttttccag tttcggataa ggcaaaaatc aatctggtga tagtgtagcg gcgcaacttg   120

<210> SEQ ID NO 75

```
<211> LENGTH: 120
<212> TYPE: DNA
<213> ORGANISM: Artificial Sequence
<220> FEATURE:
<223> OTHER INFORMATION: synthetic oligonucleotide

<400> SEQUENCE: 75
tgttaattgt agctttgcta tgctagtagt agattttga taaatgtttt atggtcacaa     60
agttttagta acttctttaa aatcaatagc taaaataagt aacatcaaaa ataacgcgac   120

<210> SEQ ID NO 76
<211> LENGTH: 120
<212> TYPE: DNA
<213> ORGANISM: Artificial Sequence
<220> FEATURE:
<223> OTHER INFORMATION: synthetic oligonucleotide

<400> SEQUENCE: 76
gtcgcgttat ttttgatgtt acttatttta gctattgatt ttaaagaagt tactaaaact    60
ttgtgaccat aaaacattta tcaaaaatct actactagca tagcaaagct acaattaaca   120

<210> SEQ ID NO 77
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 77
cgttgtagac tttacatcgc cag                                            23

<210> SEQ ID NO 78
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 78
gtcttctctg aagcaggatc tgc                                            23

<210> SEQ ID NO 79
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 79
gccaaagaga ttgtgccgca gc                                             22

<210> SEQ ID NO 80
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 80
cggtagagta agtacgttgc cg                                             22

<210> SEQ ID NO 81
<211> LENGTH: 24
<212> TYPE: DNA
<213> ORGANISM: Artificial Sequence
```

<220> FEATURE:
<223> OTHER INFORMATION: synthetic oligonucleotide

<400> SEQUENCE: 81
gcatcatctt taatcgatgc gcgg                                    24

<210> SEQ ID NO 82
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 82
gctgtgtcgg ttaccagtac acc                                     23

<210> SEQ ID NO 83
<211> LENGTH: 21
<212> TYPE: PRT
<213> ORGANISM: Unknown
<220> FEATURE:
<223> OTHER INFORMATION: Lpp leader sequence

<400> SEQUENCE: 83

Met Lys Ala Thr Lys Leu Val Leu Gly Ala Val Ile Leu Gly Ser Thr
1               5                   10                  15

Leu Leu Ala Gly Cys
            20

<210> SEQ ID NO 84
<211> LENGTH: 14
<212> TYPE: DNA
<213> ORGANISM: Artificial Sequence
<220> FEATURE:
<223> OTHER INFORMATION: PCR primer

<400> SEQUENCE: 84
caggtgcctc cagc                                               14

<210> SEQ ID NO 85
<211> LENGTH: 23
<212> TYPE: DNA
<213> ORGANISM: Artificial Sequence
<220> FEATURE:
<223> OTHER INFORMATION: PCR primer

<400> SEQUENCE: 85
gctggaggca cctgccagca gag                                     23

<210> SEQ ID NO 86
<211> LENGTH: 69
<212> TYPE: DNA
<213> ORGANISM: Unknown
<220> FEATURE:
<223> OTHER INFORMATION: Lpp leader encoding sequence

<400> SEQUENCE: 86
atgaaagcta ctaaactggt actgggcgcg gtaatcctgg gttctactct gctggcaggt    60
tgctccagc                                                            69

<210> SEQ ID NO 87
<211> LENGTH: 36
<212> TYPE: DNA
<213> ORGANISM: Artificial Sequence
<220> FEATURE:

<223> OTHER INFORMATION: PCR primer

<400> SEQUENCE: 87
acctgccagc agagtagaac ccaggattac cgcgcc                                    36

<210> SEQ ID NO 88
<211> LENGTH: 36
<212> TYPE: DNA
<213> ORGANISM: Artificial Sequence
<220> FEATURE:
<223> OTHER INFORMATION: PCR primer

<400> SEQUENCE: 88
actctgctgg caggtgccgg cataggtaaa gaagcg                                    36

<210> SEQ ID NO 89
<211> LENGTH: 36
<212> TYPE: DNA
<213> ORGANISM: Artificial Sequence
<220> FEATURE:
<223> OTHER INFORMATION: PCR primer

<400> SEQUENCE: 89
acctgccagc agagtagaac ccaggattac cgcgcc                                    36

<210> SEQ ID NO 90
<211> LENGTH: 31
<212> TYPE: DNA
<213> ORGANISM: Artificial Sequence
<220> FEATURE:
<223> OTHER INFORMATION: PCR primer

<400> SEQUENCE: 90
actctgctgg caggtgccgg gaaccaaggt g                                         31

<210> SEQ ID NO 91
<211> LENGTH: 36
<212> TYPE: DNA
<213> ORGANISM: Artificial Sequence
<220> FEATURE:
<223> OTHER INFORMATION: PCR primer

<400> SEQUENCE: 91
acctgccagc agagtagaac ccaggattac cgcgcc                                    36

<210> SEQ ID NO 92
<211> LENGTH: 31
<212> TYPE: DNA
<213> ORGANISM: Artificial Sequence
<220> FEATURE:
<223> OTHER INFORMATION: PCR primer

<400> SEQUENCE: 92
actctgctgg caggtgccgc acagcatgat g                                         31

<210> SEQ ID NO 93
<211> LENGTH: 36
<212> TYPE: DNA
<213> ORGANISM: Artificial Sequence
<220> FEATURE:
<223> OTHER INFORMATION: PCR primer

<400> SEQUENCE: 93
acctgccagc agagtagaac ccaggattac cgcgcc                                    36

<210> SEQ ID NO 94
<211> LENGTH: 31
<212> TYPE: DNA
<213> ORGANISM: Artificial Sequence
<220> FEATURE:
<223> OTHER INFORMATION: PCR primer

<400> SEQUENCE: 94
actctgctgg caggtgccaa tactaatatt g            31

<210> SEQ ID NO 95
<211> LENGTH: 36
<212> TYPE: DNA
<213> ORGANISM: Artificial Sequence
<220> FEATURE:
<223> OTHER INFORMATION: PCR primer

<400> SEQUENCE: 95
acctgccagc agagtagaac ccaggattac cgcgcc       36

<210> SEQ ID NO 96
<211> LENGTH: 33
<212> TYPE: DNA
<213> ORGANISM: Artificial Sequence
<220> FEATURE:
<223> OTHER INFORMATION: PCR primer

<400> SEQUENCE: 96
actctgctgg caggtgccgc agattctgat att          33

<210> SEQ ID NO 97
<211> LENGTH: 102
<212> TYPE: DNA
<213> ORGANISM: Artificial Sequence
<220> FEATURE:
<223> OTHER INFORMATION: recombinant seqeunce

<400> SEQUENCE: 97
gttttagagc tatgctgttt tgaatggtcc caaaacttta gcaccagtgt accaggtgtt    60
atctttcttt tagagctatg ctgttttgaa tggtcccaaa ac                      102

<210> SEQ ID NO 98
<211> LENGTH: 102
<212> TYPE: DNA
<213> ORGANISM: Artificial Sequence
<220> FEATURE:
<223> OTHER INFORMATION: recombinant sequence

<400> SEQUENCE: 98
gttttagagc tatgctgttt tgaatggtcc caaaactcct ttcgccaccc gcgctactgg    60
ggagcacttt tagagctatg ctgttttgaa tggtcccaaa ac                      102

<210> SEQ ID NO 99
<211> LENGTH: 102
<212> TYPE: DNA
<213> ORGANISM: Artificial Sequence
<220> FEATURE:
<223> OTHER INFORMATION: recombinant sequence

<400> SEQUENCE: 99
gttttagagc tatgctgttt tgaatggtcc caaaacacaa cgtttagaga aaatattgca    60
caaacccttt tagagctatg ctgttttgaa tggtcccaaa ac                      102

<210> SEQ ID NO 100

<210> SEQ ID NO 100
<211> LENGTH: 23
<212> TYPE: PRT
<213> ORGANISM: Unknown
<220> FEATURE:
<223> OTHER INFORMATION: mutagenized Lpp leader sequence

<400> SEQUENCE: 100

Met Lys Ala Thr Lys Leu Val Leu Gly Ala Val Ile Leu Gly Ser Thr
1               5                   10                  15

Leu Leu Ala Gly Cys Ser Ser
            20

<210> SEQ ID NO 101
<211> LENGTH: 81
<212> TYPE: DNA
<213> ORGANISM: Unknown
<220> FEATURE:
<223> OTHER INFORMATION: Lpp leader encoding sequence

<400> SEQUENCE: 101
atgaaagcta ctaaactggt actgggcgcg gtaatcctgg gttctactct gctggcaggt      60
tgcggcatag gtaaagaagc g                                               81

<210> SEQ ID NO 102
<211> LENGTH: 27
<212> TYPE: PRT
<213> ORGANISM: Unknown
<220> FEATURE:
<223> OTHER INFORMATION: mutagenized Lpp leader sequence

<400> SEQUENCE: 102

Met Lys Ala Thr Lys Leu Val Leu Gly Ala Val Ile Leu Gly Ser Thr
1               5                   10                  15

Leu Leu Ala Gly Cys Gly Ile Gly Lys Glu Ala
            20                  25

<210> SEQ ID NO 103
<211> LENGTH: 76
<212> TYPE: DNA
<213> ORGANISM: Unknown
<220> FEATURE:
<223> OTHER INFORMATION: Lpp leader encoding sequence

<400> SEQUENCE: 103
atgaaagcta ctaaactggt actgggcgcg gtaatcctgg gttctactct gctggcaggt      60
tgcgggaacc aaggtg                                                     76

<210> SEQ ID NO 104
<211> LENGTH: 25
<212> TYPE: PRT
<213> ORGANISM: Unknown
<220> FEATURE:
<223> OTHER INFORMATION: mutagenized Lpp leader sequence

<400> SEQUENCE: 104

Met Lys Ala Thr Lys Leu Val Leu Gly Ala Val Ile Leu Gly Ser Thr
1               5                   10                  15

Leu Leu Ala Gly Cys Gly Asn Gln Gly
            20                  25

<210> SEQ ID NO 105
<211> LENGTH: 76
<212> TYPE: DNA
<213> ORGANISM: Unknown

```
<220> FEATURE:
<223> OTHER INFORMATION: Lpp leader encoding sequence

<400> SEQUENCE: 105
atgaaagcta ctaaactggt actgggcgcg gtaatcctgg gttctactct gctggcaggt    60
tgcgcacagc atgatg                                                    76

<210> SEQ ID NO 106
<211> LENGTH: 26
<212> TYPE: PRT
<213> ORGANISM: Unknown
<220> FEATURE:
<223> OTHER INFORMATION: mutagenized Lpp leader sequence

<400> SEQUENCE: 106

Met Lys Ala Thr Lys Leu Val Leu Gly Ala Val Ile Leu Gly Ser Thr
1               5                   10                  15

Leu Leu Ala Gly Cys Ala Gln His Asp Glu
            20                  25

<210> SEQ ID NO 107
<211> LENGTH: 76
<212> TYPE: DNA
<213> ORGANISM: Unknown
<220> FEATURE:
<223> OTHER INFORMATION: Lpp leader encoding sequence

<400> SEQUENCE: 107
atgaaagcta ctaaactggt actgggcgcg gtaatcctgg gttctactct gctggcaggt    60
tgcaatacta atattg                                                    76

<210> SEQ ID NO 108
<211> LENGTH: 25
<212> TYPE: PRT
<213> ORGANISM: Unknown
<220> FEATURE:
<223> OTHER INFORMATION: mutagenized Lpp leader sequence

<400> SEQUENCE: 108

Met Lys Ala Thr Lys Leu Val Leu Gly Ala Val Ile Leu Gly Ser Thr
1               5                   10                  15

Leu Leu Ala Gly Cys Asn Thr Asn Ile
            20                  25

<210> SEQ ID NO 109
<211> LENGTH: 78
<212> TYPE: DNA
<213> ORGANISM: Unknown
<220> FEATURE:
<223> OTHER INFORMATION: Lpp leader encoding sequence

<400> SEQUENCE: 109
atgaaagcta ctaaactggt actgggcgcg gtaatcctgg gttctactct gctggcaggt    60
tgcgcagatt ctgatatt                                                  78

<210> SEQ ID NO 110
<211> LENGTH: 26
<212> TYPE: PRT
<213> ORGANISM: Unknown
<220> FEATURE:
<223> OTHER INFORMATION: mutagenized Lpp leader sequence

<400> SEQUENCE: 110
```

```
Met Lys Ala Thr Lys Leu Val Leu Gly Ala Val Ile Leu Gly Ser Thr
1               5                   10                  15

Leu Leu Ala Gly Cys Ala Asp Ser Asp Ile
            20                  25

<210> SEQ ID NO 111
<211> LENGTH: 4
<212> TYPE: PRT
<213> ORGANISM: Unknown
<220> FEATURE:
<223> OTHER INFORMATION: lipobox sequence
<220> FEATURE:
<221> NAME/KEY: MISC_FEATURE
<222> LOCATION: (2)..(2)
<223> OTHER INFORMATION: Ala or Ser
<220> FEATURE:
<221> NAME/KEY: MISC_FEATURE
<222> LOCATION: (3)..(3)
<223> OTHER INFORMATION: Gly or Ala

<400> SEQUENCE: 111

Leu Xaa Xaa Cys
1
```